United States Patent
Schulte et al.

(10) Patent No.: US 11,814,421 B2
(45) Date of Patent: Nov. 14, 2023

(54) TRUNCATED VON WILLEBRAND FACTOR POLYPEPTIDES FOR TREATING HEMOPHILIA

(71) Applicant: CSL BEHRING LENGNAU AG, Lengnau (CH)

(72) Inventors: Stefan Schulte, Marburg (DE); Thomas Weimer, Gladenbach (DE); Sabine Pestel, Marburg (DE); Hubert Metzner, Marburg (DE); Steve Dower, Fitzroy North (AU)

(73) Assignee: CSL BEHRING LENGNAU AG, Lengnau (CH)

( * ) Notice: Subject to any disclaimer, the term of this patent is extended or adjusted under 35 U.S.C. 154(b) by 416 days.

(21) Appl. No.: 16/348,934

(22) PCT Filed: Nov. 10, 2017

(86) PCT No.: PCT/EP2017/078834
§ 371 (c)(1),
(2) Date: May 10, 2019

(87) PCT Pub. No.: WO2018/087267
PCT Pub. Date: May 17, 2018

(65) Prior Publication Data
US 2019/0263890 A1 Aug. 29, 2019

(30) Foreign Application Priority Data
Nov. 11, 2016 (EP) .................................... 16198501

(51) Int. Cl.
| C07K 14/755 | (2006.01) |
| A61P 7/04 | (2006.01) |
| A61K 9/00 | (2006.01) |
| A61K 38/37 | (2006.01) |
| C07K 14/765 | (2006.01) |
| A61K 38/36 | (2006.01) |

(52) U.S. Cl.
CPC .......... *C07K 14/755* (2013.01); *A61K 9/0019* (2013.01); *A61K 38/36* (2013.01); *A61K 38/37* (2013.01); *A61P 7/04* (2018.01); *C07K 14/765* (2013.01); *A61K 2300/00* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| 4,399,216 A | 8/1983 | Axel et al. |
| 4,970,300 A | 11/1990 | Fulton et al. |
| 6,403,077 B1 | 6/2002 | Strom et al. |
| 7,256,253 B2 | 8/2007 | Bridon et al. |
| 10,253,088 B2 * | 4/2019 | Wilson ................... A61K 38/37 |
| 10,688,157 B2 * | 6/2020 | Schulte ................ A61K 9/0019 |
| 10,806,774 B2 * | 10/2020 | Andrews ................ A61K 38/37 |
| 10,808,023 B2 * | 10/2020 | Andrews ................ C12N 15/62 |
| 10,905,747 B2 * | 2/2021 | Schulte ..................... A61P 7/04 |
| 2004/0087778 A1 | 5/2004 | Feige et al. |

FOREIGN PATENT DOCUMENTS

| EP | 0117058 | 8/1984 |
| EP | 0117060 | 8/1984 |
| WO | WO 94/15625 | 7/1994 |
| WO | WO 97/03193 | 1/1997 |
| WO | WO 97/11957 | 4/1997 |
| WO | WO 97/40145 | 10/1997 |
| WO | WO 99/55306 | 11/1999 |
| WO | WO 02/060951 | 8/2002 |
| WO | WO 02/103024 | 12/2002 |
| WO | WO 03/076567 | 9/2003 |
| WO | WO 03/087355 | 10/2003 |
| WO | WO 03/093313 | 11/2003 |
| WO | WO 2004/067566 | 8/2004 |
| WO | WO 2004/075923 | 9/2004 |
| WO | WO 2004/101740 | 11/2004 |
| WO | WO 2005/000892 | 1/2005 |
| WO | WO 2005/001025 | 1/2005 |

(Continued)

OTHER PUBLICATIONS

Yee et al., Blood. Jul. 17, 2014;124(3):445-52. doi: 10.1182/blood-2013-11-540534. Epub May 21, 2014. PMID: 24850761.*
Jayandharan et al., Haemophilia. Sep. 2005;11(5):481-91. doi: 10.1111/j.1365-2516.2005.01121.x. PMID: 16128892.*
Garcia et al., Res Pract Thromb Haemost. Dec. 29, 2019;4(1):64-71. doi: 10.1002/rth2.12280. eCollection Jan. 2020. PMID: 31989086.*
Castaman et al., Haematologica. Sep. 2019;104(9):1702-1709. doi: 10.3324/haematol.2019.221093. Epub Aug. 8, 2019. PMID: 31399527.*
Yee et al., "Partial in Vivo FVIII Stabilization by VWF Fragments," Blood, vol. 120, No. 21, 2012, Abstract 15, 2 pages.

(Continued)

*Primary Examiner* — Michael Szperka
(74) *Attorney, Agent, or Firm* — Finnegan, Henderson, Farabow, Garrett & Dunner, LLP

(57) ABSTRACT

The invention pertains to a polypeptide comprising a truncated von Willebrand Factor (VWF) and a half-life extending moiety, for use in the treatment of a blood coagulation disorder, said treatment comprising administering the polypeptide to a subject having a blood coagulation disorder and having endogenous Factor VIII (FVIII), wherein the activity level of endogenous FVIII in said subject before treatment with said polypeptide is reduced relative to the activity level of FVIII in normal human plasma (NHP) provided that the activity level of endogenous FVIII in said subject is at least 0.5% of the activity level of endogenous FVIII in normal human plasma (NHP), wherein the polypeptide is capable of binding to endogenous FVIII and wherein the endogenous FVIII level is increased following administration of said polypeptide.

24 Claims, 21 Drawing Sheets

Specification includes a Sequence Listing.

(56) References Cited

FOREIGN PATENT DOCUMENTS

| WO | WO 2005/063808 | | 7/2005 | |
|---|---|---|---|---|
| WO | WO 2006/000448 | | 1/2006 | |
| WO | WO 2006/053299 | | 5/2006 | |
| WO | WO 2006/071801 | | 7/2006 | |
| WO | WO 2006/108590 | | 10/2006 | |
| WO | WO 2007/090584 | | 8/2007 | |
| WO | WO 2007/126808 | | 11/2007 | |
| WO | WO 2007/144173 | | 12/2007 | |
| WO | WO 2008/077616 | | 7/2008 | |
| WO | WO 2009/156137 | | 12/2009 | |
| WO | WO 2011/060242 | | 5/2011 | |
| WO | WO-2011060242 | A2 * | 5/2011 | ............... A61P 7/04 |
| WO | WO 2013/083858 | | 6/2013 | |
| WO | WO 2013/093760 | | 6/2013 | |
| WO | WO 2013/106787 | | 7/2013 | |
| WO | WO-2013106787 | A1 * | 7/2013 | ............ A61K 47/62 |
| WO | WO 2013/120939 | | 8/2013 | |
| WO | WO 2014/011819 | | 1/2014 | |
| WO | WO 2014/173873 | | 10/2014 | |
| WO | WO-2014173873 | A1 * | 10/2014 | ............ A61K 47/65 |
| WO | WO 2014/198699 | | 12/2014 | |
| WO | WO-2014210558 | A1 * | 12/2014 | ............... A61P 1/02 |
| WO | WO 2016/000039 | | 1/2016 | |
| WO | WO 2016/188905 | | 12/2016 | |

OTHER PUBLICATIONS

Swystun et al., "FVIII Stabilization: VWF D'D3 Will Do," Blood, vol. 124, No. 3, 2014, pp. 313-315.
Yee et al., "A von Willebrand Factor Fragment Containing the D'D3 Domains is Sufficient to Stabilize Coagulation Factor VIII in Mice," Blood, vol. 124, No. 3, 2014, pp. 445-452.
Graham et al., "A New Technique for the Assay of Infectivity of Huma Adenovirus 5 DNA," Virology, 52, 1973, pp. 456-467.
Graham et al. "Characteristics of a Human Cell Line Transformed by DNA from Human Adenovirus Type 5," J. Gen. Virol., vol. 36, 1977, pp. 59-72.
Mantei et al., "Rabbit β-globin mRNA Production in Mouse L cells transformed with cloned rabbit β-globin chromosomal DNA," Nature, vol. 281, 1979, pp. 40-46.
Mather, "Establishment and Characterization of Two Distinct Mouse Testicular Epithelial Cell Lines," Biology of Reproduction, vol. 23, 1980, pp. 243-252.
Oslo, "Remington's Pharmaceutical Sciences," Medical Sciences, 16th Edition, 1980, 1 page.
Urlaub et al., "Isolation of Chinese Hamster Cell Mutants Deficient in Dihydrofolate Reductase Activity," Proc. Natl. Academy Science USA, vol. 77, No. 7, 1980, pp. 4216-4220.
Gething et al., "Cell-Surface Expression of Influenza Haemagglutinin From a Cloned DNA Copy of the RNA Gene," Nature, vol. 293, 1981, pp. 620-625.
Mather et al., "Culture of Testicular Cells in Hormone-Supplemented Serum-Free Medium," Annals New York Academy of Sciences, vol. 383, 1982, pp. 44-68.
Lee et al., "An Effect of Predilution on Potency Assays of Factor VII Concentrates," Thrombosis Research 30, 1983, pp. 511-519.

Collins et al., "Molecular Cloning of the Human Gene for von Willebrand Factor and Identification of the Transcription Initiation Site," Proc. Natl. Acad. Sci. USA, vol. 84, 1987, pp. 4393-4397.
Mansour et al., "Disruption of the Proto-oncogene int-2 in Mouse Embryo-derived Stem Cells: A General Strategy for Targeting Mutations to Non-Selectable Genes," Nature, vol. 336, 1988, pp. 348-352.
Kaufman et al., "Effect of von Willebrand Factor Coexpression on the Synthesis and Secretion of Factor VIII in Chinese Hamster Ovary Cells," Molecular and Cellular Biology, vol. 9, 1989, pp. 1233-1242.
Keown et al., "Methods for Introducing DNA into Mammalian Cells," Introducing DNA into Mammalian Cells, Methods in Enzymology, vol. 185, 1990, pp. 527-537.
Hawley-Nelson et al., "LipofectAMINE™ Reagent: A New, Higher Efficiency Polycationic Liposome Transfection Reagent," Focus, vol. 15, No. 3, 1993, pp. 73-79.
Fischer et al., "Structural Analysis of Recombinant von Willebrand Factor: Identification of Hetero- and Homo-Dimers," FEBS Letters, 351, 1994, pp. 345-348.
Bi et al., "Targeted Disruption of the Mouse Factor VIII Gene Produces a Model of Haemophilia A," Nature Genetics, vol. 10, 1995, pp. 119-121.
Bi et al., "Further Characterization of Factor VIII-Deficient Mice Created by Gene Targeting: RNA and Protein Studies," Blood, vol. 88, No. 9, 1996, pp. 3446-3450.
Denis et al., "A Mouse Model of Severe von Willebrand Disease: Defects in Hemostasis and Thrombosis," Proc. Natl. Acad. Sci USA, vol. 95, 1998, pp. 9524-9529.
Porteus et al., "Gene Targeting Using Zinc Finger Nucleases," Nature Biotechnology, vol. 23, No. 8, 2005, pp. 967-973.
Dumont et al., "Monomeric Fc Fusions," Biodrugs, vol. 20, No. 3, 2006, pp. 151-160.
Sadler et al., "Chapter 60 von Willebrand Disease: Diagnosis, Classification, and Treatment," HemostThromb, 2006, pp. 905-921.
Schellenberger et al., "A Recombinant Polypeptide Extends the In Vivo Half-Life of Peptides and Proteins in a Tunable Manner," Nature Biotechnology, vol. 27, No. 12, 2009, pp. 1186-1190.
Cui et al., "Targeted Integration in Rat and Mouse Embryos with Zinc-Finger Nucleases," Nature Biotechnology, vol. 29, No. 1, 2011, pp. 64-68.
Zhou et al., "Sequence and Structure Relationships Within von Willebrand Factor," Blood, vol. 120, No. 2, 2012, pp. 449-458.
Haberichter et al., "Chapter 13, Structure and Function of von Willebrand Factor," Hemostasis and Thrombosis, 2013, pp. 197-207.
Lenting et al., "von Willebrand Factor Biosynthesis, Secretion, and Clearance: Connecting the Far Ends," Blood, vol. 125, No. 13, 2015, pp. 2019-2028.
International Search Report and the Written Opinion of the International Searching Authority, issued in International Application No. PCT/EP2017/078834, dated Jan. 26, 2018, 11 pages.
European Search Report and Written Opinion, issued in EP Patent Application No. 16198501.5, dated May 29, 2017, 11 pages.
Podust et al., "Extension of in vivo half-life of biologically active molecules by XTEN protein polymers", Journal of Controlled Release 240 (2016) 52-66.
Rogers et al., "Recombinant Human Serum Albumin Fusion Proteins and Novel Applications in Drug Delivery and Therapy", Current Pharmaceutical Design, 2015, 21, 1899-1907.

* cited by examiner

TRUNCATED VON WILLEBRAND FACTOR POLYPEPTIDES FOR TREATING HEMOPHILIA

This application is the United States national stage entry under 35 U.S.C. § 371 of International Application No. PCT/EP2017/078834, filed on Nov. 10, 2017 and published as WO 2018/087267 A1, which claims priority to European Patent Application No. 16198501.5, filed on Nov. 11, 2016. The contents of these applications are each incorporated herein by reference in their entirety.

FIELD OF THE INVENTION

The present invention relates to products and methods for improving treatment of blood coagulation disorders.

BACKGROUND OF THE INVENTION

There are various bleeding disorders caused by deficiencies of blood coagulation factors. The most common disorders are hemophilia A and B, resulting from deficiencies of blood coagulation Factor VIII (FVIII) and IX, respectively. Another known bleeding disorder is von Willebrand's disease (VWD).

In plasma FVIII exists mostly as a non-covalent complex with von Willebrand Factor (VWF), and its coagulant function is to accelerate Factor IXa dependent conversion of Factor X to Xa.

Classic hemophilia or hemophilia A is an inherited bleeding disorder. It results from a chromosome X-linked deficiency of blood coagulation FVIII, and affects almost exclusively males with an incidence of between one and two individuals per 10,000. The X-chromosome defect is transmitted by female carriers who are not themselves hemophiliacs. The clinical manifestation of hemophilia A is an increased bleeding tendency.

In severe hemophilia A patients undergoing prophylactic treatment FVIII has to be administered intravenously (i.v.) about 3 times per week due to the short plasma half-life of FVIII of about 12 to 14 hours. Each i.v. administration is cumbersome, associated with pain and entails the risk of an infection especially as this is mostly done at home by the patients themselves or by the parents of children having been diagnosed for hemophilia A.

It would thus be highly desirable to increase the half-life of FVIII so that pharmaceutical compositions containing such FVIII would have to be administered less frequently.

Several attempts have been made to prolong the half-life of non-activated FVIII either by reducing its interaction with cellular receptors (WO 03/093313 A2, WO 02/060951 A2), by covalently attaching polymers to FVIII (WO 94/15625, WO 97/11957 and U.S. Pat. No. 4,970,300), by encapsulation of FVIII (WO 99/55306), by introduction of novel metal binding sites (WO 97/03193), by covalently attaching the A2 domain to the A3 domain either by peptidic (WO 97/40145 and WO 03/087355) or disulfide linkage (WO 02/103024A2) or by covalently attaching the A1 domain to the A2 domain (WO2006/108590).

Another approach to enhance the functional half-life of FVIII or VWF is by PEGylation of FVIII (WO 2007/126808, WO 2006/053299, WO 2004/075923) or by PEGylation of VWF (WO 2006/071801) The increased half-life of pegylated VWF would indirectly also enhance the half-life of FVIII present in plasma. Also fusion proteins of FVIII have been described (WO 2004/101740, WO2008/077616 and WO 2009/156137).

VWF, which is missing, functionally defect or only available in reduced quantity in different forms of von Willebrand disease (VWD), is a multimeric adhesive glycoprotein present in the plasma of mammals, which has multiple physiological functions. During primary hemostasis VWF acts as a mediator between specific receptors on the platelet surface and components of the extracellular matrix such as collagen. Moreover, VWF serves as a carrier and stabilizing protein for procoagulant FVIII. VWF is synthesized in endothelial cells and megakaryocytes as a 2813 amino acid precursor molecule. The amino acid sequence and the cDNA sequence of wild-type VWF are disclosed in Collins et al. 1987, Proc. Natl. Acad. Sci. USA 84:4393-4397. The precursor polypeptide, pre-pro-VWF, consists of an N-terminal 22-residue signal peptide, followed by a 741-residue pro-peptide and the 2050-residue polypeptide found in mature plasma VWF (Fischer et al., FEBS Lett. 351: 345-348, 1994). After cleavage of the signal peptide in the endoplasmatic reticulum a C-terminal disulfide bridge is formed between two monomers of VWF. During further transport through the secretory pathway 12 N-linked and 10 O-linked carbohydrate side chains are added. More important, VWF dimers are multimerized via N-terminal disulfide bridges and the propeptide of 741 amino acids length is cleaved off by the enzyme PACE/furin in the late Golgi apparatus.

Once secreted into plasma the protease ADAMTS13 can cleave high-molecular weight VWF multimers within the A1 domain of VWF. Plasma VWF therefore consists of a whole range of multimers ranging from single dimers of 500 kDa to multimers consisting of up to more than 20 dimers of a molecular weight of over 10,000 kDa. The VWF-HMWM hereby having the strongest hemostatic activity, which can be measured in ristocetin cofactor activity (VWF:RCo). The higher the ratio of VWF:RCoNWF antigen, the higher the relative amount of high molecular weight multimers.

In plasma FVIII binds with high affinity to VWF, which protects it from premature elimination and thus, plays in addition to its role in primary hemostasis a crucial role to stabilize FVIII, regulate plasma levels of FVIII and as a consequence is also a central factor to control secondary hemostasis. The half-life of non-activated FVIII bound to VWF is about 12 to 14 hours in plasma. In von Willebrand disease type 3, where no or almost no VWF is present, the half-life of FVIII is only about 2 to 6 hours, leading to symptoms of mild to moderate hemophilia A in such patients due to decreased concentrations of FVIII. The stabilizing effect of VWF on FVIII has also been used to aid recombinant expression of FVIII in CHO cells (Kaufman et al. 1989, Mol Cell Biol 9:1233-1242). Von Willebrand disease type 2N is characterized by low FVIII levels due to mutations in VWF which affect the binding of FVIII to VWF. FVIII levels in VWD type 2N patients are in a range between about 3 IU/dL and 30 IU/dL, typically below 20 IU/dL, depending on the specific mutation in VWF. Von-Willebrand disease type 1 is characterized by a reduced endogenous FVIII activity level compared to the endogenous FVIII activity level in normal human plasma (Sadler J. E. and Blinder M., Von Willebrand Disease: Diagnosis, Classification, and Treatment; in: Hemostasis and Thrombosis, eds. Colman, Marder, Clowes, George, Aird, and Goldhaber, Lippincott Williams & Wilkins 2006, pp 905-921).

VWF-derived polypeptides, in particular VWF fragments, have been described to stabilize FVIII in vitro and in vivo. WO 2013/106787 A1 is directed at chimeric proteins comprising certain VWF fragments and a FVIII protein. Those chimeric hetero-dimers of FVIII and VWF-fragment do have a fixed molar ratio of VWF to FVIII of 1:1. WO 2014/198699 A2 and WO 2013/083858 A2 describe VWF fragments and their use in the treatment of hemophilia. It was found that bioavailability of FVIIIs may be significantly improved upon extravascular co-administration with similar molar amounts of VWF fragments. High molar excess of VWF over FVIII was said to be not desirable, and in experiments with VWF fragments co-administered s.c. with FVIII it was found that the VWF dose was not critical for FVIII bioavailability. Thus molar ratios of VWF fragments over FVIII were limited to maximally 50:1 and preferred ranges to maximally 1.5:1. WO 2011/060242 A2 discloses fusion polypeptides comprising certain VWF fragments and an antibody Fc region proposing specific molar ratios of VWF fragment over FVIII of up to 10:1. WO2013/093760 A2 describes a method for preparing a protein, comprising co-expressing FVIII or VWF polypeptides, including truncated forms of VWF, with a recombinant α-2,3-sialyltransferase. Yee et al. (2014) Blood 124(3):445-452 found that a VWF fragment containing the D'D3 domains is sufficient to stabilize Factor VIII in VWF-deficient mice. However, although a VWF D'D3-Fc fusion protein exhibited markedly prolonged survival when transfused into FVIII-deficient mice, the VWF D'D3-Fc fusion protein did not prolong the survival of co-transfused FVIII.

There is an ongoing need for methods increasing the half-life of FVIII and FVIII products with reduced administration frequency.

SUMMARY OF THE INVENTION

It has been found by the inventors that the in vivo half-life of endogenous Factor VIII can be prolonged by administration of a truncated and half-life extended VWF polypeptide (polypeptide of the invention). It has also been found that the in vivo half-life of endogenous Factor VIII can even be prolonged by administration of said polypeptide of the invention without necessary co-administration of exogenous FVIII. The patients have a reduced level of endogenous FVIII before treatment with said polypeptide relative to the level of FVIII in normal human plasma (NHP). The level of endogenous FVIII in said patients is at least 0.5% of the level of endogenous FVIII in normal human plasma (NHP). The polypeptide of the invention is capable of elevating endogenous FVIII levels. This allows for the prophylactic treatment of patients, without necessary co-administration of exogenous FVIII. If exogenous FVIII is co-administered, the follow-up treatment of a bleeding event can be done with the polypeptide of the invention only, i.e. without continued co-administration of exogenous FVIII. It has also been found by the inventors that patients could benefit from a treatment with the polypeptide of the invention by administration of an exogenous FVIII and thereby providing for an endogenous FVIII in said subject, the in vivo half-life of such an endogenous Factor VIII being prolonged.

The present invention therefore relates particularly to the following embodiments [1] to [91]:

[1] A polypeptide comprising a truncated von Willebrand Factor (VWF) and a half-life extending moiety, for use in the treatment of a blood coagulation disorder, said treatment comprising administering the polypeptide to a subject having a blood coagulation disorder and having endogenous Factor VIII (FVIII), wherein the activity level of endogenous FVIII in said subject before treatment with said polypeptide is reduced relative to the activity level of FVIII in normal human plasma (NHP) provided that the activity level of endogenous FVIII in said subject is at least 0.5% of the activity level of endogenous FVIII in normal human plasma (NHP), wherein the polypeptide is capable of binding to endogenous FVIII and wherein the endogenous FVIII level is increased following administration of said polypeptide and wherein (i) said polypeptide is administered for prophylactic prevention of a bleeding event, wherein
   a) said treatment either does not comprise co-administration of exogenous FVIII, or
   b) said treatment comprising that an exogenous FVIII is administered and thereby providing for the endogenous FVIII in said subject; or (ii) said polypeptide is co-administered together with exogenous FVIII for the treatment of a bleeding event or for initiation of a prophylactic treatment regime, wherein for follow-up treatments said polypeptide is administered without co-administration of exogenous FVIII.

The present invention in particular provides the advantage that a patient may benefit from a remaining low level of endogenous FVIII which can be stabilized by the polypeptide of the invention. The stabilization of endogenous FVIII might allow for higher protective plasma levels of FVIII. According to a certain aspect of the invention the polypeptide optionally allows for an extravascular administration of said polypeptide comprising a truncated VWF and a half-life extending moiety. In addition, the frequency of administration can be reduced by applying the polypeptide of the invention. Administration of the polypeptide allows for an increase of endogenous FVIII activity levels which can be elevated into a physiological range or prolonged in a physiological range. By administration of the polypeptide pathological aPTT values can be reduced to physiological values. Since exogenous FVIII does not necessarily need to be administered according to the therapy of the invention, the potential of formation of inhibitors against FVIII might be reduced. Thus, patients may benefit from a treatment with the polypeptide of the invention even without necessary co-administration of FVIII.

[2] The polypeptide for use according to embodiment [1], wherein the truncated von Willebrand Factor (VWF) provides for the capability of the polypeptide's binding to endogenous FVIII.

[3] The polypeptide for use according to embodiment [1] or embodiment [2], wherein the endogenous FVIII level is increased following administration of said polypeptide to a level of at least 1%, or preferably at least 2%, at least 5%, at least 10%, at least 20%, at least 30%, at least 40%, at least 50%, at least 60%, at least 70%, at least 80%, at least 90% or at least 100% of the activity level of endogenous FVIII in normal human plasma (NHP).

[4] The polypeptide for use according to any one of the preceding embodiments, wherein the truncated von Willebrand Factor (VWF) is a human truncated von Willebrand Factor (VWF).

[5] The polypeptide for use according to any one of the preceding embodiments, wherein the activity level of endogenous FVIII in said subject before treatment with said polypeptide is less than 80%, less than 60%, less than 40%, less than 30%, less than 20% or less than 10% of the activity level of endogenous FVIII in NHP.

[6] The polypeptide for use according to any one of the preceding embodiments, wherein the activity level of endogenous FVIII in said subject is at least 1%, at least 2%, at least 3%, at least 4% or at least 5% of the activity level of endogenous FVIII in NHP.

[7] The polypeptide for use according to any one of the preceding embodiments, wherein said blood coagulation disorder is hemophilia A or von-Willebrand disease, preferably von-Willebrand disease type 2N, von-Willebrand disease type 3 or von-Willebrand disease type 1.
[8] The polypeptide for use according to any one of the preceding embodiments, wherein said blood coagulation disorder is moderate hemophilia A, which is typically characterized by an endogenous FVIII activity level before or without treatment which is in a range between 1% to 5% of the endogenous FVIII activity level in NHP.
[9] The polypeptide for use according to embodiment [8], wherein treatment option (i) a) or treatment option (ii) is being applied.
[10] The polypeptide for use according to any one of embodiments [1] to [7], wherein said blood coagulation disorder is mild hemophilia A, typically characterized by an endogenous FVIII activity level before or without treatment which is greater than 5% and up to 40% of the endogenous FVIII activity level in NHP.
[11] The polypeptide for use according to embodiment [10], wherein treatment option (i) a) or treatment option (ii) is being applied.
[12] The polypeptide for use according to any one of embodiments [1] to [7], wherein said blood coagulation disorder is von-Willebrand disease type 3, typically characterized by an endogenous FVIII activity level before or without treatment which is usually in a range between about 1 IU/dL and about 20 IU/dL FVIII activity level corresponding to about 1% to about 20% of the endogenous FVIII activity level in NHP. Most of the patients have an endogenous FVIII activity level below 10 IU/dL, thus a level below 10% of the endogenous FVIII activity level in NHP.
[13] The polypeptide for use according to any one of embodiments [1] to [7], wherein said blood coagulation disorder is von-Willebrand disease type 2N, typically characterized by an endogenous FVIII activity level before or without treatment which is in a range between about 3 IU/dL and about 30 IU/dL FVIII activity level, corresponding to about 3% to about 30% of the endogenous FVIII activity level in NHP. Most of the patients have an endogenous FVIII activity level below 20 IU/dL, thus a level below 20% of the endogenous FVIII activity level in NHP. Thus, subjects having von-Willebrand disease type 2N have an endogenous FVIII activity level from 0.03 IU/mL to 0.3 IU/mL in plasma, typically below 0.2 IU/mL.
[14] The polypeptide for use according to any one of embodiments [1] to [7], wherein said blood coagulation disorder is von-Willebrand disease type 1 typically characterized by an endogenous FVIII activity level before or without treatment which is reduced compared to the endogenous FVIII activity level in NHP.
[15] The polypeptide for use according to any one of embodiments [12] to [14], wherein treatment option (i) a) or treatment option (ii) is being applied.
[16] The polypeptide for use according to any one of embodiments [1] to [7], wherein treatment option (i) b) is being applied.
[17] The polypeptide for use according to embodiment [16], wherein said blood coagulation disorder is hemophilia A.
[18] The polypeptide for use according to embodiment [17], wherein the coagulation disorder is severe hemophilia A typically characterized by an endogenous FVIII activity level before or without treatment that is below 1% of the endogenous FVIII activity in NHP.
[19] The polypeptide for use according to embodiment [17] or [18], wherein said exogenous FVIII has been administered before or after administration of said polypeptide; or wherein said exogenous FVIII is being administered simultaneously with said polypeptide.
[20] The polypeptide for use according to embodiment [19], wherein said exogenous FVIII has been administered before said polypeptide.
[21] The polypeptide for use according to any one of preceding embodiments, wherein the subject is currently being treated or has been treated by a FVIII gene therapy or FVIII gene transfer approach for provision of endogenous FVIII activity, and whereas the endogenous FVIII activity levels preferably fall below one of the FVIII activity levels as defined in embodiment [5].
[22] The polypeptide for use according to embodiment [21], wherein treatment option (i) b) is being applied, whereas the "exogenous" FVIII is provided by the FVIII gene therapy or FVIII gene transfer approach thereby providing for the endogenous FVIII.
[23] The polypeptide for use according to any one of embodiments [16] to [20], wherein the activity level of FVIII within the subject's plasma resulting from a exogenous FVIII administered and the activity level of FVIII within the subject's plasma formed by the subject endogenously, if any FVIII is formed by the subject, are being considered together to be at least 0.5% of the activity level of endogenous FVIII in normal human plasma (NHP). With other words according to this embodiment, the endogenous FVIII being at least 0.5% of the activity level of endogenous FVIII in normal human plasma (NHP) may be a mixture of FVIII originating from exogenous FVIII, preferably previously administered FVIII, and endogenous FVIII formed by the subject or may be merely a remaining FVIII previously administered in case no FVIII is formed by the subject.
[24] The polypeptide for use according to any one of the preceding embodiments, wherein the polypeptide is administered intravenously and/or extravascularly. In case of an extravascular administration, subcutaneous administration is preferred.
[25] The polypeptide for use according to any one of embodiments [16] to [23], wherein the exogenous FVIII is administered intravenously, i.e. thus providing endogenous FVIII.
[26] The polypeptide for use according to embodiment to [25], wherein said polypeptide is administered via a different route of administration than FVIII, preferably said polypeptide is administered subcutaneously.
[27] The polypeptide for use according to any one of embodiments [16] to [25], wherein said polypeptide is administered intravenously.
[28] The polypeptide for use according to any one of the preceding embodiments, wherein the subject is a human being.
[29] The polypeptide for use according to any one of the preceding embodiments, wherein the polypeptide is a dimer.
[30] The polypeptide for use according to any one of the preceding embodiments, wherein the truncated VWF comprises (a) amino acids 776 to 805 of SEQ ID NO:4 or (b) an amino acid sequence having a sequence identity of at least 90%, at least 95%; at least 96%, at least 97%, at least 98% or at least 99% to amino acids 776 to 805 of SEQ ID NO:4.
[31] The polypeptide for use according to any one of the preceding embodiments, wherein the truncated VWF comprises (a) amino acids 766 to 864 of SEQ ID NO:4 or (b) an amino acid sequence having a sequence identity of at least 90%, at least 95%; at least 96%, at least 97%, at least 98% or at least 99% to amino acids 766 to 864 of SEQ ID NO:4.

[32] The polypeptide for use according to any one of the preceding embodiments, wherein the truncated VWF comprises amino acids 764 to 1242 of SEQ ID NO:4.

[33] The polypeptide for use according to any one of the preceding embodiments, wherein the truncated VWF consists of (a) amino acids 764 to 1242 of SEQ ID NO:4, (b) an amino acid sequence having a sequence identity of at least 90% to amino acids 764 to 1242 of SEQ ID NO:4, or (c) a fragment of (a) or (b).

[34] The polypeptide for use according to any one of the preceding embodiments, wherein the truncated VWF lacks amino acids 1243 to 2813 of SEQ ID NO:4.

[35] The polypeptide for use according to any one of the preceding embodiments, wherein the half-life extending moiety is a heterologous amino acid sequence fused to the truncated VWF.

[36] The polypeptide for use according to embodiment [35], wherein said heterologous amino acid sequence comprises or consists of a polypeptide selected from the group consisting of transferrin and fragments thereof, the C-terminal peptide of human chorionic gonadotropin, an XTEN sequence, homo-amino acid repeats (HAP), proline-alanine-serine repeats (PAS), albumin, afamin, alpha-fetoprotein, Vitamin D binding protein, polypeptides capable of binding under physiological conditions to albumin or immunoglobulin constant regions, polypeptides capable of binding to the neonatal Fc receptor (FcRn), particularly immunoglobulin constant regions and portions thereof, preferably the Fc portion of immunoglobulin, and combinations thereof. The immunoglobulin constant region or portions thereof is preferably an Fc fragment of immunoglobulin G1, an Fc fragment of immunoglobulin G2 or an Fc fragment of immunoglobulin A.

[37] The polypeptide for use according to any one of the preceding embodiments, wherein the half-life extending moiety is conjugated to the polypeptide.

[38] The polypeptide for use according to embodiment [37], wherein said half-life-extending moiety is selected from the group consisting of hydroxyethyl starch (HES), polyethylene glycol (PEG), polysialic acids (PSAs), elastin-like polypeptides, heparosan polymers, hyaluronic acid and albumin binding ligands, e.g. fatty acid chains or albumin binding peptides, and combinations thereof.

[39] The polypeptide for use according to any one of the preceding embodiments, wherein the pharmacokinetic parameters of the endogenous FVIII are improved by the administration of the polypeptide, in particular wherein the mean residence time (MRT) of the endogenous FVIII is increased and/or the half-life of the endogenous FVIII is prolonged and/or clearance of the endogenous FVIII is reduced.

[40] The use of a polypeptide as defined in any one of preceding embodiments [1] to [39] for stabilizing and/or increasing the plasma half-life of endogenous FVIII.

[41] The polypeptide for use according to any of embodiments [1] to [40], provided treatment option (ii) is applied and said polypeptide is co-administered together with exogenous FVIII for the treatment of a bleeding event or for initiation of a prophylactic treatment regime, wherein for follow-up treatments said polypeptide is administered without co-administration of exogenous FVIII, wherein the molar ratio of the polypeptide to be co-administered to the exogenous FVIII is greater than 50. The co-administered exogenous FVIII may be plasma derived or any recombinant FVIII. The recombinant exogenous FVIII may be for example a single-chain Factor VIII, preferably consisting of the amino acid sequence SEQ ID NO:5.

[42] The polypeptide for use according to any one of embodiments [1] to [41], in case that treatment option (i) b) or treatment option (ii) is applied, wherein the molar ratio of the polypeptide to the exogenous FVIII is at least 50.

[43] The polypeptide for use according to embodiment [42], wherein the molar ratio of the polypeptide to the exogenous FVIII is at least 75.

[44] The polypeptide for use according to embodiment [42], wherein the molar ratio of the polypeptide to the exogenous FVIII is at least 100.

[45] The polypeptide for use according to embodiment [42], wherein the molar ratio of the polypeptide to the exogenous FVIII is at least 200.

[46] The polypeptide for use according to embodiment [42], wherein the molar ratio of the polypeptide to the exogenous FVIII is at least 300.

[47] The polypeptide for use according to embodiment [42], wherein the molar ratio of the polypeptide to the exogenous FVIII is at least 400 or at least 500.

[48] The polypeptide for use according to any one of the preceding embodiments, wherein the polypeptide is a glycoprotein comprising N-glycans, and wherein at least 75% of said N-glycans comprise, on average, at least one sialic acid moiety.

[49] The polypeptide for use according to embodiment [48], wherein at least 85% of said N-glycans comprise, on average, at least one sialic acid moiety.

[50] The polypeptide for use according to embodiment [49] wherein at least 95% of said N-glycans comprise, on average, at least one sialic acid moiety.

[51] The polypeptide for use according to any one of the preceding embodiments, wherein the polypeptide is a dimer, preferably a homodimer comprising two polypeptides (monomers) as defined in one of the herein disclosed embodiments, and the two monomers forming the dimer are covalently linked to each other via one or more disulfide bridges formed by cysteine residues within the truncated VWF.

[52] The polypeptide for use according to embodiment [51], wherein the cysteine residues forming the one or more disulfide bridges is/are selected from the group consisting of Cys-1099, Cys-1142, Cys-1222, Cys-1225, Cys-1227 and combinations thereof, preferably Cys-1099 and Cys-1142, wherein the amino acid numbering refers to SEQ ID NO:4.

[53] The polypeptide for use according to any one of embodiments [51] to [52], wherein the affinity of said dimeric polypeptide to FVIII (either exogenous or endogenous FVIII) is greater than the affinity of a monomeric polypeptide to said FVIII, said monomeric polypeptide having the same amino acid sequence as a monomeric subunit of the dimeric polypeptide.

[54] The polypeptide for use according to any one of embodiments [51] to [53], wherein the ratio dimer:monomer of the polypeptide of the invention is at least 1.5, preferably at least 2, more preferably at least 2.5 or at least 3. Most preferably all polypeptides of the invention are present as dimers.

[55] The polypeptide for use according to any one of embodiments [51] to [54], the polypeptide has a FVIII binding affinity characterized by a dissociation constant $K_D$ of less than 1 nM, preferably less than 500 pM, less than 200 pM, less than 100 pM, less than 90 pM or less than 80 pM.

[56] The polypeptide for use according to embodiment [55], wherein the dissociation constant $K_D$ ranges from 0.1 pM to 500 pM, from 0.5 pM to 200 pM, from 0.75 pM to 100 pM or most preferred from 1 pM to 80 pM.

[57] The polypeptide for use according to any one of embodiments [51] to [56], wherein the dimeric polypeptide has a FVIII binding affinity characterized by a dissociation constant $K_D$ and said dissociation constant $K_D$ of the dimeric polypeptide is reduced compared to the dissociation constant $K_D$ of a monomeric polypeptide, preferably by a factor of at least 10, by a factor of at least 100, by a factor of at least 500 or by a factor of at least 1000.

[58] The polypeptide for use according to any one of the preceding embodiments, wherein the pharmacokinetic parameters of the endogenous FVIII are improved by the administration of the polypeptide, preferably wherein the mean residence time (MRT) of the endogenous FVIII is increased and/or the half-life of the endogenous FVIII is prolonged and/or clearance of the endogenous FVIII is reduced, particularly when compared to the corresponding FVIII pharmacokinetic parameters in normal human plasma (NHP) or when compared to the corresponding FVIII pharmacokinetic parameters in a subject not receiving the polypeptide.

[59] The polypeptide for use according to embodiment [58], wherein said increase in MRT and/or terminal half-life of the endogenous FVIII is at least 50%.

[60] The polypeptide for use according to embodiment [59], wherein said increase in MRT and/or terminal half-life of the endogenous FVIII is at least 100%.

[61] The polypeptide for use according to embodiment [58], wherein the clearance of the endogenous FVIII is decreased by the administration of the polypeptide and said decrease is at least 25%.

[62] The polypeptide for use according to embodiment [61], wherein said decrease is at least 50%.

[63] The polypeptide for use according to embodiment [62], wherein said decrease is at least 100%.

[64] The polypeptide for use according to any one of the preceding embodiments, wherein the plasma half-life of said polypeptide is increased when compared to the plasma half-life of endogenous VWF and/or when compared to the plasma half-life of VWF of normal human plasma (NHP).

[65] The polypeptide for use according to embodiment [64], wherein the plasma half-life of said polypeptide is at least 25% higher, in particular, at least 50% higher, at least 75% higher or at least 100% higher than the half-life of the endogenous VWF and/or of the half-life of VWF of normal human plasma (NHP).

[66] The polypeptide for use according to any one of the preceding embodiments, wherein the MRT of the polypeptide is increased, in particular, at least 25% higher, at least 50% higher, at least 75% higher or at least 100% higher when compared to the MRT of endogenous VWF and/or when compared to the MRT of VWF of normal human plasma (NHP).

[67] The polypeptide for use according to any one of the preceding embodiments, wherein the MRT and/or plasma half-life of the polypeptide is increased when compared to that of a reference polypeptide which is identical to said polypeptide except that the reference polypeptide lacks the half-life extending moiety.

[68] The polypeptide for use according to any one of the preceding embodiments, wherein the polypeptide increases the maximal concentration ($C_{max}$) of endogenous Factor VIII as compared to untreated subjects.

[69] The polypeptide for use according to embodiment [68], wherein following administration of said polypeptide, the $C_{max}$ for FVIII amounts to at least 10 mIU/mL, at least 25 mIU/mL, at least 50 mIU/mL, at least 100 mIU/mL, at least 200 mIU/mL, at least 300 mIU/mL or at least 400 mIU/mL.

[70] The polypeptide for use according to any one of the preceding embodiments, wherein the polypeptide increases the peak area under the plasma concentration-time curve from zero to the last measured timepoint (AUC) of endogenous Factor VIII as compared to untreated subjects.

[71] The polypeptide for use according to embodiment [70], wherein following administration of the polypeptide, the AUC for the endogenous FVIII is increased to a level of at least 1000 mIU*h/mL, at least 2000 mIU*h/mL, at least 3000 mIU*h/mL, at least 5000 mIU*h/mL, at least 10000 mIU*h/mL or at least 20000 mIU*h/mL chromogenic FVIII activity.

[72] The polypeptide for use according to any one of the preceding embodiments, wherein at least one amino acid of the polypeptide is substituted as compared to the amino acid sequence of the wild-type VWF, wherein the binding affinity of such a modified polypeptide to FVIII is being further increased by introduction of said at least one substitution compared to the binding affinity of a reference polypeptide which has the same amino acid sequence except for said modifications.

[73] The polypeptide for use according to embodiment [72], wherein said at least one substitution within the truncated VWF has the capacity to further increase the half-life of endogenous FVIII following administration of the polypeptide and/or may allow for reduction of the to be administered dose of the recombinant polypeptide.

[74] The polypeptide for use according to any one of embodiments [72] to [73], wherein the substitutions are selected from the group of combinations consisting of S764G/S766Y, S764P/S7661, S764P/S766M, S764V/S766Y, S764E/S766Y, S764Y/S766Y, S764L/S766Y, S764P/S766W, S766W/S806A, S766Y/P769K, S766Y/P769N, S766Y/P769R, S764P/S766L, and S764E/S766Y/V1083A, referring to the sequence of SEQ ID NO:4 with regard to the amino acid numbering.

[75] The polypeptide for use according to embodiment [74], wherein said substitution is either the combination S764E/S766Y or S764E/S766Y/V1083A.

[76] The polypeptide for use according to any one of the preceding embodiments, wherein said polypeptide is administered extravascularly, in particular subcutaneously, and following administration the polypeptide exhibits a bioavailability of at least 20%, preferably of at least 30%, of at least 40%, of at least 50%, of at least 60%, of at least 70% or of at least 80%.

[77] The polypeptide for use according to any one of the preceding embodiments, wherein following administration of the polypeptide an increase of the subject's endogenous FVIII activity level is achieved, preferably the endogenous FVIII activity level is increased up to the physiological FVIII level (100%=1 IU/mL) or not substantially increased above the physiological FVIII level following administration of the polypeptide, preferably resulting in an increase of endogenous FVIII activity level not exceeding 300%=3 IU/mL, more preferably not exceeding 250%=2.5 IU/mL, not exceeding 200%=2 IU/mL, not exceeding 150%=1.5 IU/mL or not exceeding 120%=1.2 IU/mL of mean FVIII activity level in plasma of normal human plasma, respectively.

[78] The polypeptide for use according to any one of the preceding embodiments, wherein following administration of the polypeptide to the subject suffering from a blood coagulation disorder an increased thrombogenic risk is prevented.

[79] The polypeptide for use according to embodiment [78], wherein the prevention of a thrombogenic risk is determined or achieved by only a limited increase of endogenous FVIII activity level in the subject following administration of the polypeptide, preferably the endogenous FVIII activity level is increased up to the physiological FVIII level (100%=1 IU/mL) or not substantially increased above the physiological FVIII level following administration of the polypeptide, preferably resulting in an increase of endogenous FVIII activity level not exceeding 300%=3 IU/mL, more preferably not exceeding 250%=2.5 IU/mL, not exceeding 200%=2 IU/mL, not exceeding 150%=1.5 IU/mL or not exceeding 120%=1.2 IU/mL of mean FVIII activity level in plasma of normal human plasma, respectively.

[80] The polypeptide for use according to any one of the preceding embodiments, wherein following administration of said polypeptide the maximal concentration ($C_{max}$) for the polypeptide is at least 20 nmol/kg, at least 40 nmol/kg, at least 60 nmol/kg, at least 80 nmol/kg or at least 160 nmol/kg.

[81] The polypeptide for use according to any one of the preceding embodiments, wherein following administration of said polypeptide the area under the concentration over time curve from t=0 to t=∞ ($AUC_{0-inf}$) for the administered polypeptide is at least 2 nmol*h/mL, at least 3 nmol*h/mL, at least 4 nmol*h/mL, at least 20 nmol*h/mL, at least 40 nmol*h/mL, or at least 80 nmol*h/mL.

[82] The polypeptide for use according to any one of the preceding embodiments, wherein following administration of said polypeptide the clearance (CL) value for the polypeptide is reduced by a factor of at least 2, at least 5, or at least 10, as compared to a reference treatment, wherein said reference treatment is identical to said treatment, except that the polypeptide to be administered does not comprise a half-life extending moiety.

[83] The polypeptide for use according to any one of the preceding embodiments, wherein the polypeptide is administered at an amount of at least 0.01 mg/kg, at least 0.1 mg/kg, at least 0.2 mg/kg, at least 0.5 mg/kg, at least 1 mg/kg or at least 3 mg/kg polypeptide.

[84] The polypeptide for use according to any one of the preceding embodiments, wherein the recombinant polypeptide is administered with an amount not exceeding 20 mg/kg, not exceeding 15 mg/kg, not exceeding 10 mg/kg, or not exceeding 5 mg/kg of the polypeptide.

[85] The polypeptide for use according to any one of the preceding embodiments, wherein following administration of the polypeptide physiological activated partial thrombin time (aPTT) values are achieved, in particular, pathological aPTT values are reduced to physiological values.

[86] The polypeptide for use according to embodiment [85], wherein following administration of the polypeptide the activated partial thrombin time (aPTT) is reduced by a factor of at least 1.5, at least 2, at least 2.5, at least 3, at least 4, at least 5 or at least 10.

[87] The polypeptide for use according to any one of the preceding embodiments, wherein the polypeptide is administered repeatedly, preferably with a dosing of once monthly, once every third week, once every second week, once every seven days, twice per week or once every second day.

[88] The polypeptide for use according to embodiment [87], wherein following said repeated, i.e. multiple, administration of the polypeptide, a steady state level of endogenous FVIII activity level in the subject is achieved, wherein the steady state FVIII activity level preferably provides a trough level of above 1%, preferably a trough level of above 5%, preferably a trough level of above 10%, more preferably a trough level of above 20%, more preferably a trough level of above 50% and even most preferably the steady state FVIII activity level is essentially within a range of the physiological FVIII activity level.

[89] The polypeptide for use according to any one of embodiment [87] to [88], wherein following said repeated, i.e. multiple, administration a sustained reduction of activated partial thrombin time (aPTT) is achieved in the subject, wherein the aPTT preferably is essentially within a physiological range for aPTT.

[90] A method of treating a blood coagulation disorder, comprising administering to a patient an effective amount of a polypeptide as defined in any one of embodiments [1] to [89] without co-administering FVIII, said patient having endogenous Factor VIII (FVIII), wherein the activity level of endogenous FVIII in said patient before treatment with said polypeptide is reduced relative to the activity level of FVIII in normal human plasma (NHP) provided that the activity level of endogenous FVIII in said patient is at least 0.5% of the activity level of endogenous FVIII in normal human plasma (NHP) and whereby the endogenous FVIII level is increased following administration of said polypeptide. Said polypeptide is preferably either administered for prophylactic prevention of a bleeding event, wherein said treatment does not comprise co-administration of exogenous FVIII or said polypeptide is co-administered together with exogenous FVIII for the treatment of a bleeding event or for initiation of a prophylactic treatment regime, wherein for follow-up treatments said polypeptide is administered without co-administration of exogenous FVIII.

[91] A method of treating a blood coagulation disorder, comprising administering to a patient an effective amount of a polypeptide as defined in any one of embodiments [1] to [89], said patient having endogenous Factor VIII (FVIII), wherein the activity level of endogenous FVIII in said patient before treatment with said polypeptide is reduced relative to the activity level of FVIII in normal human plasma (NHP) provided that the activity level of endogenous FVIII in said patient is at least 0.5% of the activity level of endogenous FVIII in normal human plasma (NHP) and whereby the endogenous FVIII level is increased following administration of said polypeptide. Said treatment comprising that an exogenous FVIII is administered and thereby providing for the endogenous FVIII in said subject. Said polypeptide is preferably administered for prophylactic prevention of a bleeding event. According to a preferred embodiment, the polypeptide is administered subcutaneously and the FVIII is administered intravenously.

BRIEF DESCRIPTION OF THE DRAWINGS

FIG. 7A-2 shows rD'D3-FP exposure quantified in VWF ko and CD rats via its albumin component after i.v. or s.c. administration of rD'D3-FP, as described in Example 1.7 , and data is given as mean±SD for n=2-4 rats per timepoint. The dotted line represents the detection limit for rD'D3-FP.

FIG. 7A-3 shows rD'D3-FP exposure quantified in pigs via its albumin component after i.v. or s.c. administration of rD'D3-FP, as described in Example 1.7 , and data is given as mean±SD for n=1-3 pigs per timepoint. The dashed line represents the detection limit for rD'D3-FP.

FIG. 7B-1 shows FVIII exposure quantified as chromogenic FVIII activity in VWF ko rats after i.v. or s.c. administration of rD'D3-FP, as described in Example 1.7 , and data is given as mean±SD for n=2-4 rats per timepoint. The dotted lines represent the minimum and maximum of data from untreated healthy CD rats.

FIG. 7B-2 shows FVIII exposure quantified as chromogenic FVIII activity in pigs after i.v. or s.c. administration of rD'D3-FP, as described in Example 1.7 , and data is given as mean±SD for n=2-3 pigs per timepoint. The dotted lines represent the range coming from predose values from pigs.

FIG. 9 shows rD'D3-FP exposure in FVIII ko rats after i.v. or/and or combined with after s.c. administration of rD'D3-FP, as described in Example 1.9

DETAILED DESCRIPTION

Figure 1A:
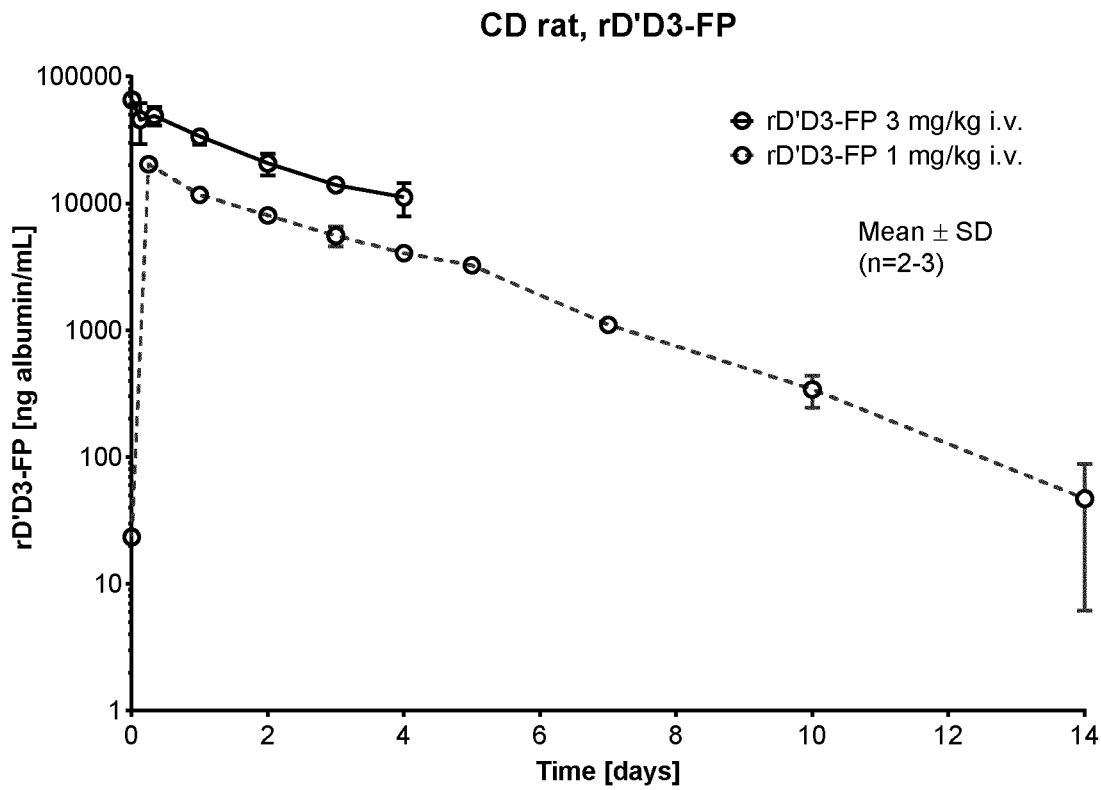
FIG. 1A shows rD'D3-FP exposure quantified via its albumin component in CD rats after i.v. administration of rD'D3-FP, as described in Example 1.1, and data is given as mean±SD for n=2-3 rats per timepoint.

In a first aspect, the present invention relates to a polypeptide comprising (i) a truncated von Willebrand Factor (VWF) and (ii) a half-life extending moiety, for use in the treatment of a blood coagulation disorder, said treatment comprising administering the polypeptide to a subject suffering from a blood coagulation disorder and having endogenous Factor VIII (FVIII), wherein the activity level of endogenous FVIII in said subject before treatment with said polypeptide is reduced relative to the activity level of FVIII in normal human plasma (NHP) provided that the activity level of endogenous FVIII in said subject is at least 0.5% of the activity level of endogenous FVIII in normal human plasma (NHP), and whereby the endogenous FVIII level is increased following administration of said polypeptide and said polypeptide is administered for prophylactic prevention of a bleeding event, wherein said treatment does not comprise co-administration of exogenous FVIII.

In a second aspect, the present invention pertains to a polypeptide comprising (i) a truncated von Willebrand Factor (VWF) and (ii) a half-life extending moiety, for use in the treatment of a blood coagulation disorder, said treatment comprising administering the polypeptide to a subject suffering from a blood coagulation disorder and having endogenous Factor VIII (FVIII), wherein the activity level of endogenous FVIII in said subject before treatment with said polypeptide is reduced relative to the activity level of FVIII in normal human plasma (NHP) provided that the activity level of endogenous FVIII in said subject is at least 0.5% of the activity level of endogenous FVIII in normal human plasma (NHP) and whereby the endogenous FVIII level is increased following administration of said polypeptide and wherein said polypeptide is co-administered together with exogenous FVIII for the treatment of a bleeding event or for initiation of a prophylactic treatment regime, wherein for follow-up treatments said polypeptide is administered without co-administration of exogenous FVIII.

A third aspect pertains to a pharmaceutical composition comprising a polypeptide comprising (i) a truncated von Willebrand Factor (VWF) and (ii) a half-life extending moiety, for use in the treatment of a blood coagulation disorder, said treatment comprising administering the polypeptide to a subject suffering from a blood coagulation disorder and having endogenous Factor VIII (FVIII), wherein the activity level of endogenous FVIII in said subject before treatment with said polypeptide is reduced relative to the activity level of FVIII in normal human plasma (NHP) provided that the activity level of endogenous FVIII in said subject is at least 0.5% of the activity level of endogenous FVIII in normal human plasma (NHP), and whereby the endogenous FVIII level is increased following administration of said polypeptide and said polypeptide is administered for prophylactic prevention of a bleeding event, wherein said treatment does not comprise co-administration of exogenous FVIII.

A fourth aspect pertains to a pharmaceutical composition comprising a polypeptide comprising (i) a truncated von Willebrand Factor (VWF) and (ii) a half-life extending moiety, for use in the treatment of a blood coagulation disorder, said treatment comprising administering the polypeptide to a subject suffering from a blood coagulation disorder and having endogenous Factor VIII (FVIII), wherein the activity level of endogenous FVIII in said subject before treatment with said polypeptide is reduced relative to the activity level of FVIII in normal human plasma (NHP) provided that the activity level of endogenous FVIII in said subject is at least 0.5% of the activity level of endogenous FVIII in normal human plasma (NHP) and whereby the endogenous FVIII level is increased following administration of said polypeptide and wherein said polypeptide is co-administered together with exogenous FVIII for the treatment of a bleeding event or for initiation of a prophylactic treatment regime, wherein for follow-up treatments said polypeptide is administered without co-administration of exogenous FVIII.

A fifth aspect pertains to use of a recombinant polypeptide comprising (i) a truncated von Willebrand Factor (VWF) and (ii) a half-life extending moiety for the manufacture of a medicament for the treatment of a blood coagulation disorder, said treatment comprising administering the polypeptide to a subject suffering from a blood coagulation disorder and having endogenous Factor VIII (FVIII), wherein the activity level of endogenous FVIII in said subject before treatment with said polypeptide is reduced relative to the activity level of FVIII in normal human plasma (NHP) provided that the activity level of endogenous FVIII in said subject is at least 0.5% of the activity level of endogenous FVIII in normal human plasma (NHP), and whereby the endogenous FVIII level is increased following administration of said polypeptide and wherein said polypeptide is either administered for prophylactic prevention of a bleeding event, wherein said treatment does not comprise co-administration of exogenous FVIII or said polypeptide is co-administered together with exogenous FVIII for the treatment of a bleeding event or for initiation of a prophylactic treatment regime, wherein for follow-up treatments said polypeptide is administered without co-administration of exogenous FVIII.

The polypeptide comprising a truncated von Willebrand Factor (VWF) and a half-life extending moiety will be referred to herein as "polypeptide of the invention".

The Truncated VWF

The term "von Willebrand Factor" (VWF) as used herein includes naturally occurring (native) VWF, but also variants thereof retaining at least the FVIII binding activity of naturally occurring VWF, e.g. sequence variants where one or more residues have been inserted, deleted or substituted. The FVIII binding activity is determined by a FVIII-VWF binding assay as described in Example 2.

The VWF in accordance with this invention is human VWF represented by the amino acid sequence shown in SEQ ID NO:4, and preferably is a truncated VWF. The cDNA encoding SEQ ID NO:4 is shown in SEQ ID NO:3.

The gene encoding human native VWF is transcribed into a 9 kb mRNA which is translated into a pre-propolypeptide of 2813 amino acids with an estimated molecular weight of 310,000 Da. The pre-propolypeptide contains an N-terminal 22 amino acids signal peptide, followed by a 741 amino acid pro-polypeptide (amino acids 23-763 of SEQ ID NO:4) and the mature subunit (amino acids 764-2813 of SEQ ID NO:4). Cleavage of the 741 amino acids propolypeptide from the N-terminus results in mature VWF consisting of 2050 amino acids. The amino acid sequence of the human native VWF pre-propolypeptide is shown in SEQ ID NO:4. Unless indicated otherwise, the amino acid numbering of VWF residues in this application refers to SEQ ID NO:4, even if the VWF molecule does not comprise all residues of SEQ ID NO:4.

The propolypeptide of native VWF comprises multiple domains. Different domain annotations can be found in the literature (see, e.g. Zhou et al. (2012) Blood 120(2): 449-458). The following domain annotation of native pre-propolypeptide of VWF is applied in this application:

D1-D2-D'-D3-A1-A2-A3-D4-C1-C2-C3-C4-C5-C6-CK

With reference to SEQ ID NO:4, the D' domain consists of amino acids 764-865; and the D3 domain consists of amino acids 866-1242.

The feature "truncated" means that the polypeptide does not comprise the entire amino acid sequence of mature VWF (amino acids 764-2813 of SEQ ID NO:4). Typically, the truncated VWF does not comprise all amino acids 764-2813 of SEQ ID NO:4 but only a fragment thereof. A truncated VWF may also be referred to as a VWF fragment, or in the plural as VWF fragments.

Typically, the truncated VWF is capable of binding to a Factor VIII. Preferably, the truncated VWF is capable of binding to the mature form of human native Factor VIII. The truncated VWF is capable of binding to endogenous and/or exogenous Factor VIII. In certain embodiments, the truncated VWF is capable of binding to a co-administered recombinant FVIII, preferably to a FVIII as described herein, more preferred to a single-chain Factor VIII consisting of the amino acid sequence SEQ ID NO:5. Binding of the truncated VWF to Factor VIII can be determined by a FVIII-VWF binding assay as described in Example 2.

The truncated VWF of the present invention preferably comprises or consists of an amino acid sequence having a sequence identity of at least 90% to amino acids 776 to 805 of SEQ ID NO:4 and is capable of binding to FVIII. In preferred embodiments the truncated VWF comprises or consists of an amino acid sequence having a sequence identity of at least 95%, at least 96%, at least 97%, at least 98%, or at least 99%, to amino acids 776 to 805 of SEQ ID NO:4 and is capable of binding to FVIII. Most preferably, the truncated VWF comprises or consists of amino acids 776 to 805 of SEQ ID NO:4. Unless indicated otherwise herein, sequence identities are determined over the entire length of the reference sequence (e.g. amino acids 776 to 805 of SEQ ID NO:4).

The truncated VWF of the present invention preferably comprises or consists of an amino acid sequence having a sequence identity of at least 90% to amino acids 766 to 864 of SEQ ID NO:4 and is capable of binding to FVIII. In preferred embodiments the truncated VWF comprises or consists of an amino acid sequence having a sequence identity of at least 95%, at least 96%, at least 97%, at least 98%, or at least 99%, to amino acids 766 to 864 of SEQ ID NO:4 and is capable of binding to FVIII. Most preferably, the truncated VWF comprises or consists of amino acids 766 to 864 of SEQ ID NO:4.

In another preferred embodiment, the truncated VWF consists of (a) an amino acid sequence having a sequence identity of at least 90% to amino acids 764 to 1242 of SEQ ID NO:4, or (b) a fragment thereof, provided that the truncated VWF is still capable of binding to FVIII. More preferably, the truncated VWF consists of (a) an amino acid sequence having a sequence identity of at least 95%, at least 96%, at least 97%, at least 98%, or at least 99%, to amino acids 764 to 1242 of SEQ ID NO:4, or (b) a fragment thereof, provided that the truncated VWF is still capable of binding to FVIII. Most preferably, the truncated VWF consists of (a) amino acids 764 to 1242 of SEQ ID NO:4, or (b) a fragment thereof, provided that the truncated VWF is still capable of binding to FVIII.

As described in more detail below, the polypeptide may be prepared by a method which uses cells comprising a nucleic acid encoding the polypeptide comprising the truncated VWF. The nucleic acid is introduced into suitable host cells by techniques that are known per se.

In a preferred embodiment, the nucleic acid in the host cell encodes (a) an amino acid sequence having a sequence identity of at least 90% to amino acids 1 to 1242 of SEQ ID NO:4, or (b) a fragment thereof, provided that the truncated mature VWF is still capable of binding to FVIII. More preferably, the nucleic acid encodes (a) an amino acid sequence having a sequence identity of at least 95%, at least 96%, at least 97%, at least 98%, or at least 99%, to amino acids 1 to 1242 of SEQ ID NO:4, or (b) a fragment thereof, provided that the truncated VWF is still capable of binding to FVIII. Most preferably, the nucleic acid encodes (a) amino acids 1 to 1242 of SEQ ID NO:4, or (b) a fragment thereof, provided that the truncated VWF is still capable of binding to FVIII. Especially if the polypeptide in accordance with this invention is a dimer, the nucleic acid will comprise a sequence encoding amino acids 1 to 763 of VWF (e.g. SEQ ID NO:4), even if the truncated VWF in the polypeptide does not comprise amino acids 1 to 763 of VWF (e.g. SEQ ID NO:4).

In other embodiments the truncated VWF comprises or consists of one of the following amino acid sequences, each referring to SEQ ID NO:4:

776-805; 766-805; 764-805; 776-810; 766-810; 764-810; 776-815; 766-815; 764-815;
776-820; 766-820; 764-820; 776-825; 766-825; 764-825; 776-830; 766-830; 764-830;
776-835; 766-835; 764-835; 776-840; 766-840; 764-840; 776-845; 766-845; 764-845;
776-850; 766-850; 764-850; 776-855; 766-855; 764-855; 776-860; 766-860; 764-860;
776-864; 766-864; 764-864; 776-865; 766-865; 764-865; 776-870; 766-870; 764-870;
776-875; 766-875; 764-875; 776-880; 766-880; 764-880; 776-885; 766-885; 764-885;
776-890; 766-890; 764-890; 776-895; 766-895; 764-895; 776-900; 766-900; 764-900;
776-905; 766-905; 764-905; 776-910; 766-910; 764-910; 776-915; 766-915; 764-915;
776-920; 766-920; 764-920; 776-925; 766-925; 764-925; 776-930; 766-930; 764-930;
776-935; 766-935; 764-935; 776-940; 766-940; 764-940; 776-945; 766-945; 764-945;
776-950; 766-950; 764-950; 776-955; 766-955; 764-955; 776-960; 766-960; 764-960;
776-965; 766-965; 764-965; 776-970; 766-970; 764-970; 776-975; 766-975; 764-975;
776-980; 766-980; 764-980; 776-985; 766-985; 764-985; 776-990; 766-990; 764-990;
776-995; 766-995; 764-995; 776-1000; 766-1000; 764-1000; 776-1005; 766-1005; 764-1005;
776-1010; 766-1010; 764-1010; 776-1015; 766-1015; 764-1015; 776-1020; 766-1020; 764-1020;
776-1025; 766-1025; 764-1025; 776-1030; 766-1030; 764-1030; 776-1035; 766-1035; 764-1035;
776-1040; 766-1040; 764-1040; 776-1045; 766-1045; 764-1045; 776-1050; 766-1050; 764-1050;
776-1055; 766-1055; 764-1055; 776-1060; 766-1060; 764-1060; 776-1065; 766-1065; 764-1065;
776-1070; 766-1070; 764-1070; 776-1075; 766-1075; 764-1075; 776-1080; 766-1080; 764-1080;
776-1085; 766-1085; 764-1085; 776-1090; 766-1090; 764-1090; 776-1095; 766-1095; 764-1095;
776-1100; 766-1100; 764-1100; 776-1105; 766-1105; 764-1105; 776-1110; 766-1110; 764-1110;
776-1115; 766-1115; 764-1115; 776-1120; 766-1120; 764-1120; 776-1125; 766-1125; 764-1125;
776-1130; 766-1130; 764-1130; 776-1135; 766-1135; 764-1135; 776-1140; 766-1140; 764-1140;
776-1145; 766-1145; 764-1145; 776-1150; 766-1150; 764-1150; 776-1155; 766-1155; 764-1155;
776-1160; 766-1160; 764-1160; 776-1165; 766-1165; 764-1165; 776-1170; 766-1170; 764-1170;
776-1175; 766-1175; 764-1175; 776-1180; 766-1180; 764-1180; 776-1185; 766-1185; 764-1185;
776-1190; 766-1190; 764-1190; 776-1195; 766-1195; 764-1195; 776-1200; 766-1200; 764-1200;
776-1205; 766-1205; 764-1205; 776-1210; 766-1210; 764-1210; 776-1215; 766-1215; 764-1215;
776-1220; 766-1220; 764-1220; 776-1225; 766-1225; 764-1225; 776-1230; 766-1230; 764-1230;
776-1235; 766-1235; 764-1235; 776-1240; 766-1240; 764-1240; 776-1242; 766-1242; 764-1242;
764-1464; 764-1250; 764-1041; 764-828; 764-865; 764-1045; 764-1035; 764-1128; 764-1198;
764-1268; 764-1261; 764-1264; 764-1459; 764-1463; 764-1464; 764-1683; 764-1873; 764-1482;
764-1479; 764-1672; and 764-1874.

In certain embodiments the truncated VWF has an internal deletion relative to mature wild type VWF. For example, the A1, A2, A3, D4, C1, C2, C3, C4, C5, C6, CK domains or combinations thereof may be deleted, and the D' domain and/or the D3 domain is retained. In further embodiments the truncated VWF does not comprise the binding sites for platelet glycoprotein Ibα (GPIbα), collagen and/or integrin αIIbβIII (RGDS sequence within the C1 domain). In other embodiments, the truncated VWF does not comprise the cleavage site (Tyr1605-Met1606) for ADAMTS13 which is located at the central A2 domain of VWF. In yet another embodiment, the truncated VWF does not comprise the binding sites for GPIbα, and/or does not comprise the binding site for collagen, and/or does not comprise the binding site for integrin αIIbβIII, and/or it does not comprise the cleavage site (Tyr1605-Met1606) for ADAMTS13 which is located at the central A2 domain of VWF.

In other embodiments the truncated VWF comprises or consists of an amino acid sequence that has a sequence identity of at least 90%, or at least 91%, or at least 92%, or at least 93%, or at least 94%, or at least 95%, or at least 96%, or at least 97%, or at least 98%, or at least 99%, to one of the amino acid sequences recited in the preceding paragraph, provided that the truncated VWF is capable of binding to FVIII.

A polypeptide of the invention is termed a "dimer" in the present invention if two monomers of polypeptide of the invention are linked covalently. Preferably the two monomeric subunits are covalently linked via at least one disulfide bridge, e.g. by one, two, three or four disulfide bridges. The cysteine residues forming the at least one disulfide bridge are preferably located within the truncated VWF portion of the polypeptide of the invention. In one embodiment, these cysteine residues are Cys-1099, Cys-1142, Cys-1222, Cys-1225, or Cys-1227 or combinations thereof.

The dimer is preferably a homo-dimer, whereby each monomer comprises preferably a half-life extending moiety as disclosed herein. If the polypeptide of the invention is a dimer, the truncated VWF preferably comprises or consists of two polypeptides each with an amino acid sequence having a sequence identity of at least 90% to amino acids 764 to 1099, amino acids 764 to 1142, amino acids 764 to 1222, amino acids 764 to 1225, or amino acids 764 to 1227 of SEQ ID NO:4 and is capable of binding to FVIII. In preferred embodiments the truncated VWF comprises or consists of an amino acid sequence having a sequence identity of at least 95%, at least 96%, at least 97%, at least 98%, or at least 99%, to amino acids 764 to 1099, amino acids 764 to 1142, amino acids 764 to 1222, amino acids 764 to 1225, or amino acids 764 to 1227 of SEQ ID NO:4 and is capable of binding to FVIII. Most preferably, the truncated VWF comprises or consists of amino acids 764 to 1099, amino acids 764 to 1142, amino acids 764 to 1222, amino acids 764 to 1225, amino acids 764 to 1227 or amino acids 764 to 1242 of SEQ ID NO:4.

The truncated VWF may be any one of the VWF fragments disclosed in WO 2013/106787 A1, WO 2014/198699 A2, WO 2011/060242 A2 or WO 2013/093760 A2, the disclosure of which is incorporated herein by reference.

According to further preferred embodiments the truncated VWF as disclosed above may comprise at least one of the amino acid substitutions as disclosed in WO 2016/000039 A1. Those modified versions of the truncated VWF comprise at least one amino acid substitution within its D' domain, as compared to the amino acid sequence of the D' domain of wild-type VWF according to SEQ ID NO: 4. The amino acid sequence of the modified versions of the truncated VWF can have one or more amino acid substitutions relative to the respective wild type sequence. The amino acid sequence of the D' domain of the modified truncated VWF preferably has one or 2 amino acid substitutions relative to the D' domain of SEQ ID NO:4. It is preferred that S at position 764 of SEQ ID NO:4, corresponding to position 1 of SEQ ID NO:2, is substituted with an amino acid selected from the group consisting of G, P, V, E, Y, A and L. It is also preferred that S at position 766 of SEQ ID NO:4, corresponding to position 3 of SEQ ID NO:2 is substituted with an amino acid selected from the group consisting of Y, I, M, V, F, H, R and W. Preferred combinations of substitutions include S764G/S766Y, S764P/57661, S764P/S766M, S764V/S766Y, S764E/S766Y, S764Y/S766Y, S764L/S766Y, S764P/S766W, S766W/S806A, S766Y/P769K, S766Y/P769N, S766Y/P769R and S764P/S766L, referring to the sequence of SEQ ID NO:4. The binding affinity of the polypeptide of the present invention to FVIII may be further increased by introduction of said substitutions compared to the binding affinity of a reference polypeptide which has the same amino acid sequence except for said modifications. Said substitutions within the truncated VWF may contribute to further increase the half-life of endogenous FVIII or the half-life of co-administered FVIII and/or may allow for reduction of the dose of the recombinant polypeptide of the invention to be administered.

Half-Life Extending Moiety

The half-life of endogenous VWF in human plasma is about 16 h (Lenting P J, Christophe O D, Denis C V. von Willebrand factor biosynthesis, secretion, and clearance: connecting the far ends. Blood. 2015.125(13):2019-28).

In addition to the truncated VWF, the polypeptide of the invention further comprises a half-life extending moiety. The half-life-extending moiety may be a heterologous amino acid sequence fused to the truncated VWF. Alternatively, the half-life-extending moiety may be chemically conjugated to the polypeptide comprising the truncated VWF by a covalent bond different from a peptide bond.

In certain embodiments of the invention, the half-life of the polypeptide of the invention is extended by chemical modification, e.g. attachment of a half-life extending moiety such as polyethylene glycol (PEGylation), glycosylated PEG, hydroxyl ethyl starch (HESylation), polysialic acids, elastin-like polypeptides, heparosan polymers or hyaluronic acid. In another embodiment, the polypeptide of the invention is conjugated to a HLEP such as albumin via a chemical linker. The principle of this conjugation technology has been described in an exemplary manner by Conjuchem LLC (see, e.g., U.S. Pat. No. 7,256,253).

In other embodiments, the half-life-extending moiety is a half-life enhancing protein (HLEP). Preferably, the HLEP is an albumin or a fragment thereof. The N-terminus of the albumin may be fused to the C-terminus of the truncated VWF. Alternatively, the C-terminus of the albumin may be fused to the N-terminus of the truncated VWF. One or more HLEPs may be fused to the N- or C-terminal part of VWF provided that they do not to interfere with or abolish the binding capability of the truncated VWF to FVIII.

The recombinant polypeptide further comprises preferably a chemical bond or a linker sequence positioned between the truncated VWF and the HLEM.

Said linker sequence may be a peptidic linker consisting of one or more amino acids, in particular of 1 to 50, 1 to 30, 1 to 20, 1 to 15, 1 to 10, 1 to 5 or 1 to 3 (e.g. 1, 2 or 3) amino acids and which may be equal or different from each other. Preferrably, the linker sequence is not present at the corresponding position in the wild-type VWF. Preferred amino acids present in said linker sequence include Gly and Ser. The linker sequence should be non-immunogenic. Preferred linkers may be comprised of alternating glycine and serine residues. Suitable linkers are described for example in WO2007/090584.

In another embodiment of the invention the peptidic linker between the truncated VWF moiety and the HLEM consists of peptide sequences, which serve as natural interdomain linkers in human proteins. Preferably such peptide sequences in their natural environment are located close to the protein surface and are accessible to the immune system so that one can assume a natural tolerance against this sequence. Examples are given in WO 2007/090584. Cleavable linker sequences are described, e.g., in WO 2013/120939 A1.

In a preferred embodiment of the recombinant polypeptide the linker between the truncated VWF and the HLEM is a glycine/serine peptidic linker having or consisting of amino acid sequence 480-510 of SEQ ID NO:2.

In one embodiment the polypeptide has the following structure:

tVWF-L1-H,                     [formula 1]

Wherein tVWF is the truncated VWF, L1 is a chemical bond or a linker sequence, and H is a HLEP.

L1 may be a chemical bond or a linker sequence consisting of one or more amino acids, e.g. of 1 to 50, 1 to 30, 1 to 20, 1 to 15, 1 to 10, 1 to 5 or 1 to 3 (e.g. 1, 2 or 3) amino acids and which may be equal or different from each other.

Usually, the linker sequences are not present at the corresponding position in the wild-type VWF. Examples of suitable amino acids present in L1 include Gly and Ser. The linker should be non-immunogenic and may be a non-cleavable or cleavable linker. Non-cleavable linkers may be comprised of alternating glycine and serine residues as exemplified in WO2007/090584. In another embodiment of the invention the peptidic linker between the truncated VWF moiety and the albumin moiety consists of peptide sequences, which serve as natural interdomain linkers in human proteins. Preferably such peptide sequences in their natural environment are located close to the protein surface and are accessible to the immune system so that one can assume a natural tolerance against this sequence. Examples are given in WO2007/090584. Cleavable linker sequences are described, e.g., in WO 2013/120939 A1.

Preferred HLEP sequences are described infra. Likewise encompassed by the invention are fusions to the exact "N-terminal amino acid" or to the exact "C-terminal amino acid" of the respective HLEP, or fusions to the "N-terminal part" or "C-terminal part" of the respective HLEP, which includes N-terminal deletions of one or more amino acids of the HLEP. The polypeptide may comprise more than one HLEP sequence, e.g. two or three HLEP sequences. These multiple HLEP sequences may be fused to the C-terminal part of VWF in tandem, e.g. as successive repeats.

Half-Life Enhancing Polypeptides (HLEPs)

Preferably, the half-life extending moiety is a half-life extending polypeptide (HLEP), more preferably HLEP is selected from albumin or fragments thereof, immunoglobulin constant region and portions thereof, e.g. the Fc fragment, solvated random chains with large hydrodynamic volume (e.g. XTEN (Schellenberger et al. 2009; Nature Biotechnol. 27:1186-1190), homo-amino acid repeats (HAP) or proline-alanine-serine repeats (PAS), afamin, alpha-fetoprotein, Vitamin D binding protein, transferrin or variants thereof, carboxyl-terminal peptide (CTP) of human chorionic gonadotropin-1R subunit, polypeptides or lipids capable of binding under physiological conditions to albumin or immunoglobulin constant region.

A "half-life enhancing polypeptide" as used herein is preferably selected from the group consisting of albumin, a member of the albumin-family, the constant region of immunoglobulin G and fragments thereof, region and polypeptides capable of binding under physiological conditions to albumin, to members of the albumin family as well as to portions of an immunoglobulin constant region. It may be a full-length half-life-enhancing protein described herein (e.g. albumin, a member of the albumin-family or the constant region of immunoglobulin G) or one or more fragments thereof that are capable of stabilizing or prolonging the therapeutic activity or the biological activity of the coagulation factor. Such fragments may be of 10 or more amino acids in length or may include at least about 15, at least about 20, at least about 25, at least about 30, at least about 50, at least about 100, or more contiguous amino acids from the HLEP sequence or may include part or all of specific domains of the respective HLEP, as long as the HLEP fragment provides a functional half-life extension of at least 25% compared to the respective polypeptide without the HLEP.

The HLEP portion of the polypeptide of the invention may be a variant of a wild type HLEP. The term "variants" includes insertions, deletions and substitutions, either conservative or non-conservative, where such changes do not substantially alter the FVIII-binding activity of the truncated VWF.

In particular, the proposed VWF HLEP fusion constructs of the invention may include naturally occurring polymorphic variants of HLEPs and fragments of HLEPs. The HLEP may be derived from any vertebrate, especially any mammal, for example human, monkey, cow, sheep, or pig. Non-mammalian HLEPs include, but are not limited to, hen and salmon.

According to certain embodiments of present disclosure the half-life extending moiety, in particular a HLEP, portion of the polypeptide of the invention may be specified with the alternative term "FP". Preferably, the term "FP" represents a human albumin if not indicated otherwise.

According to certain preferred embodiments, the polypeptide is a fusion protein. A fusion protein in terms of present invention is a protein created by in-frame joining of at least two DNA sequences encoding the truncated VWF as well as the HLEP. The skilled person understands that translation of the fusion protein DNA sequence will result in a single protein sequence. As a result of an in frame insertion of a DNA sequence encoding a peptidic linker according to a further preferred embodiment, a fusion protein comprising the truncated VWF, a suitable linker and the HLEP may be obtained.

Albumin as HLEP

The terms, "human serum albumin" (HSA) and "human albumin" (HA) and "albumin" (ALB) are used interchangeably in this application. The terms "albumin" and "serum albumin" are broader, and encompass human serum albumin (and fragments and variants thereof) as well as albumin from other species (and fragments and variants thereof).

As used herein, "albumin" refers collectively to albumin polypeptide or amino acid sequence, or an albumin fragment or variant, having one or more functional activities (e.g., biological activities) of albumin. In particular, "albumin" refers to human albumin or fragments thereof, especially the mature form of human albumin as shown in SEQ ID NO:6 herein or albumin from other vertebrates or fragments thereof, or analogs or variants of these molecules or fragments thereof.

According to certain embodiments of present disclosure the alternative term "FP" is used to identify the HLEP, in particular to define albumin as HLEP.

In particular, the proposed polypeptides of the invention may include naturally occurring polymorphic variants of human albumin and fragments of human albumin. Generally speaking, an albumin fragment or variant will be at least 10, preferably at least 40, most preferably more than 70 amino acids long.

Preferred embodiments of the invention include albumin variants used as a HLEP of the polypeptide of the invention with enhanced binding to the FcRn receptor. Such albumin variants may lead to a longer plasma half-life of a truncated VWF albumin variant fusion protein as compared to a truncated VWF fusion with a wild-type albumin.

The albumin portion of the polypeptides of the invention may comprise at least one subdomain or domain of HA or conservative modifications thereof.

Immunoglobulins as HLEPs

Immunoglobulin G (IgG) constant regions (Fc) are known in the art to increase the half-life of therapeutic proteins (Dumont J A et al. 2006. BioDrugs 20:151-160). The IgG constant region of the heavy chain consists of 3 domains (CH1-CH3) and a hinge region. The immunoglobulin sequence may be derived from any mammal, or from subclasses IgG1, IgG2, IgG3 or IgG4, respectively. IgG and IgG fragments without an antigen-binding domain may also be used as HLEPs. The therapeutic polypeptide portion is connected to the IgG or the IgG fragments preferably via the hinge region of the antibody or a peptidic linker, which may even be cleavable. Several patents and patent applications describe the fusion of therapeutic proteins to immunoglobulin constant regions to enhance the therapeutic protein's in vivo half-lives. US 2004/0087778 and WO 2005/001025 describe fusion proteins of Fc domains or at least portions of immunoglobulin constant regions with biologically active peptides that increase the half-life of the peptide, which otherwise would be quickly eliminated in vivo. Fc-IFN-β fusion proteins were described that achieved enhanced biological activity, prolonged circulating half-life and greater solubility (WO 2006/000448). Fc-EPO proteins with a prolonged serum half-life and increased in vivo potency were disclosed (WO 2005/063808) as well as Fc fusions with G-CSF (WO 2003/076567), glucagon-like peptide-1 (WO 2005/000892), clotting factors (WO 2004/101740) and interleukin-10 (U.S. Pat. No. 6,403,077), all with half-life enhancing properties.

Various HLEPs which can be used in accordance with this invention are described in detail in WO 2013/120939 A1.

N-Glycans and Sialylation of the Polypeptide of the Invention

The polypeptide of the invention preferably comprises N-glycans, and at least 75%, preferably at least 85%, more preferably at least 90% of said N-glycans comprise, on average, at least one sialic acid moiety. In preferred embodiments, at least 91%, at least 92%, at least 93%, at least 94%, at least 95%, at least 96%, at least 97%, at least 98%, or at least 99%, of said N-glycans comprise, on average, at least one sialic acid moiety. The inventors found that polypeptides comprising highly sialylated VWF fragments not only have a prolonged half-life themselves, but are also capable to extend the half-life of co-administered FVIII further. In other words, administration of the polypeptide of the invention leads to an extended half-life and/or to a reduced clearance of co-administered FVIII.

The polypeptide of the invention preferably comprises N-glycans, and at least 50% of the sialyl groups of the N-glycans of the glycoproteins are α-2,6-linked sialyl groups. In general, terminal sialyl groups can be attached to the galactose groups via a α-2,3- or via a α-2,6-linkage. Typically, N-glycans of the polypeptide of the invention comprise more α-2,6-linked sialyl groups than α-2,3-linked sialyl groups. Preferably, at least 60%, or at least 70%, or at least 80%, or at least 90% of the sialyl groups of the N-glycans are α-2,6-linked sialyl groups. These embodiments can be obtained by, e.g., co-expressing human α-2,6-sialyltransferase in mammalian cells.

In one embodiment, at least 85%, at least 90%, at least 95%, at least 96%, at least 97%, at least 98%, or at least 99%, of the N-glycans of the polypeptide of the invention comprise at least one sialic acid group. In another embodiment, at least 90%, at least 95%, at least 96%, at least 97%, at least 98%, or at least 99%, of the N-glycans of the polypeptide of the invention comprise at least one sialic acid group.

In another embodiment, less than 15%, less than 12%, less than 10%, or less than 8%, or less than 6%, or less than 5%, or less than 4%, or less than 3%, or less than 2% or even less than 1% of the N-glycans of the polypeptide of the invention are asialo-N-glycans, i.e. they are N-glycans lacking a sialic acid group. In another embodiment, less than 15%, less than 12%, less than 10%, or less than 8%, or less than 6%, or less than 5%, or less than 4%, or less than 3%, or less than 2% or even less than 1% of the N-glycans of the polypeptide of the invention are asialo-N-glycans, i.e. they do not have a sialic acid group.

Suitable methods of producing such glycoproteins are described in pending PCT/EP2016/061440. Accordingly, a method of producing a glycoprotein comprising N-glycans with increased sialylation is described therein, which method comprises (i) providing cells comprising a nucleic acid encoding a polypeptide comprising a truncated von Willebrand Factor (VWF), and (ii) culturing said cells at a temperature of less than 36.0° C. In addition, a method of producing a dimer of a glycoprotein comprising a truncated von Willebrand Factor (VWF), or for increasing the dimerization of said glycoprotein is described, which method comprises (i) providing cells comprising a nucleic acid encoding the amino acid sequence of the glycoprotein, and (ii) culturing said cells at a temperature of less than 36.0° C. Further, a method of producing a glycoprotein comprising N-glycans with increased sialylation is described therein, which comprises (i) providing cells comprising a nucleic acid encoding a polypeptide comprising a truncated von Willebrand Factor (VWF) and a recombinant nucleic acid encoding an α-2,6-sialyltransferase, and (ii) culturing the cells under conditions that allow expression of the glycoprotein and of the α-2,6-sialyltransferase.

The above-described embodiments can be combined with each other. Any percentages of N-glycans mentioned above, or any indications of the degree of sialylation, are to be understood as average percentages or degrees, i.e. they refer to a population of molecules, not to a single molecule. It is clear that the glycosylation or sialylation of the individual glycoprotein molecules within a population of glycoproteins will show some heterogeneity.

Dimers

The polypeptides of this invention have preferably a high proportion of dimers. The polypeptide of the invention is therefore preferably present as dimer. The polypeptide of the invention is therefore preferably present as dimer. In one embodiment, at least 50%, or at least 60%, or at least 70% of the polypeptides are present as dimers. In another embodiment, the ratio dimer:monomer of the polypeptide of the invention is at least 1.5, preferably at least 2, more preferably at least 2.5 or at least 3. Most preferably all polypeptides of the invention are present as dimers. The use of dimers is favorable, as the dimer has an improved affinity to Factor VIII as compared to the monomer. The dimer content, and the ratio of dimer to monomer of the polypeptide of the invention can be determined as described in the Examples.

In one embodiment, the affinity of the polypeptide of the invention to Factor VIII is greater than that of human native VWF to the same Factor VIII molecule. The factor VIII affinity may refer to human native Factor VIII, or to the Factor VIII molecule characterized by SEQ ID NO:5.

It has been found that preparations of the polypeptide of this invention with a high proportion of dimers do have an increased affinity to Factor VIII. Such increased affinity to Factor VIII does lead to an enhanced stabilization of Factor VIII by the polypeptides of the present invention. Alternatively to or in combination with an increased dimer proportion also polypeptides in accordance with the invention with mutations within the Factor VIII binding domain which do increase the affinity to Factor VIII are preferred embodiments of the invention. Suitable mutations are disclosed, e.g., in WO 2013/120939 A1.

Preparation of the Polypeptide

The nucleic acid encoding the polypeptide of the invention can be prepared according to methods known in the art. Based on the cDNA sequence of VWF (SEQ ID NO:3), recombinant DNA encoding the above-mentioned truncated VWF constructs or polypeptides of the invention can be designed and generated.

Even if the polypeptide which is secreted by the host cells does not comprise amino acids 1 to 763 of VWF, it is preferred that the nucleic acid (e.g. the DNA) encoding the intracellular precursor of the polypeptide comprises a nucleotide sequence encoding an amino acid sequence having a sequence identity of at least 95%, at least 96%, at least 97%, at least 98%, or at least 99%, to amino acids 23 to 763 or preferably to amino acids 1 to 763 of SEQ ID NO:4. Most preferably, the nucleic acid (e.g. the DNA) encoding the intracellular precursor of the polypeptide comprises a nucleotide sequence encoding amino acids 23 to 763 of SEQ ID NO:4, or amino acids 1 to 763 of SEQ ID NO:4.

Constructs in which the DNA contains the entire open reading frame inserted in the correct orientation into an expression plasmid may be used for protein expression. Typical expression vectors contain promoters that direct the synthesis of large amounts of mRNA corresponding to the inserted nucleic acid in the plasmid-bearing cells. They may also include an origin of replication sequence allowing for their autonomous replication within the host organism, and sequences that increase the efficiency with which the synthesized mRNA is translated. Stable long-term vectors may be maintained as freely replicating entities by using regulatory elements of, for example, viruses (e.g., the OriP sequences from the Epstein Barr Virus genome). Cell lines may also be produced that have integrated the vector into the genomic DNA, and in this manner the gene product is produced on a continuous basis.

Typically, the cells to be provided are obtained by introducing the nucleic acid encoding a polypeptide of the invention into mammalian host cells.

Any host cell susceptible to cell culture, and to expression of glycoproteins, may be utilized in accordance with the present invention. In certain embodiments, a host cell is mammalian. Non-limiting examples of mammalian cells that may be used in accordance with the present invention include BALB/c mouse myeloma line (NSO/1, ECACC No: 85110503); human retinoblasts (PER.C6 (CruCell, Leiden, The Netherlands)); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); baby hamster kidney cells (BHK, ATCC CCL10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243 251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (HepG2, HB 8065); mouse mammary tumor (MMT 060562, ATCC CCL51); TRI cells (Mather et al., Annals NY. Acad. Sci., 383:44-68, 1982); MRC 5 cells; PS4 cells; human amniocyte cells (CAP); and a human hepatoma line (Hep G2). Preferably, the cell line is a rodent cell line, especially a hamster cell line such as CHO or BHK.

Methods suitable for introducing nucleic acids sufficient to achieve expression of a glycoprotein of interest into mammalian host cells are known in the art. See, for example, Gething et al., Nature, 293:620-625, 1981; Mantei et al., Nature, 281:40-46, 1979; Levinson et al. EP 117,060; and EP 117,058. For mammalian cells, common methods of introducing genetic material into mammalian cells include the calcium phosphate precipitation method of Graham and van der Erb (Virology, 52:456-457, 1978) or the Lipofectamine™ (Gibco BRL) Method of Hawley-Nelson (Focus 15:73, 1993). General aspects of mammalian cell host system transformations have been described by Axel in U.S. Pat. No. 4,399,216. For various techniques for introducing genetic material into mammalian cells, see Keown et al., Methods in Enzymology, 1989, Keown et al., Methods in Enzymology, 185:527-537, 1990, and Mansour et al., Nature, 336:348-352, 1988.

The cells are cultured under conditions that allow expression of the polypeptide. The polypeptide can be recovered and purified using methods that are known to the skilled artisan.

Maximal Concentration and Area Under the Time-Concentration Curve of Endogenous FVIII According to a preferred aspect of the invention polypeptide as defined hereinabove is used for increasing the $C_{max}$ or AUC of endogenous Factor VIII as compared to untreated subjects by administration the polypeptide of the invention alone, i.e. without co-administration of FVIII.

The maximal concentration ($C_{max}$) is the highest plasma concentration value measured. Following administration of said recombinant polypeptide, the $C_{max}$ for FVIII may be at least 10 mIU/mL, at least 25 mIU/mL, at least 50 mIU/mL, at least 100 mIU/mL, at least 200 mIU/mL, at least 300 mIU/mL or at least 400 mIU/mL.

The $AUC_{0-t}$ is the peak area under the plasma concentration-time curve from zero to the last measured timepoint. Following administration of the recombinant polypeptide, the AUC for the endogenous FVIII increase may be at least 1000 mIU*h/mL, at least 2000 mIU*h/mL, at least 3000 mIU*h/mL, at least 5000 mIU*h/mL, at least 10000 mIU*h/mL or at least 20000 mIU*h/mL chromogenic FVIII activity.

Bioavailability of rD'D3-FP after Subcutaneous Administration

A further aspect of the invention pertains to providing or improving subcutaneous bioavailability of the polypeptide as defined hereinabove.

The term bioavailability, as used herein, is defined as the percentage of the $AUC_{0-inf}$ of polypeptide of the invention after s.c. administration, in relation to the $AUC_{0-inf}$ of polypeptide of the invention after i.v. administration. The $AUC_{0-inf}$ is the area under the plasma concentration-time curve from zero to infinity. For evaluation of the pharmacokinetic data for calculation of $AUC_{0-inf}$, a two-compartment model (biphasic pharmacokinetic profile) was applied.

According to certain embodiments, bioavailability of the recombinant polypeptide in the absence of co-administered FVIII is at least 30%, preferably at least 35%, more preferably at least 40%, at least 45% or at least 50%.

According to certain embodiments, bioavailability of the recombinant polypeptide following co-administration with FVIII is at least 30%, preferably at least 35%, more preferably at least 40%, at least 45% or at least 50%.

Treatment of Coagulation Disorder

A further aspect of this invention is a method of treating a blood coagulation disorder, comprising administering to a patient in need thereof an effective amount of a polypeptide as defined hereinabove.

The polypeptides of the invention are useful for treating blood coagulation disorders including hemophilia A and von-Willebrand disease. The term "hemophilia A" refers to a deficiency in functional coagulation FVIII, which is usually inherited. The von-Willebrand disease is selected from the group consisting of von-Willebrand disease type 2N, von-Willebrand disease type 3, and von-Willebrand disease type 1.

In another embodiment, the blood coagulation disorder is von-Willebrand disease type 1 characterized by an endogenous FVIII activity level before treatment which is reduced compared to the endogenous FVIII activity level in NHP.

The patient to be treated may have a reduced activity and/or level of endogenous FVIII as compared to the endogenous FVIII in NHP. The endogenous FVIII activity in the patient may be less than 80%, or less than 70%, or less than 60%, or less than 50%, or less than 40%, or less than 30%, or less than 20%, or less than 20%, or less than 10%, or less than 5% of the endogenous FVIII activity in NHP. The endogenous FVIII activity in the patient to be treated may be less than 0.8 IU/ml, or less than 0.7 IU/ml, or less than 0.6 IU/ml, or less than 0.5 IU/ml, or less than 0.4 IU/ml, or less than 0.3 IU/ml, or less than 0.2 IU/ml, or less than 0.1 IU/ml, or less than 0.05 IU/ml of whole blood.

The polypeptide of the invention is to be administered to a patient having an endogenous FVIII activity of at least 0.005 IU/mL. In certain embodiments, the polypeptide of the invention is to be administered to a patient having an endogenous FVIII activity of 0.01 to 0.4 IU/ml, or 0.02 to 0.3 IU/ml, or 0.03 to 0.2 IU/ml, or 0.04 to 0.1 IU/ml of whole blood.

In one embodiment, the blood coagulation disorder is moderate hemophilia A. Moderate hemophilia A is preferably characterized by an endogenous FVIII activity level which is from about 1% to about 5% of the endogenous FVIII activity level in NHP. Typically, subjects having moderate hemophilia A have an endogenous FVIII activity level from 0.01 to 0.05 IU/mL in plasma.

In another embodiment, the blood coagulation disorder is mild hemophilia A. Mild hemophilia A is preferably characterized by an endogenous FVIII activity level which is from about 5% to about 40% of the endogenous FVIII activity level in NHP. Typically, subjects having mild hemophilia A have an endogenous FVIII activity level from 0.05 to 0.4 IU/mL in plasma.

In another embodiment, the blood coagulation disorder is severe hemophilia A. Severe hemophilia A is characterized by endogenous FVIII activity level below 1% of the endogenous FVIII activity in NHP.

In another embodiment, the blood coagulation disorder is von-Willebrand disease type 2N. Von-Willebrand disease type 2N is preferably characterized by an endogenous FVIII activity level before treatment which is in a range between about 3 IU/dL and about 30 IU/dL FVIII activity level, corresponding to about 3% to about 30% of the endogenous FVIII activity level in NHP. Most of the patients have an endogenous FVIII activity level below 20 IU/dL, thus a level below 20% of the endogenous FVIII activity level in NHP. Thus, subjects having von-Willebrand disease type 2N have an endogenous FVIII activity level from 0.03 IU/mL to 0.3 IU/mL in plasma, typically below 0.2 IU/mL.

In another embodiment, the blood coagulation disorder is von-Willebrand disease type 3, preferably characterized by an endogenous FVIII activity level before treatment which is usually in a range between about 1 IU/dL and about 20 IU/dL FVIII activity level corresponding to about 1% to about 20% of the endogenous FVIII activity level in NHP. Most of the patients have an endogenous FVIII activity level below 10 IU/dL, thus a level below 10% of the endogenous FVIII activity level in NHP.

The polypeptide of the invention is preferably administered to a subject for the prophylactic prevention of a bleeding event. This treatment does not comprise administration of any exogenous FVIII. The polypeptide of the invention may also be administered to a subject for the treatment of a bleeding event. In that case, the polypeptide of the invention may be co-administered with exogenous FVIII. After such treatment of the bleeding event the follow-up treatment is then carried out without co-administration of exogenous FVIII. That is, the follow-up treatment is done with the polypeptide of the invention only.

Typically, the treatment with the polypeptide of the invention alone, i.e. without co-administration of exogenous FVIII, is continued until a bleeding event occurs. The duration of the treatment with the polypeptide of the invention alone, i.e. without co-administration of exogenous FVIII, is not particularly limited, it is usually continued for at least one week, or at least two weeks, or at least three weeks, or at least four weeks, or at least two months.

Treatment of a disease encompasses the treatment of patients already diagnosed as having any form of the disease at any clinical stage or manifestation; the delay of the onset or evolution or aggravation or deterioration of the symptoms or signs of the disease; and/or preventing and/or reducing the severity of the disease.

A "subject" or "patient" to whom a polypeptide of the invention is administered preferably is a human. In certain aspects, the human is a pediatric patient. In other aspects, the human is an adult patient.

Compositions comprising a polypeptide of the invention and, optionally FVIII, are described herein. The compositions typically are supplied as part of a sterile, pharmaceutical composition that includes a pharmaceutically acceptable carrier. This composition can be in any suitable form (depending upon the desired method of administering it to a patient).

The term "Factor VIII" and "FVIII" are used interchangeably herein and encompass both plasma derived FVIII and recombinant FVIII. Recombinant FVIII encompasses without limitation full-length FVIII as well as two-chain B-domain deleted or truncated variants as well as single-chain B-domain deleted or truncated variants for example those described in WO 2004/067566 and other FVIII variants with mutations outside the B-domain but having the biological activity of FVIII.

The polypeptide of the invention can be administered to a patient by a variety of routes such as orally, transdermally, subcutaneously, intranasally, intravenously, intraperitoneally, intramuscularly, topically or locally. The most suitable route for administration in any given case will depend on the particular polypeptide, the subject, and the nature and severity of the disease and the physical condition of the subject. Typically, a polypeptide of the invention will be administered intravenously.

In accordance with this invention, the patient being treated with the polypeptide of the invention may also be treated with blood coagulation Factor VIII, provided that the follow-up treatment is done with the polypeptide of the invention alone, i.e. without co-administration of exogenous FVIII. The polypeptide of the invention and the Factor VIII may be administered simultaneously or in a sequential fashion both modes of administration being encompassed by the term "combination therapy" and "co-administration". The polypeptide of the invention and the Factor VIII may be administered as a mixture, i.e. within the same composition, or separately, i.e. as separate compositions.

The polypeptide and optionally the FVIII are preferably administered intravenously or subcutaneously.

In a first embodiment, both the polypeptide and optionally the FVIII are administered intravenously. In a second embodiment, both the polypeptide and optionally the FVIII are administered subcutaneously.

In another embodiment, the FVIII is administered intravenously, and the polypeptide is administered via a different route. In further embodiments, the polypeptide is administered subcutaneously, and the FVIII is administered via a different route. For example, the polypeptide may be administered subcutaneously, and the FVIII may be administered intravenously.

In further embodiments, the FVIII is administered subcutaneously, and the polypeptide is administered via a different route. In further embodiments, the polypeptide is administered intravenously, and the FVIII is administered via a different route. For example, the polypeptide may be administered intravenously, and the FVIII may be administered subcutaneously.

Determination of the total number of doses, and length of treatment with a polypeptide of the invention is well within the capabilities of those skilled in the art. The dosage of the polypeptide of the invention to be administered may depend on the concentrations of the endogenous FVIII, the concentration of endogenous VWF in the patient to be treated, or both. An effective dosage based on the ratios described herein can be determined by the skilled person, taking into account the molecular weight of the polypeptide of the invention. Typical dosages for FVIII may range from about 20 U/kg body weight to about 100 U/kg body weight.

The concentration of Factor VIII in the composition used is typically in the range of 10-10,000 IU/mL. In different embodiments, the concentration of FVIII in the compositions of the invention is in the range of 10-8,000 IU/mL, or 10-5,000 IU/mL, or 20-3,000 IU/mL, or 50-1,500 IU/mL, or 3,000 IU/mL, or 2,500 IU/mL, or 2,000 IU/mL, or 1,500 IU/mL, or 1,200 IU/mL, or 1,000 IU/mL, or 800 IU/mL, or 750 IU/mL, or 600 IU/mL, or 500 IU/mL, or 400 IU/mL, or 300 IU/mL, or 250 IU/mL, or 200 IU/mL, or 150 IU/mL, or 125 IU/mL, or 100 IU/mL, or 62.5 IU/mL, or 50 IU/mL, provided the requirements regarding the ratio with respect to the VWF polypeptide of the invention as defined herein are fulfilled.

"International Unit," or "IU," is a unit of measurement of the blood coagulation activity (potency) of FVIII as measured by a FVIII activity assay such as a one stage clotting assay or a chromogenic substrate FVIII activity assay using a standard calibrated against an international standard preparation calibrated in "IU". One stage clotting assays are known to the art, such as that described in N Lee, Martin L, et al., An Effect of Predilution on Potency Assays of FVIII Concentrates, Thrombosis Research (Pergamon Press Ltd.) 30, 511 519 (1983). Principle of the one stage assay: The test is executed as a modified version of the activated Partial Thromboplastin Time (aPTT)-assay: Incubation of plasma with phospholipids and a surface activator leads to the activation of factors of the intrinsic coagulation system. Addition of calcium ions triggers the coagulation cascade. The time to formation of a measurable fibrin clot is determined. The assay is executed in the presence of Factor VIII deficient plasma. The coagulation capability of the deficient plasma is restored by Coagulation Factor VIII included in the sample to be tested. The shortening of coagulation time is proportional to the amount of Factor VIII present in the sample. The activity of Coagulation Factor VIII is quantified by direct comparison to a standard preparation with a known activity of Factor VIII in International Units.

Another standard assay is a chromogenic substrate assay. Chromogenic substrate assays may be purchased commercially, such as the coamatic FVIII test kit (Chromogenix-Instrumentation Laboratory SpA V. le Monza 338-20128 Milano, Italy). Principle of the chromogenic assay: In the presence of calcium and phospholipid, Factor X is activated by Factor IXa to Factor Xa. This reaction is stimulated by Factor VIIIa as cofactor. FVIIIa is formed by low amounts of thrombin in the reaction mixture from FVIII in the sample to be measured. When using the optimum concentrations of Ca2+, phospholipid and Factor IXa and an excess quantity of Factor X, activation of Factor X is proportional to the potency of Factor VIII. Activated Factor X releases the chromophore pNA from the chromogenic substrate S-2765. The release of pNA, measured at 405 nm, is therefore proportional to the amount of FXa formed, and, therefore, also to the Factor VIII activity of the sample.

According to some preferred embodiments of the use of the polypeptide, the endogenous FVIII level is increased following administration of said polypeptide to a level of at least 1%, or preferably at least 2%, at least 5%, at least 10%, at least 20%, at least 30%, at least 40%, at least 50%, at least 60%, at least 70%, at least 80%, at least 90% or at least 100% of the activity level of endogenous FVIII in normal human plasma (NHP).

In a further preferred embodiment the endogenous FVIII level is increased following administration of said polypeptide to a level being in a range between 1% to 500%, preferably between 1% to 400%, between 1% to 300%, between 1% to 200%, between 1% to 150%, or between 1% to 100% of the activity level of endogenous FVIII in normal human plasma (NHP).

In a further preferred embodiment the endogenous FVIII level is increased following administration of said polypeptide to a level being in a range between 5% to 400%, preferably between 5% to 300%, between 10% to 200%, between 10% to 150%, between 20% to 150%, or between 40% to 150% of the activity level of endogenous FVIII in normal human plasma (NHP).

In a further preferred embodiment the endogenous FVIII level is increased following administration of said polypeptide to a level as described herein, whereby the dosage of the administered polypeptide and/or the frequency of administration of the polypeptide is adjusted in order to achieve said levels of endogenous FVIII levels in the subject.

Ratios

In certain embodiments, the polypeptide of the invention is co-administered together with exogenous FVIII for the treatment of a bleeding event or for initiation of a prophylactic treatment regime, wherein for follow-up treatments said polypeptide is administered without co-administration of exogenous FVIII. For those embodiments comprising co-administration of the polypeptide of the invention together with exogenous FVIII, the polypeptide of the invention is preferably administered at a dose such that the molar ratio of the polypeptide to be co-administered to the exogenous FVIII is greater than 50.

The polypeptide of the invention may be a monomer, a dimer, or a mixture thereof. Any molar ratios according to the invention refer to a ratio of the molar concentration of the monomeric subunit of the polypeptide of the invention, whether actually present as monomer or dimer. Ratios are formed over the molar concentration of endogenous FVIII, or, at least for certain embodiments, of the co-administered FVIII or over the molar concentration of the endogenous VWF subunits, if present. Any ratios of polypeptide of the invention over FVIII in this application refer to the amount of monomers comprised in the polypeptide of the invention, which is preferably present as a dimer, to be administered (in mole) divided by the amount of FVIII to be administered (in mole), unless indicated otherwise. By way of non-limiting example the co-administration of 100 μM of a monomeric polypeptide of the invention with 1 μM of FVIII means a ratio of 100. The same ratio of 100 is obtained if 50 μM of a dimeric polypeptide of the invention are co-administered with 1 μM of FVIII.

The endogenous VWF is, if present, the VWF present in the plasma of the animal or human being to be dosed with the polypeptide of the invention. It usually consists of a range of different oligomers of approximately 2 to 40 monomeric subunits of VWF. Unless indicated otherwise, any ratios of polypeptide of the invention over endogenous VWF in this application refer to the molar plasma concentration of polypeptide of the invention per kg body weight of the treated subject immediately after administration of the polypeptide of the invention, divided by the molar plasma concentration of endogenous VWF per kg body weight of the treated subject. The molar plasma concentration of the polypeptide of the invention per kg body weight of the subject treated immediately after administration of the polypeptide of the invention is calculated assuming a dilution of the polypeptide of the invention administered directly after administration in a plasma volume of 40 ml/kg. The amount of the polypeptide of the invention immediately after administration when administered intravenously is assumed for the purposes of the invention to be identical to the amount administered.

According to one aspect of the invention the molar ratio of the polypeptide of the invention to the endogenous VWF is greater than 0.5. The concentration of endogenous VWF in the plasma of the subject to be treated can be determined by an ELISA or and activity assay, e.g. as described in the Examples. Typically, the concentration measured will be given in U/mL. This value can be converted into a molarity as described in the following.

Normal human plasma (NHP) contains VWF in a concentration of 1 U/mL or 100% by definition. This corresponds to a protein concentration of approximately 10 μg/mL (Haberichter S. L. and Montgomery R. R., Structure and function of von Willebrand factor; in: Hemostasis and Thrombosis, eds. Marder, Aird, Bennett, Schulman and White, Lippincott Williams & Wilkins 2013, pp 197-207). Based on this VWF concentration in NHP and a molecular weight of the mature VWF monomer of approximately 267,500 Da including 18-19% of glycosylation a molar plasma concentration of the VWF monomer unit of approximately $37 \times 10^{-9}$ Mol/L can be calculated for NHP.

For calculation of the molar concentrations of rat or rabbit VWF subunits in normal rat or rabbit plasma, respectively, a molecular weight of the monomeric subunit comparable to human VWF was used (267,500 Da) together with an assumed comparable specific activity (100 U/mg) and the measured endogenous VWF activities in rat or rabbit plasma (refer also to examples).

The concentration of VWF in the human population varies from about 60% to about 200% of VWF concentration in NHP. In certain embodiments of the invention the concentration of endogenous VWF is defined as the concentration in NHP. In other embodiments the concentration of endogenous VWF is determined in the subject to be treated, and the dose of the polypeptide is based on this individual value.

The molar ratio of the polypeptide of the invention administered to the endogenous VWF is preferably at least 2, or at least 3, or at least 4, or at least 5, or at least 6, or at least 7, or at least 8, or at least 9, or at least 10, more preferably at least 15, or at least 20, or at least 25, or at least 30, most preferably at least 40, or at least 50, or at least 75.

The molar ratio of the polypeptide of the invention to be administered to the endogenous VWF may range from 0.5 to 1,000, or from 1 to 500, or from 2 to 400, or from 3 to 300, or from 4 to 250, or from 5 to 200, or from 6 to 150, or from 7 to 140, or from 8 to 130, or from 9 to 120, or from 10 to 110. Preferably, the molar ratio of the polypeptide of the invention administered to endogenous VWF ranges from 3 to 100, or from 4 to 90, or from 5 to 80, or from 6 to 75, or from 10 to 60.

The molar ratio of the polypeptide of the invention to be administered to endogenous FVIII is preferably at least 2, or at least 5, or at least 10, or at least 20, or at least 30, or at least 40, or at least 50, more preferably the ratio is greater than 50, or at least 75, at least 100, or greater than 100, or at least 200, most preferably at least 300, or at least 400, or at least 500.

The molar ratio of the polypeptide of the invention to be administered to endogenous FVIII may range from 2 to 10,000, or from 5 to 5,000, or from 10 to 4,000, or from 20 to 3,000, or from 30 to 2,000, or from 40 to 1,000. Preferably, the molar ratio of the polypeptide of the invention to be administered to endogenous FVIII ranges from 60 to 2,500, or from 110 to 2,000, or from 150 to 1,500, or from 200 to 1,000.

The molar ratio of the polypeptide of the invention to be administered to exogenous FVIII to be co-administered is preferably at least 2, or at least 5, or at least 10, or at least 20, or at least 30, or at least 40, or at least 50, more preferably the ratio is greater than 50, or at least 75, at least 100, or greater than 100, or at least 200, most preferably at least 300, or at least 400, or at least 500.

The molar ratio of the polypeptide of the invention to be administered to FVIII to be co-administered may range from 2 to 10,000, or from 5 to 5,000, or from 10 to 4,000, or from 20 to 3,000, or from 30 to 2,000, or from 40 to 1,000. The molar ratio of the polypeptide of the invention to be administered to FVIII to be co-administered may preferably range from 50 to 10,000, or from 50 to 5,000, or from 50 to 4,000, or from 50 to 3,000, or from 50 to 2,000, or from 50 to 1,000. Preferably, the molar ratio of the polypeptide of the invention to be administered to FVIII to be co-administered ranges from 60 to 2,500, or from 110 to 2,000, or from 150 to 1,500, or from 200 to 1,000.

Pharmaceutical Compositions

Therapeutic formulations of the polypeptide of the invention suitable in the methods described herein can be prepared for storage as lyophilized formulations or aqueous solutions by mixing the polypeptide having the desired degree of purity with optional pharmaceutically-acceptable carriers, excipients or stabilizers typically employed in the art (all of which are referred to herein as "carriers"), i.e., buffering agents, stabilizing agents, preservatives, isotonifiers, non-ionic detergents, antioxidants, and other miscellaneous additives. See, Remington's Pharmaceutical Sciences, 16th edition (Osol, ed. 1980). Such additives must be nontoxic to the recipients at the dosages and concentrations employed.

Buffering agents help to maintain the pH in the range which approximates physiological conditions. They can present at concentration ranging from about 2 mM to about 50 mM. Suitable buffering agents include both organic and inorganic acids and salts thereof such as citrate buffers (e.g., monosodium citrate-disodium citrate mixture, citric acid-trisodium citrate mixture, citric acid-monosodium citrate mixture, etc.), succinate buffers (e.g., succinic acid-monosodium succinate mixture, succinic acid-sodium hydroxide mixture, succinic acid-disodium succinate mixture, etc.), tartrate buffers (e.g., tartaric acid-sodium tartrate mixture, tartaric acid-potassium tartrate mixture, tartaric acid-sodium hydroxide mixture, etc.), fumarate buffers (e.g., fumaric acid-monosodium fumarate mixture, fumaric acid-disodium fumarate mixture, monosodium fumarate-disodium fumarate mixture, etc.), gluconate buffers (e.g., gluconic acid-sodium glyconate mixture, gluconic acid-sodium hydroxide mixture, gluconic acid-potassium gluconate mixture, etc.), oxalate buffer (e.g., oxalic acid-sodium oxalate mixture, oxalic acid-sodium hydroxide mixture, oxalic acid-potassium oxalate mixture, etc), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris can be used.

Preservatives can be added to retard microbial growth, and can be added in amounts ranging from 0.2%-1% (w/v). Suitable preservatives include phenol, benzyl alcohol, meta-cresol, methyl paraben, propyl paraben, octadecyldimethylbenzyl ammonium chloride, benzalconium halides (e.g., chloride, bromide, and iodide), hexamethonium chloride, and alkyl parabens such as methyl or propyl paraben, catechol, resorcinol, cyclohexanol, and 3-pentanol. Isotonicifiers sometimes known as "stabilizers" can be added to ensure isotonicity of liquid compositions and include polhydric sugar alcohols, preferably trihydric or higher sugar alcohols, such as glycerin, erythritol, arabitol, xylitol, sorbitol and mannitol. Stabilizers refer to a broad category of excipients which can range in function from a bulking agent to an additive which solubilizes the therapeutic agent or helps to prevent denaturation or adherence to the container wall. Typical stabilizers can be polyhydric sugar alcohols (enumerated above); amino acids such as arginine, lysine, glycine, glutamine, asparagine, histidine, alanine, ornithine, L-leucine, 2-phenylalanine, glutamic acid, threonine, etc., organic sugars or sugar alcohols, such as lactose, trehalose, stachyose, mannitol, sorbitol, xylitol, ribitol, myoinisitol, galactitol, glycerol and the like, including cyclitols such as inositol; polyethylene glycol; amino acid polymers; sulfur containing reducing agents, such as urea, glutathione, thioctic acid, sodium thioglycolate, thioglycerol, α-monothioglycerol and sodium thio sulfate; low molecular weight polypeptides (e.g., peptides of 10 residues or fewer); proteins such as human serum albumin, bovine serum albumin, gelatin or immunoglobulins; hydrophylic polymers, such as polyvinylpyrrolidone monosaccharides, such as xylose, mannose, fructose, glucose; disaccharides such as lactose, maltose, sucrose and trisaccacharides such as raffinose; and polysaccharides such as dextran. Stabilizers can be present in the range from 0.1 to 10,000 weights per part of weight active protein.

Non-ionic surfactants or detergents (also known as "wetting agents") can be added to help solubilize the therapeutic agent as well as to protect the therapeutic protein against agitation-induced aggregation, which also permits the formulation to be exposed to shear surface stressed without causing denaturation of the protein. Suitable non-ionic surfactants include polysorbates (20, 80, etc.), polyoxamers (184, 188 etc.), Pluronic polyols, polyoxyethylene sorbitan monoethers (TWEEN®-20, TWEEN®-80, etc.). Non-ionic surfactants can be present in a range of about 0.05 mg/ml to about 1.0 mg/ml, or in a range of about 0.07 mg/ml to about 0.2 mg/ml.

Additional miscellaneous excipients include bulking agents (e.g., starch), chelating agents (e.g., EDTA), antioxidants (e.g., ascorbic acid, methionine, vitamin E), and cosolvents.

The formulation herein can also contain a second therapeutic agent in addition to a polypeptide of the invention. Examples of suitable second therapeutic agents are provided below.

The dosing schedule can vary from once a month to daily depending on a number of clinical factors, including the type of disease, severity of disease, and the patient's sensitivity to the polypeptide of the invention. In specific embodiments, a polypeptide of the invention is administered, twice weekly, every 5 days, once weekly, every 10 days, every two weeks, every three weeks, every four weeks or once a month, or in any range between any two of the foregoing values, for example from every four weeks to every month, from every 10 days to every two weeks, or from two to three times a week, etc.

The dosage of a polypeptide of the invention to be administered will vary according to the particular polypeptide, the subject, and the nature and severity of the disease, the physical condition of the subject, the therapeutic regimen (e.g., whether a second therapeutic agent is used), and the selected route of administration; the appropriate dosage can be readily determined by a person skilled in the art.

It will be recognized by one of skill in the art that the optimal quantity and spacing of individual dosages of a polypeptide of the invention will be determined by the nature and extent of the condition being treated, the form, route and site of administration, and the age and condition of the particular subject being treated, and that a physician will ultimately determine appropriate dosages to be used. This dosage can be repeated as often as appropriate. If side effects develop the amount and/or frequency of the dosage can be altered or reduced, in accordance with normal clinical practice.

The nucleotide and amino acid sequences shown in the sequence listing are summarized in the Table 1.

TABLE 1

| SEQ ID NO: | Remarks |
| --- | --- |
| 1 | DNA sequence encoding a polypeptide comprising acids 1 to 1242 of human VWF, a glycine/serine linker and human albumin; nucleotide positions (nt): nt 1-6: EcoRI restriction enzyme cleavage site<br>nt 32-3757: coding sequence for VWF amino acids 1 to 1242<br>nt 3758-3850: coding sequence for glycine/serine linker<br>nt 3851-5608: coding sequence for human albumin<br>nt 5609-5616: NotI restriction enzyme cleavage site |

TABLE 1-continued

| SEQ ID NO: | Remarks |
|---|---|
| 2 | Amino acid sequence encoded by SEQ ID NO: 1 (mature form): amino acid positions (aa):<br>aa 1-479: VWF D'D3 region (VWF amino acids 764-1242)<br>aa 480-510: glycine/serine linker<br>aa 511-1095: human albumin |
| 3 | DNA sequence encoding the pre-pro form of human native VWF |
| 4 | Amino acid sequence encoded by SEQ ID NO: 3 |
| 5 | Amino acid sequence of a single chain Factor VIII molecule |
| 6 | Amino acid sequence of mature human serum albumin |
| 7 | Amino acid sequence of D'D3-CTP<br>aa 1-479: VWF D'D3 region (VWF amino acids 764-1242)<br>aa 480-511: glycine/serine linker<br>aa 512-576: C-terminal peptide of human chorionic gonadotropin-β subunit<br>aa 577-584: polyhistidine tag |

The following Examples illustrate the invention but should not be construed as limiting the present invention to the specific embodiments described herein below.

EXAMPLES

Example 1: FVIII Level Analysis in Plasma after Administration of rD'D3-FP

We aimed at characterizing the impact of rD'D3-FP on endogenous FVIII levels, thereby generally supporting a treatment of mild to moderate or severe Hemophilia A patients or certain types of von-Willebrand disease with low level VWF and functional endogenous FVIII. We investigated this effect in different approaches:
  Intravenous administration to models with normal endogenous FVIII and VWF levels, i.e. rats (example 1.1), rabbits (example 1.2) and monkeys (example 1.3), to investigate a potential further increase of endogenous FVIII after intravenous (i.v.) rD'D3-FP administration in a healthy subject.
  Intravenous administration to models with low FVIII levels due to VWF deficiency, i.e. VWF ko rats (example 1.4) and VWF ko mice (example 1.5), to investigate the size of increase of endogenous FVIII after i.v. rD'D3-FP administration in a diseased subject.
  Intravenous administration to models with low FVIII levels due to VWF deficiency, i.e. VWF ko rats, to investigate the size of increase of endogenous FVIII after i.v. administration of rD'D3-FP variants in a diseased subject (example 1.6).
  Subcutaneous administration to models with normal or low FVIII levels, i.e. pig, FVIII ko and VWF ko mouse and FVIII ko and VWF ko rat and (example 1.7) was investigated to compare i.v. and s.c. bioavailability of rD'D3-FP as well as effects on endogenous FVIII.
  A final experiment investigated the effects of multiple rD'D3-FP doses (i.v.) in VWF ko rats (example 1.8).
  Investigation of rD'D3-FP given subcutaneously and rVIII-SingleChain given intravenously in a hemophilia A model, i.e. in FVIII ko rat (example 1.9).

Materials and Methods

For the Examples, a polypeptide comprising a truncated VWF having an amino acid sequence as defined in SEQ ID NO:2 was used. This particular fusion protein consists of an N-terminal amino acid sequence from 1-479 representing the VWF D'D3 region (amino acids 764-1242 of human native VWF), followed by a 31 amino acid glycine/serine linker peptide and a C-terminal human albumin amino acid sequence from 511-1095. This fusion protein having a sequence as defined in SEQ ID NO:2 is referred to as rD'D3-FP or rD'D3-FP WT in the following.

As an alternative for the albumin as half-life extending polypeptide (HLEP), in some Examples another half-life extended rD'D3 variant is used having instead of albumin a CTP (C-terminal peptide of human chorionic gonadotropin-1R subunit) fused to D'D3 via a glycine/serine linker which is referred to as rD'D3-CTP hereinafter. The fusion protein rD'D3-CTP has a sequence as defined in SEQ ID NO:7.

In certain Examples high affinity variants of rD'D3-FP were used. One particular variant fusion protein consists of an N-terminal amino acid sequence from 1-479 representing the VWF D'D3 region (amino acids 764-1242 of human native VWF), followed by a 31 amino acid glycine/serine linker peptide and a C-terminal human albumin amino acid sequence from 511-1095, provided that within the D' domain of said polypeptide two amino acid substitutions are present, i.e. S764E and S766Y. This fusion protein consists of a sequence as defined in SEQ ID NO:2 having said two substitutions, namely S764E and S766Y, within the D'D3 region. The VWF amino acid S764 corresponds to the amino acid number 1 within the sequence of SEQ ID NO:2 (see also Table 1). The rD'D3-FP EY variant has been generated as described in WO 2016/000039 A1. Said variant is referred to as rD'D3-FP EY hereinafter.

In certain Examples another high affinity variant of rD'D3-FP was used. This particular variant fusion protein consists of an N-terminal amino acid sequence from 1-479 representing the VWF D'D3 region (amino acids 764-1242 of human native VWF), followed by a 31 amino acid glycine/serine linker peptide and a C-terminal human albumin amino acid sequence from 511-1095, provided that within the D'D3 domain of said polypeptide three amino acid substitutions are present, i.e. S764E, S766Y and V1083A. This fusion protein consists of a sequence as defined in SEQ ID NO:2 having said three substitutions S764E, S766Y, and V1083A within the D'D3 region. Said variant is referred to as rD'D3-FP EYA hereinafter.

Analytics

In all examples, rD'D3-FP was applied at dose levels quantified by a human albumin ELISA, i.e. measuring the albumin part of the protein. This rD'D3-FP ELISA was used for formulation and plasma samples (except for the monkey plasma samples, who showed relevant human albumin cross-reactivity).

In examples where rD'D3-CTP was used as a rD'D3 variant, the polypeptide was applied at dose levels quantified by $OD_{280}$ measurement, and the protein amount was adjusted to a molarity in the same high range as rD'D3-FP.

The ("standard") rD'D3-FP ELISA used a polyclonal goat anti-human albumin capture antibody from Bethyl Laboratories, Inc. (Montgomery, USA). The detection solution consists of a polyclonal peroxidase labelled anti-human albumin detection antibody preparation (Bethyl Laboratories Inc., Montgomery, USA). A chromogenic readout, i.e. TMB from Siemens Healthcare (Eschborn, Germany) was used for quantification in a microplate reader at 450/650 nm (ELx808, BioTek, USA) directly after stopping. As a standard, the drug formulation containing rD'D3-FP was used. rD'D3-FP amounts are given in mg albumin, i.e. no adjustment was done for the D'D3 part of the molecule. The rD'D3-FP ELISA for monkey plasma samples was set up as a mixed ELISA, where the D'D3 domain was captured and the albumin domain was detected. The assay used an anti-D'D3 monoclonal capture antibody (CSL Behring, in house research grade preparation). The detection solution consists of a polyclonal peroxidase labelled anti-human albumin detection antibody preparation (Bethyl Laboratories Inc., Montgomery, USA). A chromogenic readout, i.e. TMB from Siemens Healthcare (Eschborn, Germany) was used for quantification in a microplate reader at 450/650 nm (ELx808, BioTek Instruments Inc., Winooski, USA) directly after stopping. As a standard, the drug formulation containing rD'D3-FP was used. rD'D3-FP amounts are given in mg albumin, i.e. no adjustment was done for the D'D3 part of the molecule.

The plasma samples of the PK containing rD'D3-CTP were measured in an anti-D'D3 ELISA. This anti D'D3 ELISA was conducted with two monoclonal anti-human D'D3 antibodies in a sandwich format. Both antibodies for capture and detection were derived from an in house research preparation. The anti-human D'D3 detection antibody was peroxidase labelled. A chromogenic readout, i.e. TMB from Siemens Healthcare (Eschborn, Germany) was used for quantification in a microplate reader at 450/650 nm (ELx808, BioTek Instruments Inc., Winooski, USA) directly after stopping. As a standard, the drug formulation containing rD'D3-CTP was used. rD'D3-CTP amounts are given as rD'D3-CTP concentrations.

Human FVIII:Ag plasma levels were determined with the FVIII Asserachrom ELISA test kit from Stago, S.A.S., France according to the test instruction manual. The Asserachrom testkit contained all reagents with exception of the stop solution, which was obtained from Siemens Healthcare (Eschborn, Germany). As a standard, the drug formulation containing rVIII-SingleChain was used.

FVIII chromogenic activity plasma levels were detected by the COAMATIC® FVIII assay (FVIII:C chromogenic assay, Chromogenix, Instrumentation Laboratory SpA, Milan, Italy) according to the test instruction manual of the manufacturer on a BCS XP analyzer from Siemens Healthcare Diagnostics (Marburg, Germany). For calibration, standard human plasma was used. Alternatively, they were detected by the same COAMATIC® FVIII assay with pre-dilution of the samples in human FVIII deficient plasma from Siemens Healthcare Diagnostics (Marburg, Germany), followed by a readout on the Infinite M200 ELISA-Reader from Tecan (Tecan Trading AG, Switzerland). For calibration, a human plasma-derived von Willebrand factor and FVIII containing product, Haemate® P from CSL Behring, was used. The samples were measured at 405 nm without reference. In general, FVIII chromogenic activity is abbreviated as FVIII:C.

FVIII clotting activity plasma levels were detected using a one-stage clotting assay, which includes Pathromtin® SL, human FVIII deficient plasma and calcium chloride solution, which are all commercially available from Siemens Healthcare Diagnostics (Marburg, Germany). Measures were performed on a BCS XP analyzer from Siemens Healthcare Diagnostics (Marburg, Germany). For calibration, standard human plasma was used. Activated partial thromboplastin time (aPTT) was analysed in plasma samples using Pathromtin® SL reagent (mouse and rat) or Actin® FSL (rabbit) and calcium chloride solution on a BCS XP analyzer from Siemens Healthcare Diagnostics (Marburg, Germany). All reagents are commercially available from Siemens Healthcare Diagnostics (Marburg, Germany).

Experimental Animals

FVIII Ko Mouse

FVIII ko mice (representing a hemophilia A phenotype) were chosen, since they lack exons 16 and 17 of the FVIII gene, and thus have no plasma factor VIII activity (Bi L. et al, Nature genetics, 1995, Vol 10(1), 119-121; Bi L. et al, Blood, 1996, Vol 88(9), 3446-3450). This allows the analysis of FVIII activity levels following treatment with FVIII by quantification of FVIII activity in the plasma of these mice.

FVIII Ko Rat

FVIII ko rats, representing a hemophilia A phenotype, were generated at SAGE Labs (A Horizon Discovery Group Company, Saint Louis, Mo. 63146, USA) using the CRISPR/Cas9 technology. A 2 bp (basepair) deletion and a 1 bp insertion at position 23471-23472 within exon 18 was induced, leading to an early stop codon. The generated FVIII ko mutation resulted in a FVIII ko rat with disrupted FVIII function. This allows the analysis of FVIII activity levels following treatment with FVIII by quantification of FVIII activity in the plasma of these rats.

VWF Ko Mouse

VWF knock-out (ko) mice (representing a VWD phenotype) were chosen, since they lack exons 4 und 5 of the VWF gene, and thus have no plasma VWF activity (Denis C. et al, Proc. Natl. Acad. Sci. USA, 1998, Vol 95, 9524-9529). This allows the analysis of D'D3 polypeptides on endogenous FVIII activity levels in the plasma of these mice.

VWF Ko Rat

VWF ko rats, representing a VWD phenotype, were generated at Sigma Advanced Genetic Engineering (SAGE) Labs (Saint Louis, Mo. 63146, USA) using the CompoZr™ Zinc Finger Nuclease (ZFN) technology and SAGEspeed™ animal Knockout production processes. A 16 bp (basepair) deletion at position 33926 bp-33941 bp in the genomic sequence was induced within exon 7 leading to an early stop codon. The generation of knock-out rats in general using the ZFN technology by Sigma Advanced Genetic Engineering (SAGE) Labs (Sigma-Aldrich Biotechnology) is described in X. Cui et al. (Nature Biotechnology, 2010), in M H. Porteus & D. Carroll (Nature Biotechnology, 2005). The generated VWF ko mutation resulted in a VWF ko rat with disrupted VWF function. This allows the analysis of D'D3 polypeptides on endogenous FVIII activity levels in the plasma of these rats.

Generation of D'D3 Albumin Fusion Protein (D'D3-FP):

The expression cassette for D'D3-FP consisting of cDNA encoding VWF amino acids 1 to 1242, a glycine/serine linker and the cDNA of human albumin was prepared by custom gene synthesis (Eurofins Genomics, Ebersberg, Germany). Through flanking restriction sites (EcoRI, NotI) the expression cassette was excised from the cloning vector supplied and inserted into a pIRESneo3 vector (BD Biosciences, Franklin Lakes, N.J., USA) linearized with EcoRI and NotI. The resulting expression plasmid contained nucleotide sequences encoding the VWF propeptide, D' and D3 (VWF amino acids 1 to 1242 of SEQ ID NO: 4) fused to the albumin coding sequence through a short linker coding sequence under CMV promoter control. The nucleotide sequence of the coding sequence is displayed as SEQ ID NO: 1, the amino acid sequence of the mature D'D3-FP is shown as SEQ ID NO: 2. The presence of the D1D2 VWF propeptide (741 amino acids) during expression is crucial for dimerization of the synthesized polypeptide.

A similar approach was used to generate an expression plasmid for a D'D3 fusion protein to the C-terminal peptide of human chorionic gonadotropin-1R subunit, linked via a glycine/serine linker and tagged by 8 histidines at the C-terminus of the fusion protein. The amino acid sequence of the mature rD'D3-CTP is shown as SEQ ID NO: 7.

The expression plasmid as described above was grown up in XL10 Gold (Agilent Technologies) and purified using standard protocols (Qiagen, Hilden, Germany).

CHO K1 cells were transfected using the Lipofectamine 2000 reagent (Invitrogen) and grown up in serum-free medium (CD-CHO, Invitrogen) in the presence of 500-1000 µg/ml Geneticin. An expression plasmid encoding PACE/furin (pFu-797) as described in WO2007/144173 was cotransfected to maximize propeptide cleavage efficacy. Single cell derived clones were grown up and selected according to their D'D3-FP expression yield as quantified by an albumin specific enzyme immunoassay (see below). The cell line finally selected for D'D3-FP fermentation was called T2050-CL3.

Production of rD'D3-FP was carried out in bioreactors applying a fermentation process in perfusion mode. The fermentation process for the production of rD'D3-FP started with the thaw of cell line T2050-CL3 followed by cell expansion in shake flasks and finally a fermentation process in perfusion mode using the Sartorius BioStat B-DCU 5 L bioreactor and the BioStat STR 50 L single-use bioreactors. The BioSeps 10 L or 200 L (Applikon), respectively, were used as cell retention devices. Cell culture media were either PowerCHO3 (Lonza BESP1204) with 8 mM L-glutamine and 1 µM $CuSO_4$ or ProCHO5 (Lonza BESP1072) with 10 mM L-glutamine and 1 µM $CuSO_4$.

The seed trains in shake flasks were performed at 37° C., 7.5% $CO_2$ at a shaker speed of 160 rpm.

The 5 L bioreactor was inoculated with a target VCD of $2.5 \times 10^5$ cells/mL. The cells were cultivated in PowerCHO3 with 8 mM L-glutamine and 1 µM $CuSO_4$ at a temperature of +37.0° C., a pH of 7.00, and at 30% oxygen saturation. A temperature shift to +34.0° C. (evaluated range +31° C. to +35° C.) was performed after initial harvests from the bioreactor run at +37° C. had been taken. The pH was controlled using $CO_2$ sparged as acid and $NaHCO_3$ as base. The overlay air flow rate was set to 0.5 L/min. A ring sparger was used as a sparging unit. The agitation rate was 150 rpm with a 2 fold pitch blade impeller in down pull mode.

The 50 L bioreactor was inoculated with a target VCD of $3.0 \times 10^5$ cells/mL. The cells were cultivated in ProCHO5 medium with 10 mM L-glutamine and 1 µM $CuSO_4$ at a temperature of +37.0° C., a pH of 6.90, and at 30% oxygen saturation. A temperature shift to +34.0° C. was performed after the initial one or two harvests. PH control as above, the overlay air flow rate was set to 2 L/min. A micro sparger was used as a sparging unit. The agitation rate was 90 rpm with a 2 fold pitch blade impeller in down pull mode.

The perfusion was initiated when the VCD in the bioreactor was $>1.0 \times 10^6$ cells/mL. The perfusion rate was set to 1.0 volume/volume/day. The BioSep was operated in back flush mode with 5 (10) minutes runtime and 10 seconds back flush at a power input of 7 (30) W (numbers in brackets refer to the 50 L bioreactor). The perfusate and the bleed were filtered inline and collected in bags over 48 hours at +2 to +8° C. The VCD was controlled by active bleeding using a turbidity probe using glucose consumption as parameter with a target of 2 g/L glucose. Harvest and bleed were filtered inline, the harvest system consisting of a disposable filter and disposable bag was changed every second day.

To prepare material for the PK analyses described below harvests were purified by affinity and size exclusion chromatography. Briefly, the cell-free harvest from the bioreactor was concentrated 30-fold using a TFF system (e.g. Pall Centramate 500 S) with a 30 kD membrane (e.g Pall Centramate OS030T12). That concentrate was spiked with NaCl and EDTA to a final concentration of 0.75 M NaCl and 5 mM EDTA and loaded overnight on a CaptureSelect Human Albumin column (Life Technologies) which was pre-equilibrated with 20 mM Tris buffer pH 7.4. After washing the column with equilibration buffer rD'D3-FP was eluted with elution buffer (20 mM Tris, 2 M $MgCl_2$, pH 7.4). The eluate was then 10-fold concentrated and dialyzed against 50 mM Tris, 150 mM NaCl, pH 7.4 using Ultra Centrifugal Filters with a 30 kD cut-off (e.g. Amicon. UFC903024). To separate the rD'D3-FP dimer from the monomer portion that material was loaded on a Superdex 200 µg column (GE Healthcare Code: 17-1069-01) pre-equilibrated with 50 mM Tris, 150 mM NaCl, pH 7.4 and the peak fractions containing the D'D3-FP dimer were pooled. The area under the curve for the dimer and monomer peak fractions were used to calculate dimer to monomer ratio. Dimer preparations of said D'D3 albumin fusion protein were used for the pharmacokinetic experiments in Examples 1.1-1.6. Such dimer preparations are referred to as D'D3-FP or rD'D3-FP in the following, if not indicated otherwise.

The rD'D3-FP EY and EYA variants have been generated by equivalent method steps.

Example 1.1: Impact of Intravenous Treatment with rD'D3-FP on Physiological Endogenous FVIII Levels in Rats Animals Female Crl:CD (Sprague Dawley) rats in a weight range of 200-294 g were breed at Charles River Laboratories (Sulzfeld, Germany). In house, the animals were kept at standard housing conditions, i.e. at 20-24° C. under a 12 h/12 h light-darkness cycle. Animals were fed ad libitum with standard mouse and rat diet (Ssniff-Versuchsdiäten, Soest, Germany). Tap water was supplied ad libitum. Animal husbandry and study procedures complied with the German Animal Welfare law and European Union regulations.

For the 1 mg/kg group the group size was n=9, divided in 3 cohorts, except for the control (n=3 animals only). The group size of the 1 mg/kg group was n=6, divided in 2 cohorts. Thus, n=3 animals per time-point were used always.

Experimental Details

The test articles were administered i.v. by a single injection into the lateral tail vein of the rats (n=3 per group). rD'D3-FP was applied at a dose level of 1 mg/kg or 3 mg/kg based on human albumin values. Blood samples of the 1 mg/kg group were taken retroorbitally (the terminal sampling at day 10 and 14 by Vena cava puncturing) at pre-dose, 6 h and 1, 2, 3, 4, 5, 7, 10 and 14 days post administration (p.a.) after intravenous bolus injection. Blood samples of the 3 mg/kg group were drawn at 0.083, 3, 8 h and 1, 2, 3 and 4 days post administration. They were anticoagulated using sodium citrate (1 part sodium citrate 3.13%+9 parts blood), processed to plasma and stored at approx. −70° C. for the determination of rD'D3-FP and/or FVIII activity.

rD'D3-FP exposure was determined by measurement of the albumin part of the construct using a human albumin ELISA. FVIII activity plasma levels were detected using a chromogenic assay as well as a one-stage clotting assay.

Calculation of the total peak area under the curve (AUC) was done with GraphPad Prism (GraphPad Software, La Jolla, Calif., USA) over the period of 14 days using the pretreatment values as baseline and identifying peaks with a ≥30% distance from minimum to maximum values.

Results rD'D3-FP was quantified up to 4 d (3 mg/kg) or 14 d (1 mg/kg) p.a., and measured data were well above the detection limit over the whole observation period (FIG. 1A). A linear dose-dependency was observed for the 2 tested doses.

Figure 1B:
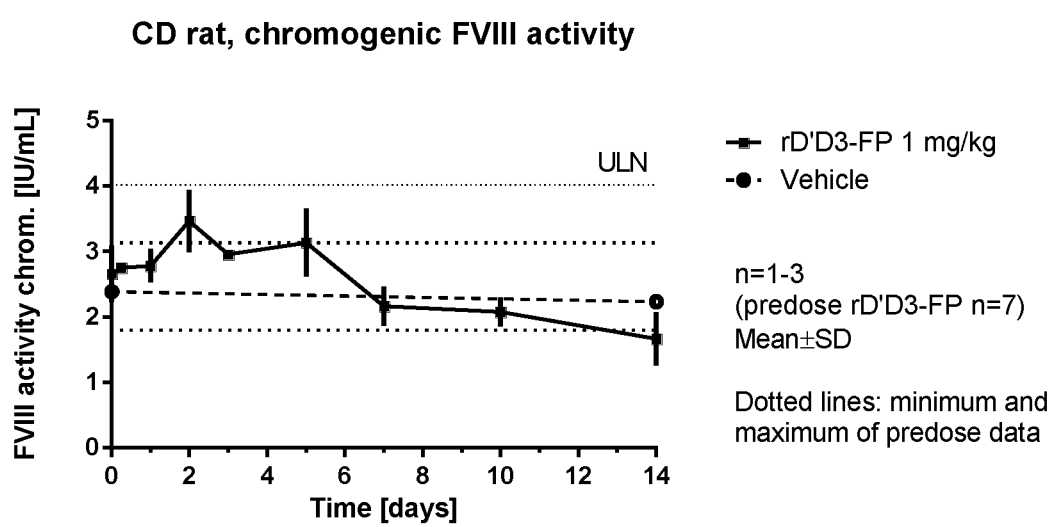
FIG. 1B shows FVIII activity quantified as chromogenic FVIII activity in IU/mL in CD rats after i.v. administration of rD'D3-FP, as described in Example 1.1, and data is given as mean±SD for n=1-3 rats per timepoint (except for the predose data: n=7). Dotted lines represent the minimum and maximum of predose data. Dotted lines marked as ULN represent the upper limit of normal.
Figure 1C:
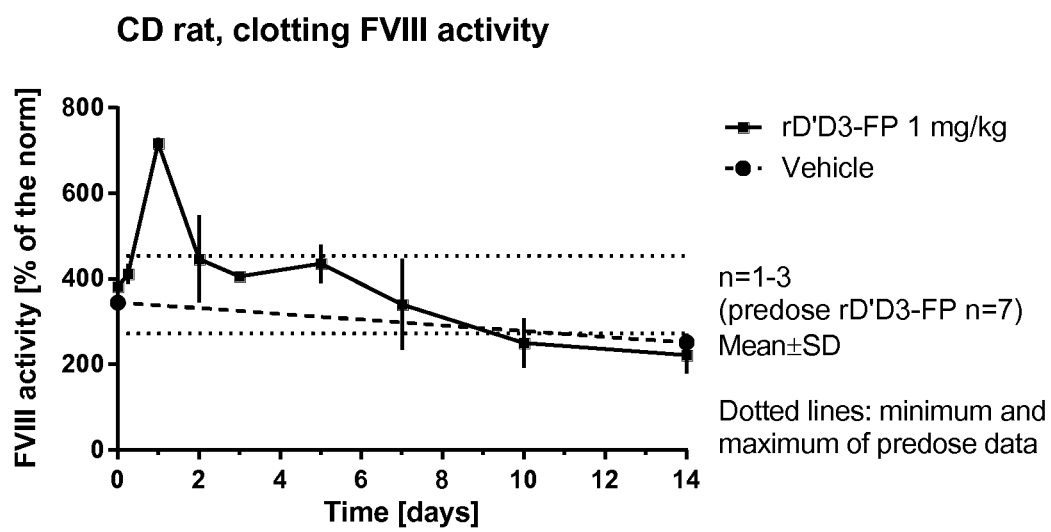
FIG. 1C shows FVIII activity quantified as clotting FVIII activity in % of the norm in CD rats after i.v. administration of rD'D3-FP, as described in Example 1.1, and data is given as mean±SD for n=1-3 rats per timepoint (except for the predose data: n=7). Dotted lines represent the minimum and maximum of predose data. Dotted lines marked as ULN represent the upper limit of normal.
Figure 1D:
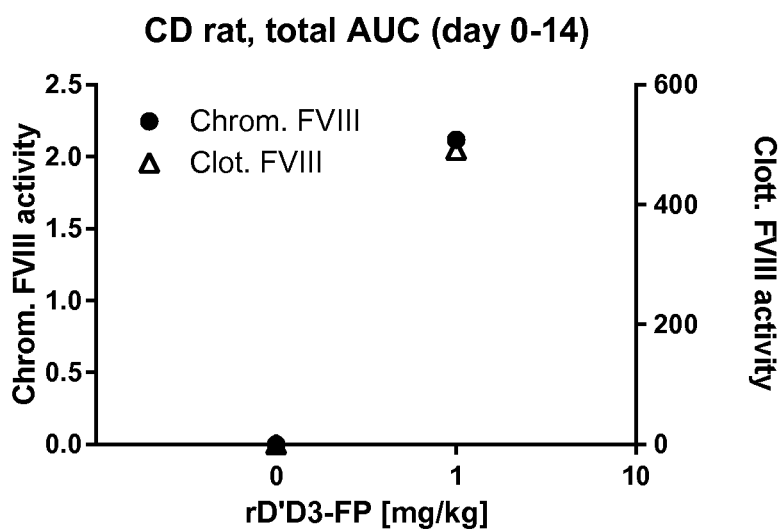
FIG. 1D shows FVIII activity quantified as chromogenic or clotting FVIII activity as above. AUC was calculated as peak area under the plasma concentration-time curve from time zero to until day 14.

FVIII activity was measured as chromogenic and one-stage clotting activity for the group treated with 1 mg/kg rD'D3-FP, and both FVIII activity tests showed transient increases in endogenous FVIII levels as compared to the saline control after administration of rD'D3-FP (FIGS. 1B and 1C), with a peak between days 2 (chromogenic activity) or 1 (clotting activity) to day 5 p.a. Again for both assays, mean FVIII concentrations hardly exceeded the maximum predose values, i.e. 3.1 IU/mL for chromogenic FVIII activity and 454% (4.5 IU/mL) for clotting FVIII activity. It shall be mentioned, that the upper limit of normal (ULN) with the dilution of 1:4 used for quantification of the samples was not reached for any of the animals. In line with this, AUC (evaluated over days 0 to 14 p.a.) as shown in FIG. 1D increased with the chromogenic as well as with the clotting assay at a dose of 1 mg/kg rD'D3-FP.

Figure 1E:
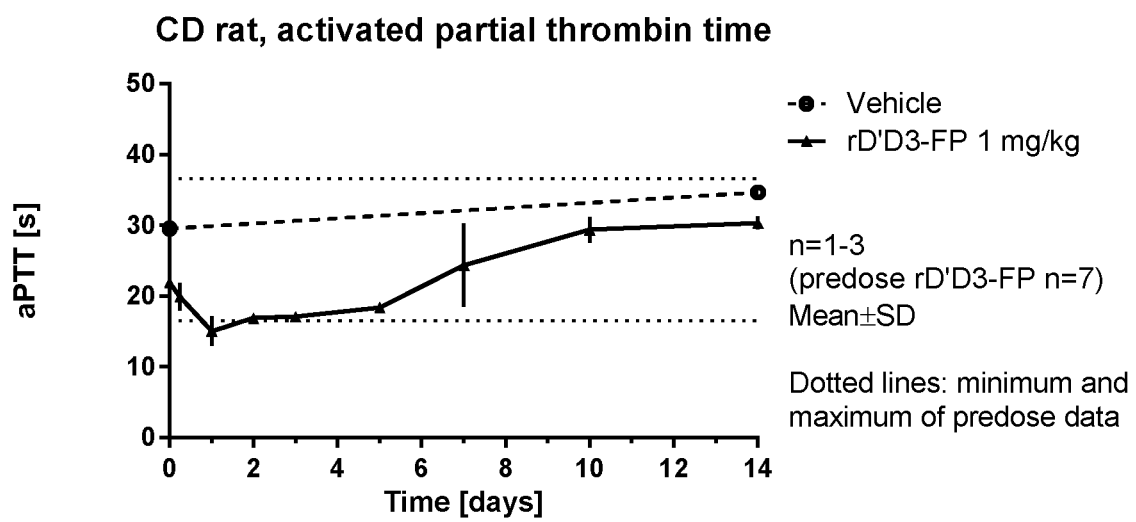
FIG. 1E shows activated partial thrombin time (aPTT) using Pathromtin® SL in CD rats after i.v. administration of rD'D3-FP, as described in Example 1.1, and data is given as mean±SD for n=1-3 rats per timepoint (except for the predose data: n=7). Dotted lines represent the minimum and maximum of predose data.

In line with the increase in FVIII activity, the physiological activated partial thrombin time (aPTT) decreased (FIG. 1E), starting immediately after administration with a peak until about day 7 p.a. as compared to vehicle-treated animals. Again, mean values ranged within the predose range, and only on day 1 p.a. mean values were below the lowest predose value of 16.5 s.

With the given exposure to rD'D3-FP for at least 14 days, a slight increase in FVIII activity was observed. A peak value was given between days 1-5 p.a., which was in any case <2-fold above saline-treated animals (FVIII chromogenic activity: maximal increase by ~1 IU/mL or 100% to ~3.5 IU/mL=350%; FVIII clotting activity: maximal increase by ~300% to ~700%, mostly by ~100% to ~500%—in line with higher baseline values in these animals as compared to men) and mostly within the physiological variation. This slight increase of FVIII activity led to a shortening of aPTT, with mean values only slightly and shortly below the minimum predose value. Thus, in healthy rats, slight increases in FVIII levels were observed at a dose of 1 mg/kg rD'D3-FP, but barley changing these values out of the physiological range.

Example 1.2: Impact of Intravenous Treatment with rD'D3-FP on Physiological Endogenous FVIII Levels in Rabbits Animals Female CHB rabbits in a weight range of 2.0-3.2 kg (Bauer, Neuental, Germany) were housed one per cage in wire-steel cages at standard housing conditions, i.e. at 20-23° C. and 50% relative humidity under a 12 h/12 h light-darkness cycle. The animals were provided tap water ad libitum and fed rabbit pellets (Deukanin®, Deutsche Tiernahrung Cremer GmbH & Co. KG, Düsseldorf, Germany). Animal husbandry and study procedures complied with the German Animal Welfare law and European Union regulations.

Experimental Details

The test articles were administered i.v. by a single injection into the lateral ear vein of the rabbits (n=3 per group). rD'D3-FP was applied at a dose level of 1, 3 or 10 mg/kg based on human albumin values. Blood samples were taken from the ear artery at pre-dose, 1, 3 and 6 h, followed by daily sampling up to 10 days post administration (p.a.) after intravenous bolus injection. They were anticoagulated using sodium citrate (1 part sodium citrate 3.13%+9 parts blood), processed to plasma and stored at approx. −70° C. for the determination of rD'D3-FP and/or FVIII activity.

rD'D3-FP exposure was determined by measurement of the albumin part of the construct using a human albumin ELISA. FVIII activity plasma levels were detected using a chromogenic assay as well as a one-stage clotting assay. Further, aPTT was quantified using the Actin® FSL test. Any clotted samples were excluded from evaluation.

Calculation of the total peak area under the curve (AUC) was done with GraphPad Prism (GraphPad Software, La Jolla, Calif., USA) over the period of 10 days using the pretreatment values as baseline and identifying peaks with a ≥30% distance from minimum to maximum values.

Figure 2A:
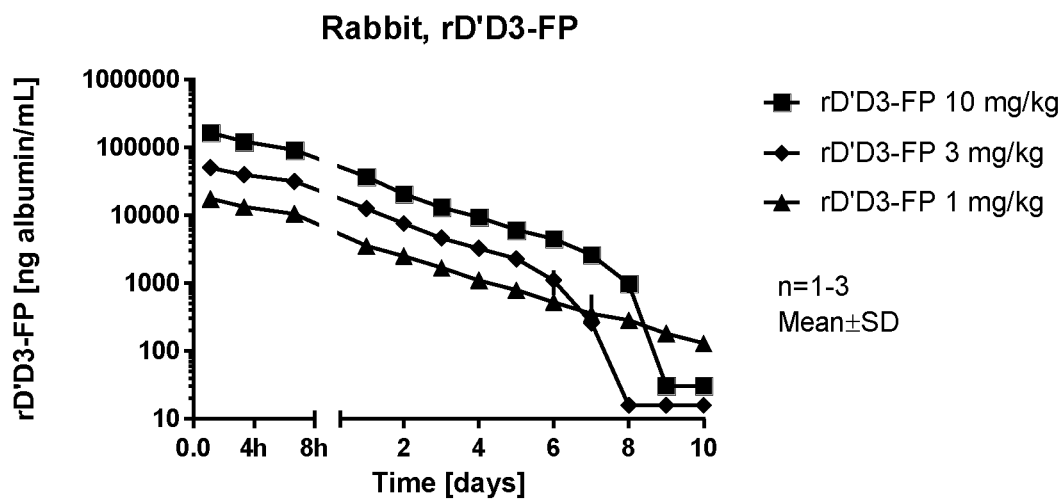
FIG. 2A shows rD'D3-FP exposure quantified via its albumin component in rabbits after i.v. administration of rD'D3-FP, as described in Example 1.2, and data is given as mean±SD for n=1-3 rabbits per timepoint.

Results rD'D3-FP was quantified up to 10 d p.a., and measured data were well above the detection limit of 16 or 31 ng/mL over the whole observation period, except for a drop observed in some animals from day 7 on or later (FIG. 2A). This sudden drop in exposure was observed in single animals, beginning on days 7-10, and especially for the higher doses. One potential cause could be the formation of anti-drug-antibodies—in line with the lower homology of the D'D3 region in rabbits and men as compared to the other species tested.

Figure 2B:
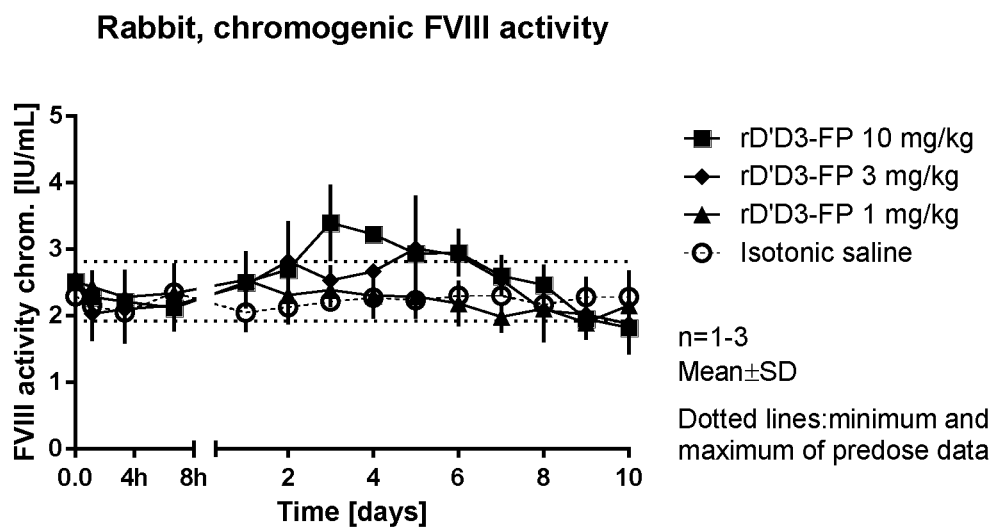
FIG. 2B shows FVIII activity quantified as chromogenic FVIII activity in IU/mL in rabbits after i.v. administration of rD'D3-FP, as described in Example 1.2, and data is given as mean±SD for n=1-3 rabbits per timepoint. Dotted lines represent the minimum and maximum of predose data.
Figure 2C:
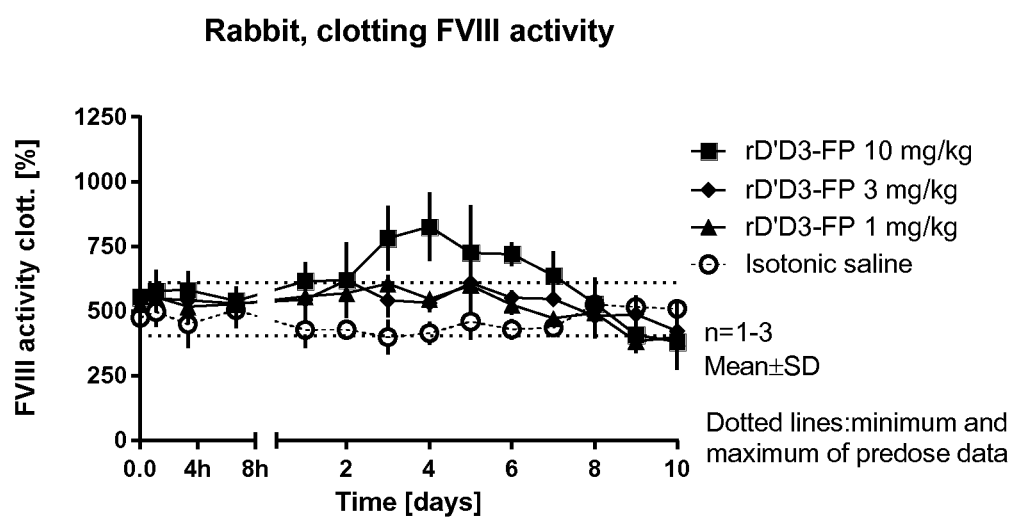
FIG. 2C shows FVIII activity quantified as clotting FVIII activity in % of the norm in rabbits after i.v. administration of rD'D3-FP, as described in Example 1.2, and data is given as mean±SD for n=1-3 rabbits per timepoint. Dotted lines represent the minimum and maximum of predose data.
Figure 2D:
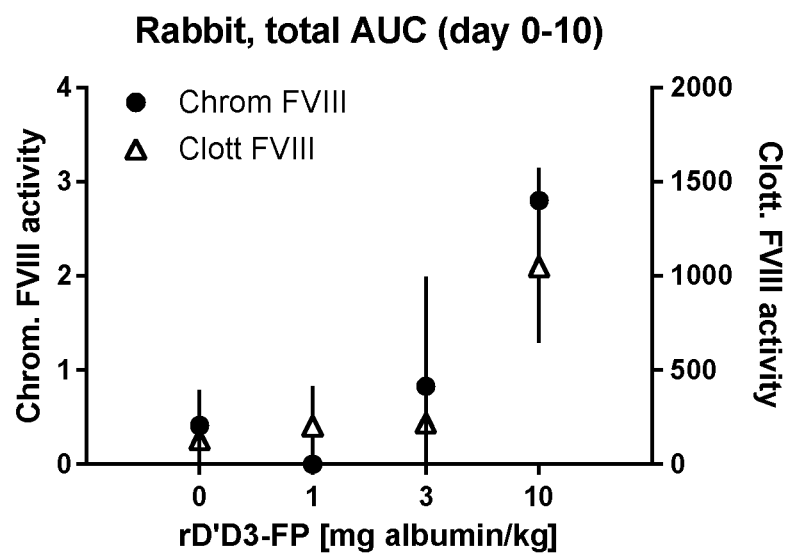
FIG. 2D shows FVIII activity quantified as chromogenic or clotting FVIII activity as above. AUC was calculated as peak area under the plasma concentration-time curve from time zero to until day 10.

FVIII activity was measured as chromogenic and one-stage clotting activity, both showing increases in endogenous levels as compared to the saline control (FIGS. 2B and 2C). The data suggest a slight increase of endogenous FVIII levels after administration of rD'D3-FP, with a peak between days 3-7 p.a. Nevertheless, the mean values only transiently increased the range of the predose values of 2.8 IU/mL in the chromogenic and 611% of the norm (6.1 IU/mL) in the clotting FVIII activity test. In line with this, AUC (evaluated over days 0 to 10 p.a.) as shown in FIG. 2D increased: with the chromogenic assay, starting at the dose of 3 mg/kg, while the effect with the clotting assay was visible only with 10 mg/kg. This is potentially related to the higher variation of baseline values in the clotting assay, which were already slightly higher in the treated groups.

Figure 2E:
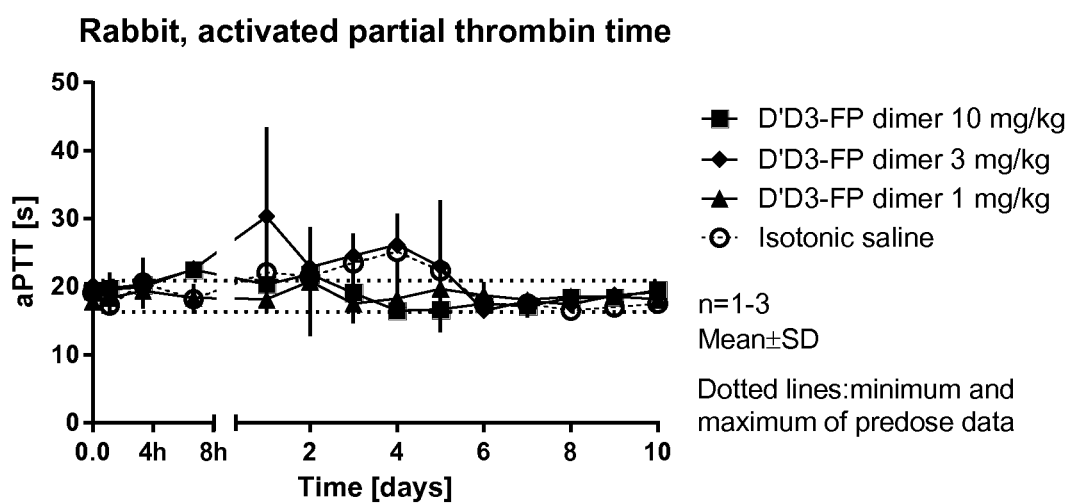
FIG. 2E shows activated partial thrombin time (aPTT) using Actin® FSL in rabbits after i.v. administration of rD'D3-FP, as described in Example 1.2, and data is given as mean±SD for n=1-3 rabbits per timepoint. Dotted lines represent the minimum and maximum of predose data.

Even though FVIII activity showed slight increases, no decrease was observed in the aPTT (FIG. 2E).

With the given exposure to rD'D3-FP for at least 6 days, a slight increase in FVIII activity was observed, which slightly exceeded levels observed in saline treated animals. A peak value was given between days 3-7 p.a., which was <2-fold above saline treated animals (FVIII chromogenic activity: maximal increase by ~1 IU/mL or 100% to ~3.5 IU/mL=350%; FVIII clotting activity: maximal increase by ~400% to ~900%—in line with higher baseline values in these animals as compared to men). These increased FVIII activity levels only slightly exceeded the physiological levels in rabbits on days 3 to 6 at a dose of 10 mg/kg, and did not reduce aPTT. Thus in healthy rabbits, only slight changes in FVIII levels were observed.

Example 1.3: Impact of Intravenous Treatment with rD'D3-FP on Physiological Endogenous FVIII Levels in Monkeys Animals Male Cynomolgus monkeys in a weight range of approximately 4-7 kg, age approximately 5-6 years (obtained from Vietnam—documentation includes health screening and any treatment administered prior to arrival—to Huntingdon Life Sciences, Cambridgeshire, UK) were housed in pairs in cages specifically designed to house non-human primates at standard housing conditions, i.e. at 15-24° C. and 40-70% relative humidity under a 12 h/12 h light-darkness cycle. The animals were provided tap water ad libitum and fed Old World Monkey Diet (200 g daily per animal) plus supplemental diet (two biscuit supplements, approximately 25 g each, and fresh fruit produce).

Experimental Details

The test articles were administered i.v. by a single injection into the saphenous vein of the monkeys (n=3 per group). rD'D3-FP was applied at a dose level of 2.5 mg/kg based on human albumin values. Blood samples were taken from the femoral vein at pre-dose, and 5, 30 min, 2, 6, 16, 30, 48, 72, 96, 120, 144, 168 hours p.a. after intravenous bolus injection. They were anticoagulated using sodium citrate (1 part sodium citrate 3.2%+9 parts blood), processed to plasma and stored at about −70° C. for the determination of FVIII activity and/or rD'D3-FP.

rD'D3-FP exposure was determined by measurement of the albumin part of the construct using an antibody capturing the D'D3 part of the molecule and using a detection antibody for albumin. FVIII chromogenic activity plasma levels were detected by the Chromogenix assay.

Figure 3A:
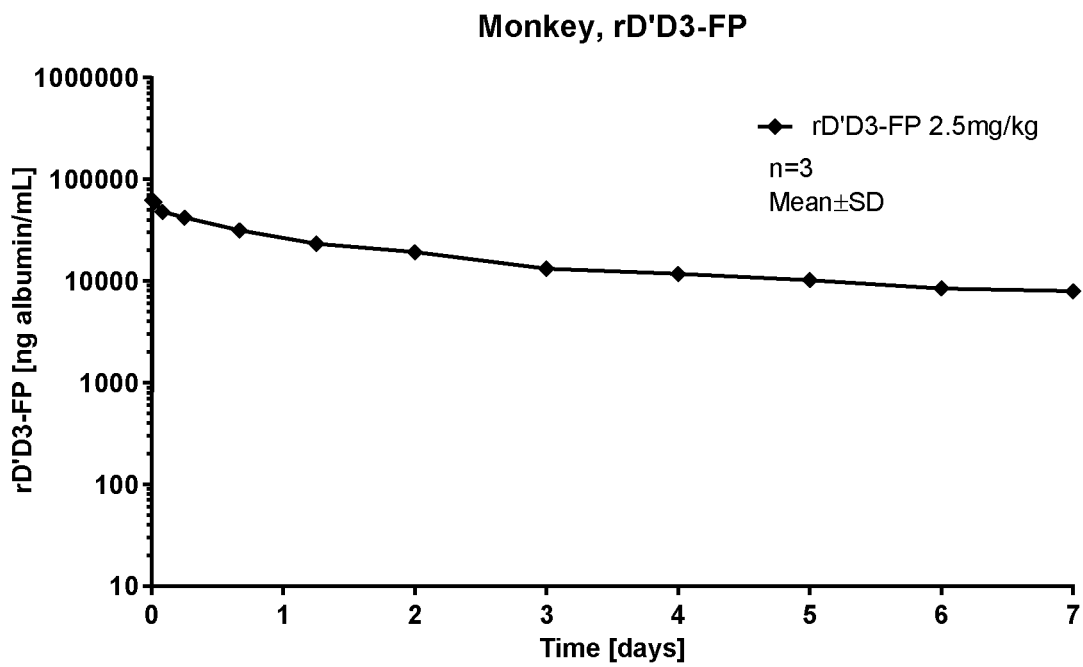
FIG. 3A shows rD'D3-FP exposure quantified against a standard quantified via its albumin component in monkeys after i.v. administration of rD'D3-FP, as described in Example 1.3, and data is given as mean±SD for n=3 monkeys per timepoint.

Results rD'D3-FP was quantified using an ELISA binding to both of its components, albumin and D'D3, and measurements were performed up to 168 h (7 d) p.a. Measured data were well above the detection limit over the whole observation period (FIG. 3A).

Figure 3B:
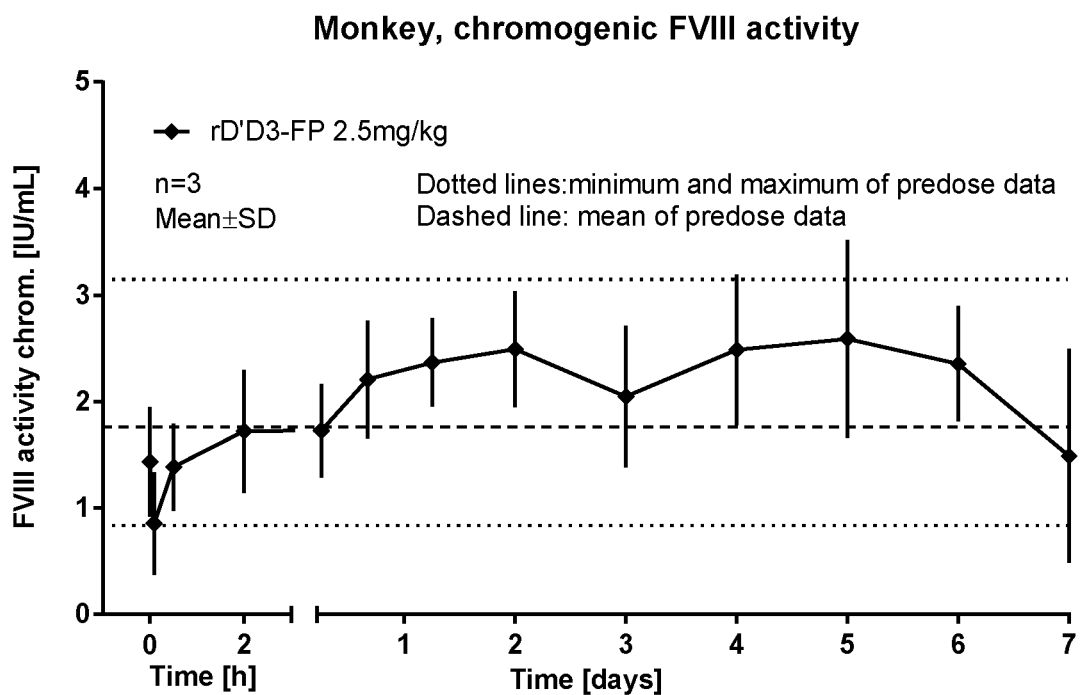
FIG. 3B shows FVIII activity quantified as chromogenic FVIII activity in % of the norm in monkeys after i.v. administration of rD'D3-FP, as described in Example 1.3, and data is given as mean±SD for n=3 monkeys per timepoint. Dotted lines represent the minimum and maximum of predose data, the dashed line represents the mean of predose data (predose data: n=22).

FVIII activity was measured as chromogenic activity as shown in FIG. 3B. Basal endogenous levels varied relevantly, with a range of 83.6-314.8% of the norm (0.8-3.1 IU/mL=dotted lines in FIG. 3B) and a mean 176.4% of the norm (1.8 IU/mL, dashed line in FIG. 3B). As in rats and rabbits, only a small increase of endogenous FVIII levels up to a mean maximum of 258.9% of the norm was observed, and variability was quite high. Nevertheless, an increase in endogenous FVIII levels by up to ~1 IU/mL or ~100% of the norm (to ~2.5 IU/mL or ~2.5 IU/mL—in line with higher baseline values in these animals as compared to men) as compared to the individual pre-dose values was demonstrated, which (as mean) nevertheless did not exceed the physiological FVIII levels of monkeys.

Example 1.4: Impact of Intravenous Treatment with rD'D3-FP on Endogenous FVIII Levels in VWF Ko Rats Animals Male and female VWF ko rats in a weight range of 261-598 g were breed at Charles River Laboratories (Sulzfeld, Germany). In house, the animals were kept at standard housing conditions, i.e. at 20-24° C. under a 12 h/12 h light-darkness cycle. Animals were fed ad libitum with standard mouse and rat diet (Ssniff-Versuchsdiäten, Soest, Germany). Tap water was supplied ad libitum. Animal husbandry and study procedures complied with the German Animal Welfare law and European Union regulations.

The group size of the 1 and 10 mg/kg groups was n=9, divided in 3 cohorts, except for the control (n=3 animals only). Thus, n=3 animals per time-point were used for all vehicle, 1 and 10 mg/kg rD'D3-FP timepoints. For the 3 mg/kg group, the group size was n=4 per timepoint.

Experimental Details

The test articles were administered i.v. by a single injection into the lateral tail vein at a total volume of 2 or 3 mL/kg. rD'D3-FP was applied at dose levels at 1, 3 or 10 mg/kg based on human albumin values. Blood samples were taken retroorbitally under short term anaesthesia at predose, 6, 24, 48, 72, 96, 120, 168, 240, 336 h (1 and 10 mg/kg) p.a. using an alternating sampling scheme, or from each individual animal from the saphenous vein at predose, 1, 24, 48, 72, 120, 192, 240 and 336 h p.a. (3 mg/kg). The PK profile was taken from three cohorts of rats per group (1 and 10 mg/kg) or from individual animals (3 mg/kg). Blood samples were anticoagulated using sodium citrate (1 parts sodium citrate 3.13%+9 parts blood), processed to plasma and stored at −70° C. for the determination of FVIII activity and/or albumin.

rD'D3-FP exposure was determined by measurement of the albumin part of the construct using a human albumin ELISA. Further, FVIII chromogenic and clotting activity as well as aPTT was measured (the latter only in groups treated with 1 and 10 mg/kg rD'D3-FP).

Calculation of the area under the curve (AUC) was done with MATLAB R2017a (Natick, Mass., USA) using trapezoidal method from zero to day 10.

Figure 4A:
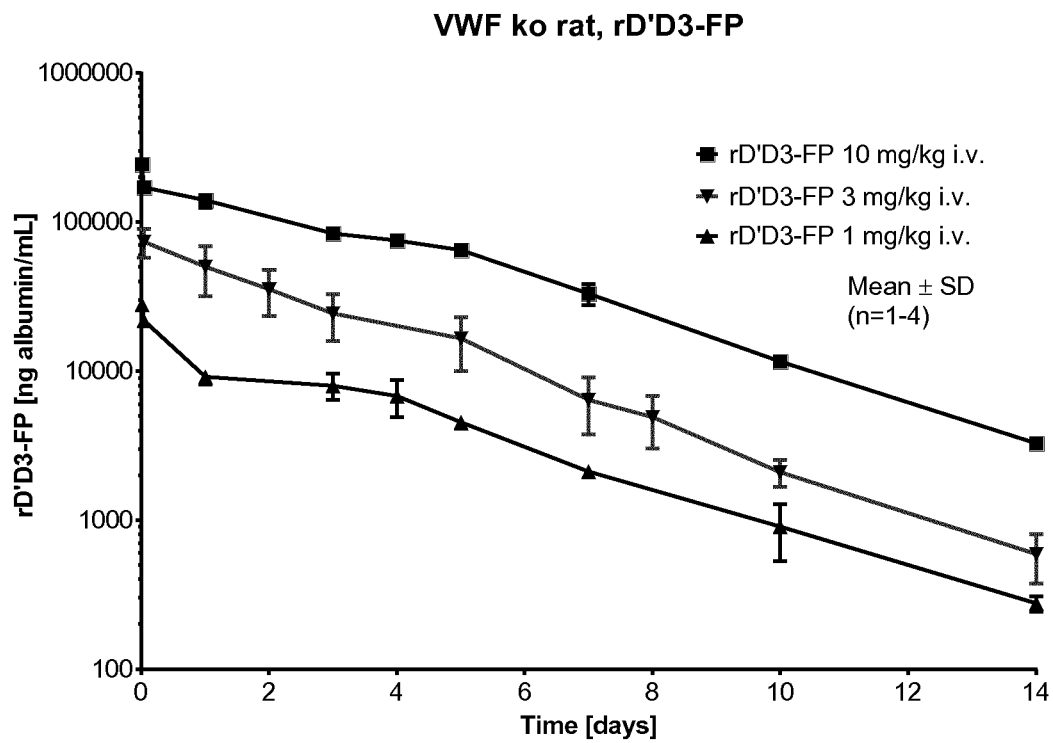
FIG. 4A shows rD'D3-FP exposure quantified via its albumin component in VWF knockout rats after i.v. administration of rD'D3-FP, as described in Example 1.4, and data is given as mean±SD for n=1-4 rats per timepoint.

Results rD'D3-FP was quantified using an ELISA against human albumin, and measurements were performed up to 14 d p.a. All measured data were well above the detection limit over the whole observation period up to day 14 (FIG. 4A). A linear dose-dependency was shown from 1-10 mg/kg rD'D3-FP.

Figure 4B:
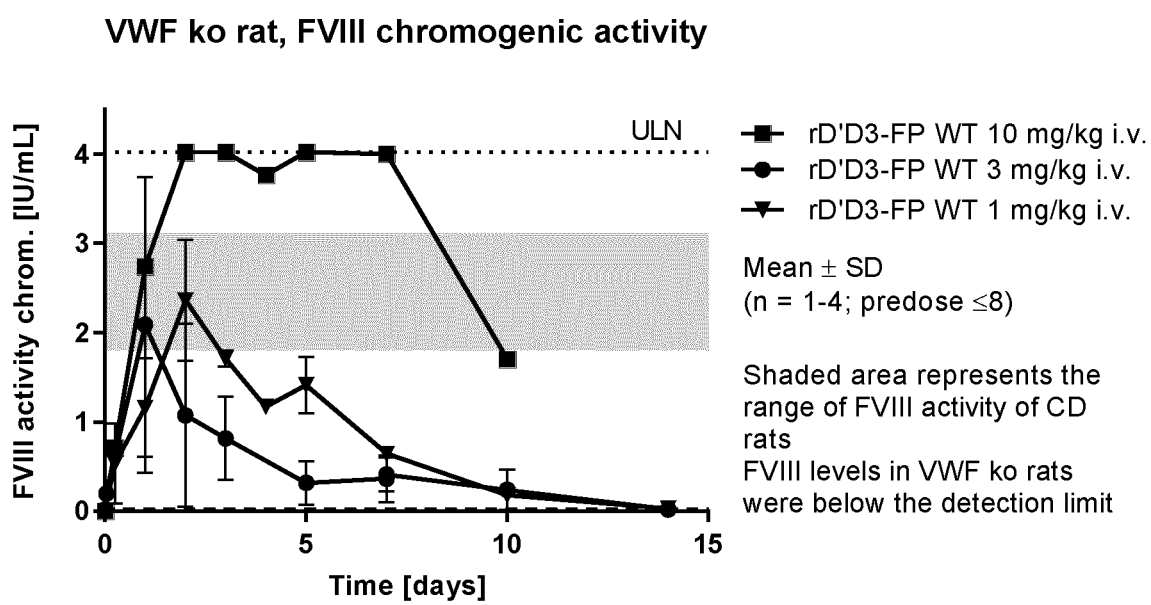
FIG. 4B shows FVIII activity quantified as chromogenic FVIII activity in IU/mL in VWF knockout rats after i.v. administration of rD'D3-FP, as described in Example 1.4, and data is given as mean±SD for n=1-4 rats per timepoint (except for the predose data: n≤8). Predose data in VWF ko rats is below the limit of quantification. The shaded area represents the minimum and maximum of predose data from healthy CD rats; dotted lines marked as ULN represent the upper limit of normal.

FVIII activity measured as chromogenic activity as shown in FIG. 4B did not give relevant baseline FVIII levels: 22 of 23 samples were below the limit of detection (0.005 IU/mL or 0.5%) and one animal had a value of 0.007 IU/mL. In the VWF ko rats (in contrast to the CD rats), the upper limit of normal (ULN, 4 IU/mL) was reached with the dilution of 1:4 used for quantification of the samples of both rat strains: After administration of rD'D3-FP, levels increased within 2 days, with the 10 mg/kg dose even exceeding the upper limit of quantification of the assay of 4 IU/mL (or 400%). In VWF ko rats, the FVIII activity levels after dosing of 10 mg/kg—but not 1 or 3 mg/kg—rD'D3-FP transiently exceeded the values measured in healthy CD rats. FVIII chromogenic activity values were after administration of 10 mg/kg rD'D3-FP also higher than in the other healthy species, i.e. rabbits (dosed up to 10 mg/kg rD'D3-FP) or monkeys (2.5 mg/kg rD'D3-FP). The effect in rats after administration of 10 mg/kg rD'D3-FP lasted up to 10 days. Even at a dose of 1 mg/kg rD'D3-FP, a highest plasma concentration of 2.36 IU/mL (or 236%) was reached on day 2, and the effect was still weakly seen on day 7. Similarly with 3 mg/kg rD'D3-FP, a highest FVIII plasma concentration was reached on day 1 (2.09 IU/mL or 209%). With these lower 2 doses, the mean FVIII concentrations were just within the range of normal levels from CD rats.

Figure 4C:
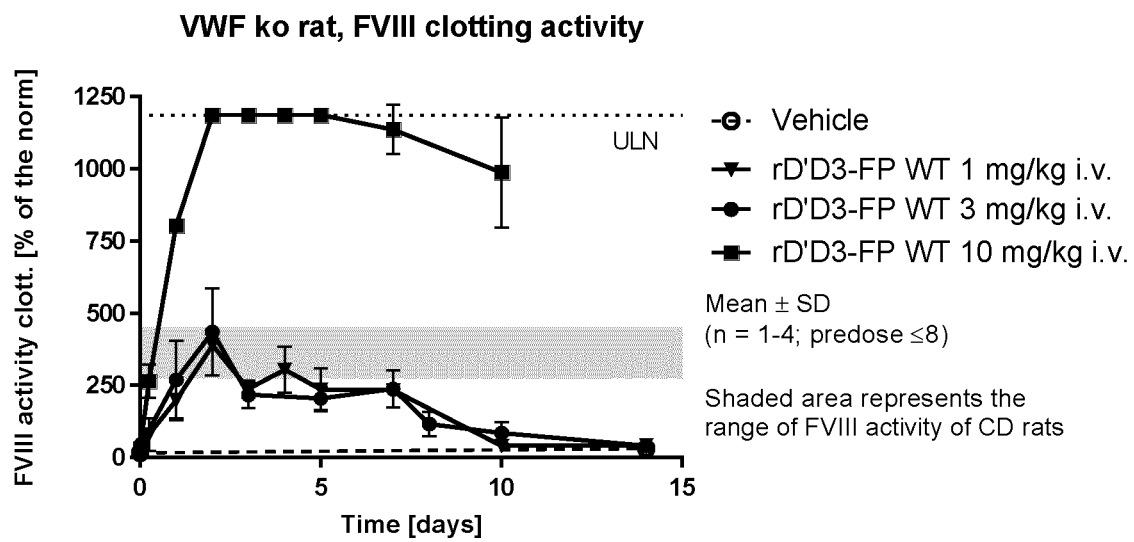
FIG. 4C shows FVIII activity quantified as clotting FVIII activity in % of the norm in VWF knockout rats after i.v. administration of rD'D3-FP, as described in Example 1.4, and data is given as mean±SD for n=1-4 rats per timepoint (except for the predose data: n≤8). The shaded area represents the minimum and maximum of predose data from healthy CD rats; dotted lines marked as ULN represent the upper limit of normal.

When FVIII activity was measured with the clotting assay as depicted in FIG. 4C, baseline FVIII levels were measurable (undiluted samples: mean 22.3%, minimum 11.7% and maximum 40.9% of the norm, n=17; and with a detection limit of 40%, 20 samples remained <40%). Thus, as in CD rats and rabbits, baseline values were highly variable. It needs to be mentioned that all samples after administration of rD'D3-FP needed a dilution step of 1:8, thereby generating an ULN of 1186.4% of the norm. Again, after administration of rD'D3-FP at a dose of 10 mg/kg, endogenous FVIII levels increased within 2 days even over the ULN of the assay, i.e. higher than in rabbits. This effect lasted up to 14 days at the high dose of 10 mg/kg rD'D3-FP. Even at a dose of 1 mg/kg, a highest plasma concentration of 388.8% of the norm was reached on day 2, and the effect was still seen on day 7. Similarly at a dose of 3 mg/kg, the highest plasma concentration measured on day 2 was 435.2% of the norm. Similar to the chromogenic FVIII activity, the physiological range of FVIII activity was exceeded after administration of 10 mg/kg and just reached after administration of 1 or 3 mg/kg rD'D3-FP.

Thus, chromogenic and clotting activity data are in line, with clotting activity data showing slightly stronger responses, assumingly related to the measurement of baseline rat FVIII against a human FVIII standard. An increase in FVIII activity was observed, which reached levels observed in healthy CD rats (1 and 3 mg/kg) or exceeded them (10 mg/kg). For the 10 mg/kg dose, peak values were above the upper detection limit, thus an x-fold increase above normal ranges could not be determined.

Figure 4D:
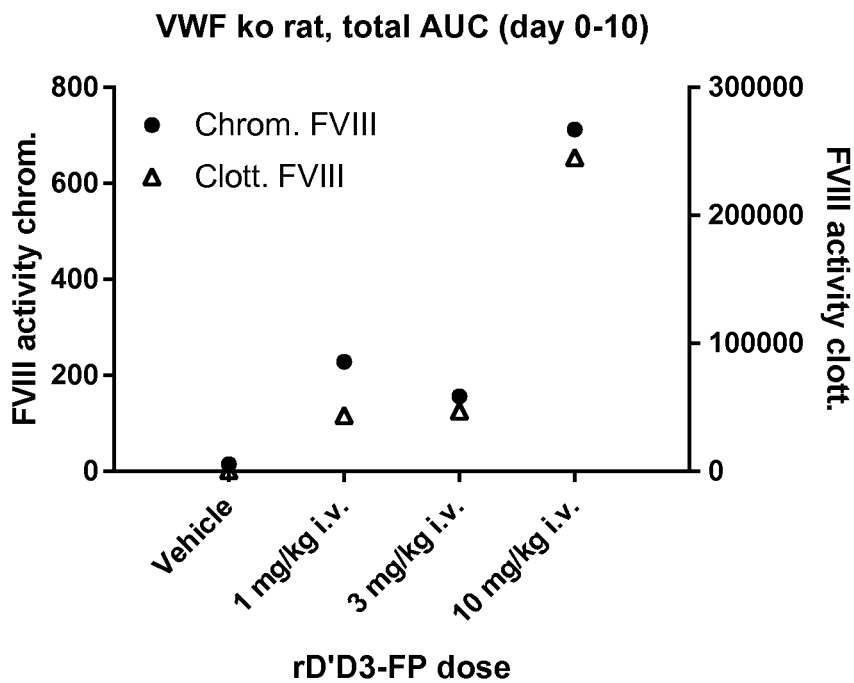
FIG. 4D shows FVIII activity quantified as chromogenic or clotting FVIII activity as above. AUC was calculated as peak area under the plasma concentration-time curve from time zero to until day 10.

This is in line with the calculated increases in AUC (day 0-10), showing increases after a dose of 1, 3 and 10 mg/kg rD'D3-FP as depicted in FIG. 4D. Increases after doses with 1 and 3 mg/kg rD'D3-FP were ~10-fold for chromogenic and ~80-fold for clotting FVIII activity as compared to vehicle treatment, while those with 10 mg/kg rD'D3-FP reached ~50-fold for chromogenic and 430-fold effects on $AUC_{0-10d}$.

Figure 4E:
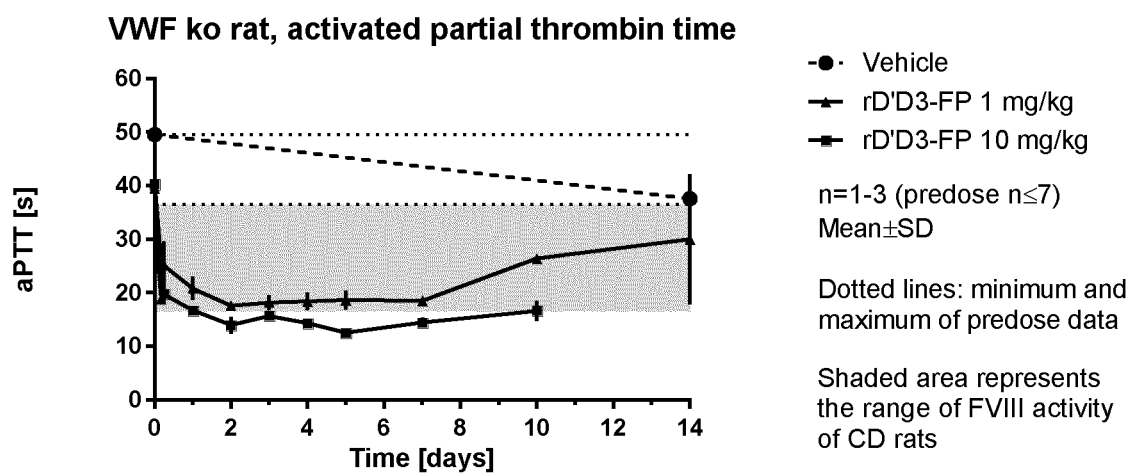
FIG. 4E shows activated partial thrombin time (aPTT) using Pathromtin® SL in VWF knockout rats after i.v. administration of rD'D3-FP, as described in Example 1.4, and data is given as mean±SD for n=1-3 rats per timepoint (except for the predose data: n≤7). Dotted lines represent the minimum and maximum of predose data of the VWF ko rats. The shaded area represents the minimum and maximum of predose data from healthy CD rats.

In line with these increases in FVIII levels, activated partial thrombin time (aPTT) decreased relevantly from pathological predose or vehicle data to a lowest mean value of 12.5 s in the 10 mg/kg rD'D3-FP dose group (FIG. 4E). This decrease lasted in both measured dose groups (1 and 10 mg/kg) up to 14 days, and brought the aPTT values in (1 mg/kg rD'D3-FP) or slightly below (10 mg/kg rD'D3-FP) a range observed in healthy CD rats (range 16.5-36.6 s).

Example 1.5: Impact of Intravenous Treatment with rD'D3-FP on Endogenous FVIII Levels in VWF Ko Mice Animals Male and female VWF ko mice in a weight range of 30-45 g were breed at Charles River Laboratories (Sulzfeld, Germany). In house, the animals were kept at standard housing conditions, i.e. at 20-24° C. under a 12 h/12 h light-darkness cycle. Animals were fed ad libitum with standard mouse and rat diet (Ssniff-Versuchsdiäten, Soest, Germany). Tap water was supplied ad libitum. Animal husbandry and study procedures complied with the German Animal Welfare law and European Union regulations.

The group size was n=12, divided in 4 cohorts, except for the control (n=4 animals). Thus, n=3-4 animals per time-point were used.

Experimental Details

The test articles (rD'D3-FP or vehicle (isotonic saline)) were administered i.v. by a single injection into the lateral tail vein at a total volume of 5 mL/kg. rD'D3-FP was applied at a dose level of 10 mg/kg based on human albumin values. Blood samples were taken retroorbitally under short term anaesthesia at 4, 7, 16, 24, 48, 72, 96 and 168 h p.a. using an alternating sampling scheme from the rD'D3-FP-dosed animals, and at 4 and 168 h p.a. from the vehicle-treated animals. The PK profile was taken from four cohorts of mice per group. Blood samples were anticoagulated using sodium citrate (1 parts sodium citrate 3.13%+9 parts blood), processed to plasma and stored at −70° C. for the determination of FVIII activity and/or albumin.

rD'D3-FP exposure was determined by measurement of the albumin part of the construct using a human albumin ELISA. Further, FVIII chromogenic and clotting activities were measured.

Calculation of the total peak area under the curve (AUC) was done with GraphPad Prism (GraphPad Software, La Jolla, Calif., USA) over the period of 7 days identifying peaks with a ≤10% distance from minimum to maximum values.

Figure 5A:
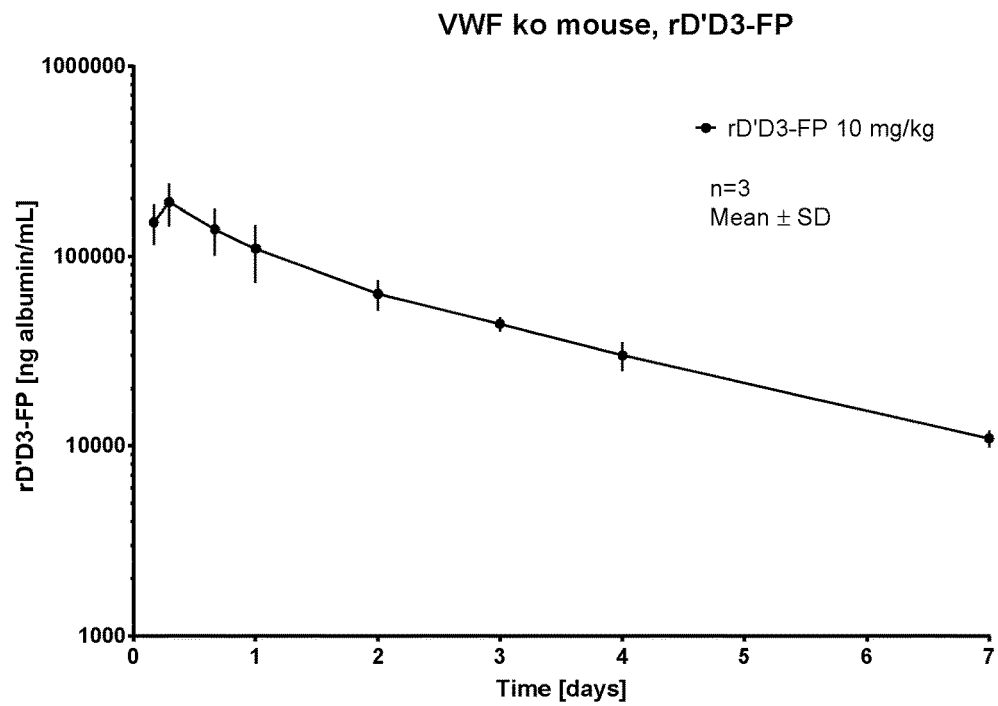
FIG. 5A shows rD'D3-FP exposure quantified via its albumin component in VWF knockout mice after administration of rD'D3-FP, as described in Example 1.5, and data is given as mean±SD for n=3 mice per timepoint.

Results rD'D3-FP was quantified using an ELISA against human albumin, and measurements were performed up to 7 d p.a. All measured data were well above the detection limit over the whole observation period (FIG. 5A).

FVIII activity measured as chromogenic activity did not give relevant baseline FVIII levels: all 6 measured samples from vehicle-treated animals were below the limit of detection (10 mIU/mL or 1%). For comparison, chromogenic activity of healthy NMRI mice ranged at about 96-300 mIU/mL, median 230 mIU/mL, mean 206 mIU/mL (range 10-30% of the norm, unpublished data), i.e. lower than observed in other animal species or men.

Figure 5B:
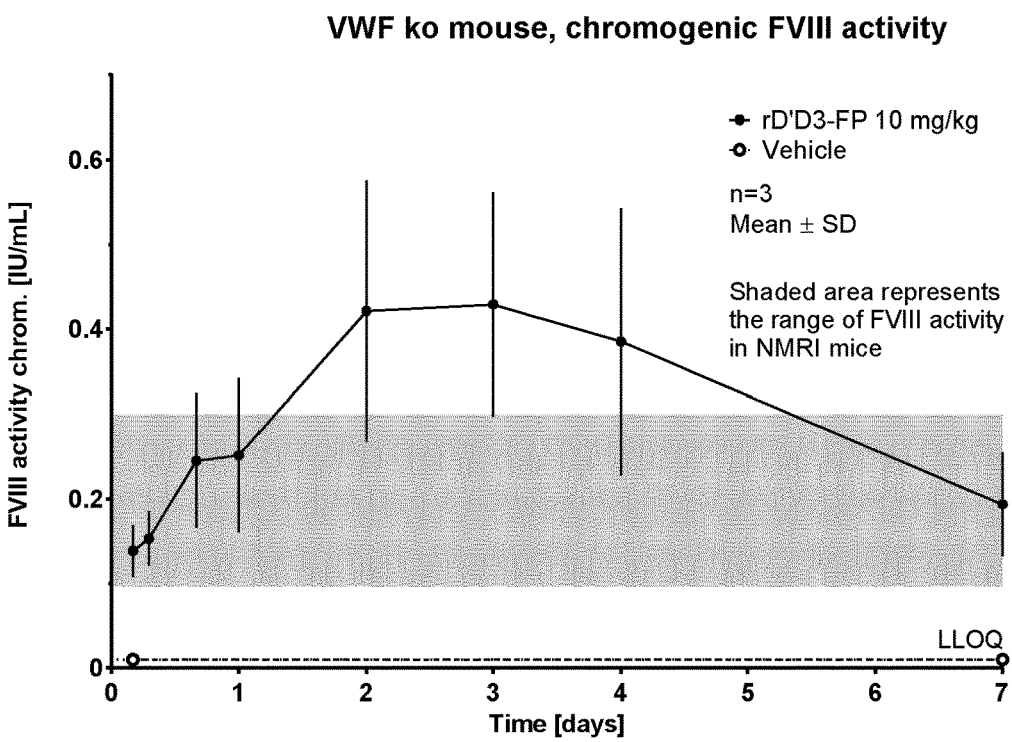
FIG. 5B shows FVIII activity quantified as chromogenic FVIII activity in mIU/mL in VWF knockout mice after administration of rD'D3-FP, as described in Example 1.5, and data is given as mean±SD for n=3 mice per timepoint. Vehicle data in VWF ko mice is below the limit of quantification (LLOQ). The shaded area represents the minimum and maximum of predose data from healthy NMRI mice.

According to FIG. 5B, after administration of rD'D3-FP, levels increased quickly within 4 hours to a mean value of 138 mU/mL (14%), and increased further, reaching a maximum at 48 h p.a., with a mean of 421 mU/mL (42%) to 72 h p.a. (429 IU/mL or 43%). At the last time-point at 168 h (7 d) p.a., still 194 mU/mL (20%) were measured. With this, FVIII chromogenic activity after treatment with 10 mg/kg rD'D3-FP slightly exceeded physiological FVIII plasma levels as measured in NMRI mice, and effects were comparable to VWF ko rats.

Figure 5C:
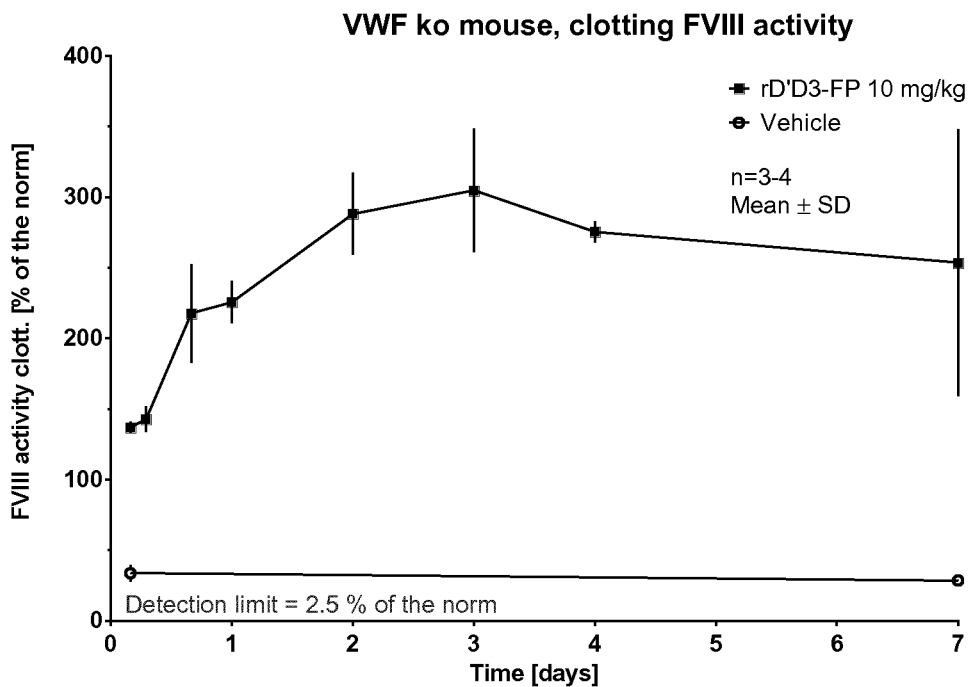
FIG. 5C shows FVIII activity quantified as clotting FVIII activity in % of the norm in VWF knockout mice after administration of rD'D3-FP, as described in Example 1.5, and data is given as mean±SD for n=3-4 mice per timepoint. Vehicle data in VWF ko mice is below the detection limit.

When FVIII activity was measured with the clotting assay, baseline FVIII levels were measurable (vehicle-treated animals: mean 31.1, minimum 25.8 and maximum 41.8% of the norm, n=8). Thus, as in the other species, baseline values were highly variable. Again, after administration of rD'D3-FP, levels increased quickly as depicted in FIG. 5C, and could only be measured in a dilution of 1:60 (while vehicle-treated animals, used for the quantification of baseline values, were measured with a dilution of 1:10). At the first sampling point of 4 h p.a., mean values were already at 137% of the norm, and increased further up to 16 h p.a., with a mean of 218% of the norm. The maximum exposure was reached at 72 h p.a. with a mean of 304% of the norm. At the last time-point at 168 h (7 d) p.a., still 254% of the norm were measured.

Figure 5D:
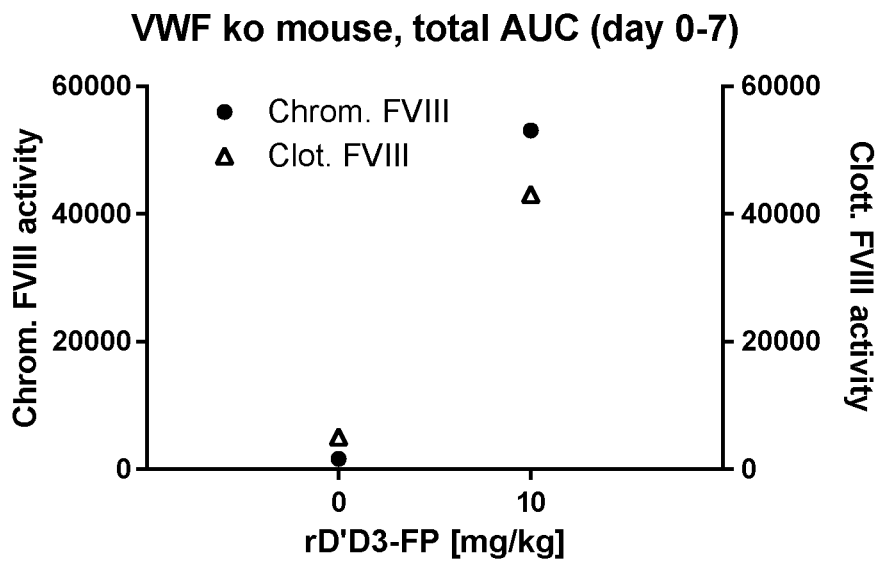
FIG. 5D shows FVIII activity quantified as chromogenic or clotting FVIII activity as above. AUC was calculated as peak area under the plasma concentration-time curve from time zero to until day 7.

Thus, chromogenic and clotting activity data were generally in line, with clotting activity data showing stronger responses, assumingly related to the measurement of mouse FVIII (in VWF ko animals) against a human FVIII standard. An increase in FVIII activity was observed, which exceeded levels observed in healthy NMRI mice <2-fold (FVIII chromogenic activity: maximal increase by 0.1 IU/mL=~10% to ~0.4 IU/mL=40%—in line with lower baseline values in these animals as compared to men; FVIII clotting activity: maximal increase to ~300% (no range from NMRI mice determined)). This is in line with the calculated increases in AUC (day 0-7), showing large increases after a dose of 10 mg/kg rD'D3-FP as compared to vehicle treated animals as depicted in FIG. 5D.

Example 1.6: Impact of Intravenous Treatment with Different rD'D3 Polypeptides on Endogenous FVIII Levels in VWF Ko Rats Animals Male and female VWF ko rats in a weight range of 261-559 g were breed at Charles River Laboratories (Sulzfeld, Germany). In house, the animals were kept at standard housing conditions, i.e. at 20-24° C. under a 12 h/12 h light-darkness cycle. Animals were fed ad libitum with standard mouse and rat diet (Ssniff-Versuchsdiäten, Soest, Germany). Tap water was supplied ad libitum. Animal husbandry and study procedures complied with the German Animal Welfare law and European Union regulations.

The group size was n=4 for each group.

Experimental Details

The test articles were administered i.v. by a single injection into the lateral tail vein at a total volume of 3 mL/kg. rD'D3-FP was applied at a dose level of 3 mg/kg based on human albumin values. Blood samples were taken from the saphenous vein at pre-dose, 1, 24, 48, 72, 120, 192, 240 and 336 h p.a. from the rD'D3-FP-dosed animals, and at pre-dose, 1, 24, 48, 72, 96, 168, 240 and 336 h from the rD'D3-CTP treated animals. Blood samples were anticoagulated using sodium citrate (1 parts sodium citrate 3.13%+9 parts blood), processed to plasma and stored at −70° C. for the determination of FVIII activity and/or albumin.

rD'D3-FP exposure was determined by measurement of the albumin part of the construct using a human albumin ELISA. rD'D3-CTP was measured by an ELISA technique using antibodies against anti-human D'D3. Further, FVIII chromogenic and clotting activities were measured.

Calculation of the area under the curve (AUC) from 0 to day 10 was done with MATLAB R2017a (Mathworks, Natick, Mass., USA) using the trapezoidal method.

Figure 6A:
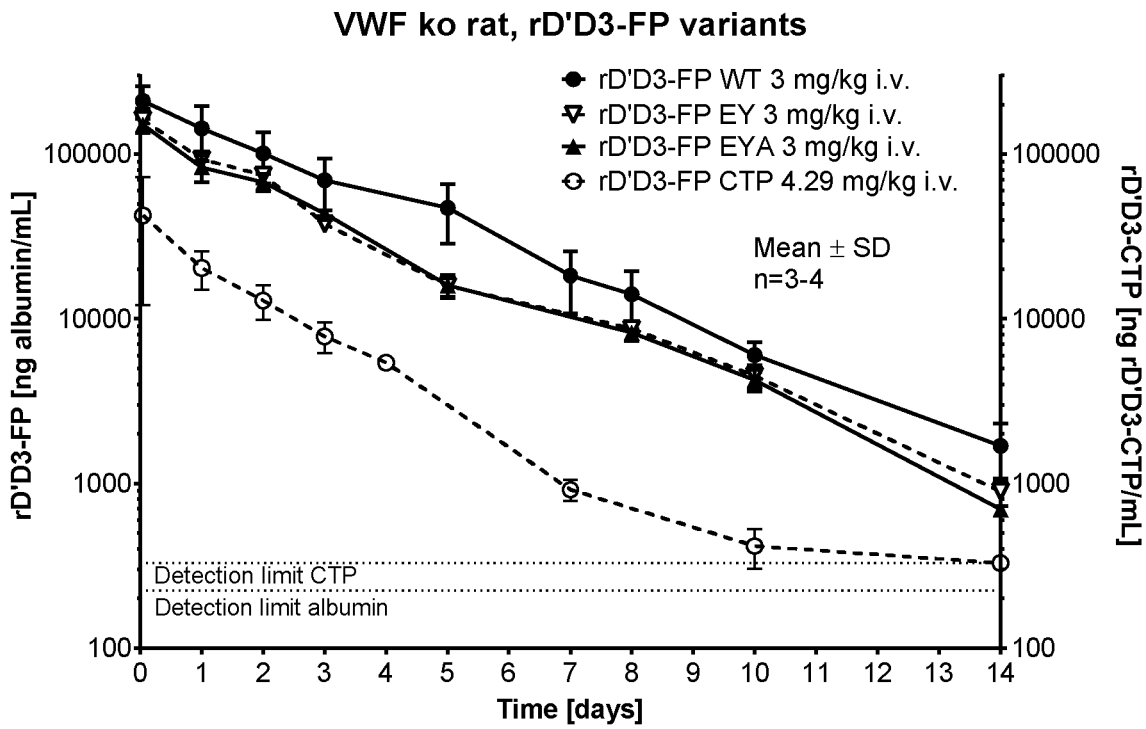
FIG. 6A shows rD'D3-FP WT, rD'D3-FP EY, rD'D3-FP EYA or rD'D3-CTP quantified in VWF knockout (ko) rats via its albumin component (rD'D3-FP) or via the D'D3 component (rD'D3-CTP) after i.v. administration of rD'D3 variants, as described in Example 1.6, and data is given as mean±SD for n=3-4 rats per timepoint. The dotted lines represent the detection limit for albumin and rD'D3-CTP, respectively.

Results rD'D3-FP was quantified using an ELISA against human albumin, and measurements were performed up to 14 d p.a. All measured data of the rD'D3-FP variants were well above the detection limit over the whole observation period, while rD'D3-CTP reached baseline values on day 14 (FIG. 6A). A slight advantage of rD'D3-FP WT was observed in recovery as compared to the variants EY and EYA, but no relevant difference was seen with regard to clearance. rD'D3-CTP was quantified using an ELISA against human rD'D3 and measurements were well above the detection limit until and including d 10 p.a. (FIG. 6A).

Figure 6B:
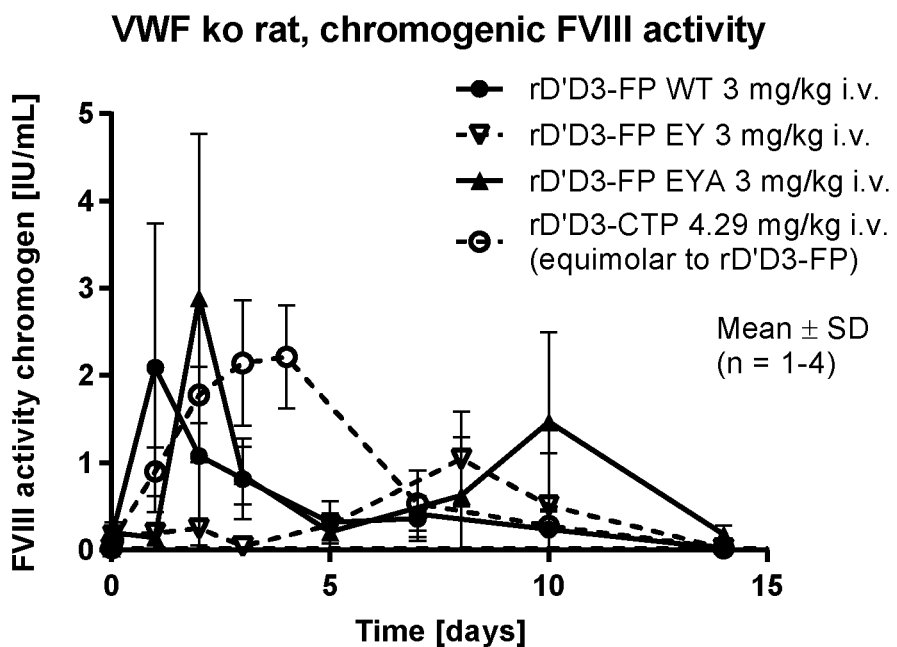
FIG. 6B shows FVIII activity quantified as chromogenic FVIII activity in mIU/mL in VWF ko rats after i.v. administration of rD'D3 variants, as described in Example 1.6, and data is given as mean±SD for n=1-4 rats per timepoint.
Figure 6C:
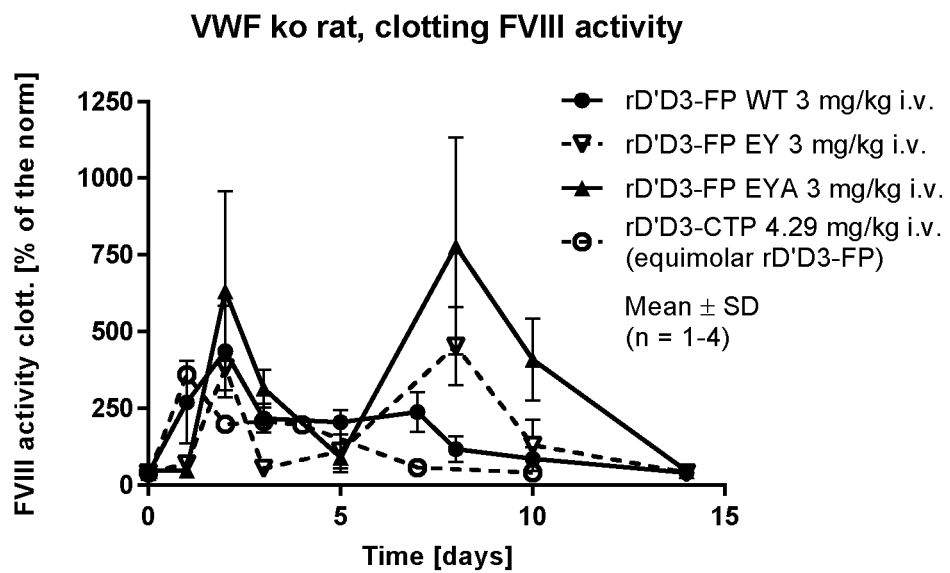
FIG. 6C shows FVIII activity quantified as clotting FVIII activity in % of the norm in VWF ko rats after i.v. administration of rD'D3 variants, as described in Example 1.6, and data is given as mean±SD for n=1-4 rats per timepoint.
Figure 6D:
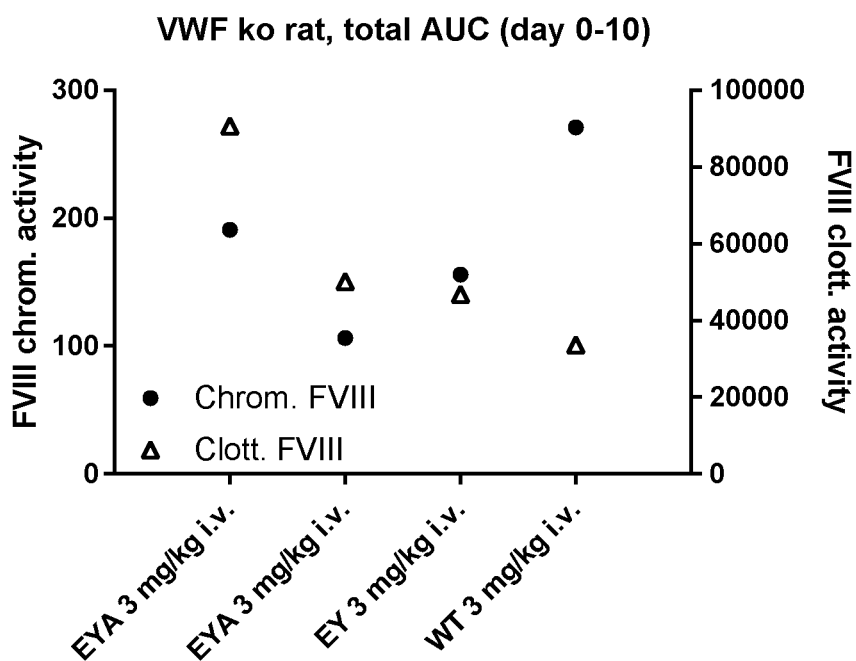
FIG. 6D shows FVIII activity quantified as chromogenic or clotting FVIII activity as above. AUC was calculated as peak area under the plasma concentration-time curve from time zero to until day 10.

FVIII activity measured as chromogenic activity did not give relevant baseline FVIII levels: all 18 measured predose samples were below the limit of detection (20 mIU/mL or 2%). According to FIG. 6B, after administration of rD'D3-FP variants, levels increased already at 1 h p.a. (WT 197±20 mIU/mL or 5%, EY 171±84 mIU/mL or 17%, EYA 203±117 mIU/mL or 20% and CTP 110±102 mIU/mL or 11%) and even further at the next measured timepoints. A maximum was reached between day 1 to day 8 with means of 2088 mU/mL (209%) for WT, of 2889 mU/mL (289%) for EY, of 1044 mU/mL (104%) for EYA, and of 2214 mU/mL (221%) for CTP. The last measurable FVIII activity was observed for WT at day 10 (237±225 mU/mL (24%)), for EY at day 10 (512±603 mU/mL (51%)), for EYA at day 14 (last measured timepoint, 179±107 mU/mL (18%), and for CTP at day 14 (22±4 mU/mL (2%)). This led to highest observed $AUC_{0-10d}$ after i.v. administration for the rD'D3-CTP variant (Tab. 2, FIG. 6D).

When FVIII activity was measured with the clotting assay, baseline FVIII levels were also not measurable (n=20 predose treated animals, detection limit 40%). As depicted in FIG. 6C, again, after administration of rD'D3-HLP, levels increased already at 1 h p.a. (WT 47±4%, EY 41±1%, EYA 45±5% and CTP 40±1%) and even further at the next measured timepoints. A maximum was reached between day 1 to day 8 with means of 435% for WT, of 453% for EY, of 779% for EYA, and of 358% for CTP. The last measurable FVIII activity was observed for WT at day 10 (85±39%), for EY at day 10 (130±84%), for EYA at day 14 (last measured timepoint, 46±7%), and for CTP at day 7 (57±29%). The highest observed $AUC_{0-10d}$ was achieved after i.v. administration with rD'D3-FP EYA (Tab. 2, FIG. 6D).

Thus, chromogenic and clotting activity data were generally in line, again with clotting activity data showing stronger responses. An increase in FVIII activity was observed to about 1.5-2 IU/mL (150-200%) for chromogenic FVIII activity and to ~300-700% for clotting activity, and thus slightly below values in CD rats for chromogenic FVIII activity and slightly above values in CD rats for clotting FVIII activity (see FIG. 4B and FIG. 4C in example 1.4)—in line with baseline values in these animals differing from those of men.

TABLE 2

| $AUC_{0-10\,d}$ of rD'D3 and FVIII activity after i.v. administration of rD'D3 variants in VWF ko rat | | |
|---|---|---|
| | FVIII chromogenic activity $AUC_{0-10d}$ [h * IU/mL] | FVIII clotting activity $AUC_{0-10d}$ [h * %/mL] |
| rD'D3-FP WT 3 mg/kg i.v. | 156 | 46789 |
| rD'D3-FP EY 3 mg/kg i.v. | 106 | 50101 |
| rD'D3-FP EYA 3 mg/kg i.v. | 191 | 90633 |
| rD'D3-CTP 3 mg/kg i.v. | 271 | 33542 |

Thus, chromogenic and clotting activity data were generally in line, with clotting activity data showing higher absolute FVIII concentrations related to higher absolute $AUC_{0-10d}$ values. It shall be mentioned that effects on FVIII activity were stronger after rD'D3-CTP administration in the chromogenic as compared to the clotting assay. While all 4 rD'D3-FP variants showed about comparable exposure, the rD'D3-FP EYA variant with the highest binding affinity to FVIII showed longest and highest effects on endogenous FVIII.

Example 1.7: Subcutaneous Availability of rD'D3-FP in FVIII Ko, VWF Ko and NMRI Mice, VWF Ko and CD Rats and Pigs, and its Impact on Endogenous FVIII Levels in VWF Ko Rats and Pigs Animals FVIII Ko Mice Male and female FVIII ko mice in a weight range of 20-30 g were breed at Charles River Laboratories (Sulzfeld, Germany). The group size was n=12, divided in 4 cohorts. Thus, n=3 animals per time-point were used.

VWF Ko Mice

Male and female VWF ko mice in a weight range of 25-40 g were breed at Charles River Laboratories (Sulzfeld, Germany). The group size was n=12, divided in 4 cohorts. Thus, n=3 animals per time-point were used.

NMRI Mice

Female NMRI mice in a weight range of 27-34 g were breed at Charles River Laboratories (Sulzfeld, Germany). The group size was n=12, divided in 4 cohorts. Thus, n=3 animals per time-point were used.

CD Rats

Female rats Crl:CD (Sprague Dawley) in a weight range of 250-302 g were breed at Charles River Laboratories (Sulzfeld, Germany). The group size was n=6, divided in 2 cohorts. Thus, n=3 animals per time-point were used.

VWF Ko Rats

Male and female VWF ko rats in a weight range of 222-559 g were bred at Charles River Laboratories (Sulzfeld, Germany). The group size was n=4.

In house, mice and rats were kept at standard housing conditions, i.e. at 20-24° C. under a 12 h/12 h light-darkness cycle. Animals were fed ad libitum with standard mouse and rat diet (Ssniff-Versuchsdiäten, Soest, Germany). Tap water was supplied ad libitum. Animal husbandry and study procedures complied with the German Animal Welfare law and European Union regulations.

Pigs

Pigs were chosen, since they represent a good model for subcutaneous bioavailability with respect to its predictivity for men. The group size was 2 (intravenous) or 3 (subcutaneous).

Male pigs in a weight range of 23-27 kg were breed at Schlosser (Schwalmtal, Germany). In house, the animals were kept in a stable on straw at 18-21° C. Animals were fed with bruised grain. Tap water was supplied ad libitum. Animal husbandry and study procedures complied with the German Animal Welfare law and European Union regulations.

Experimental Details

FVIII Ko, VWF Ko and NMRI Mice

The test articles were administered i.v. by a single injection into the lateral tail vein at a total volume of 5 mL/kg or s.c. by a single injection into the neck at a total volume of 5 mL/kg. Blood samples were taken retroorbitally under short term anaesthesia using an alternating sampling scheme at 3, 8, 16, 24, 32, 48, 72 and 96 h p.a., and i.v. additionally at 5 min p.a.

Blood samples were anticoagulated using sodium citrate (1 parts sodium citrate 3.13%+9 parts blood), processed to plasma and stored at −70° C.

rD'D3-FP exposure was determined by measurement of the albumin part of the protein using a human albumin ELISA.

VWF Ko Rats

The test articles were administered i.v. by a single injection into the lateral tail vein at a total volume of 3 mL/kg or s.c. by a single injection one side in the flank at a total volume of 2 mL/kg.

Blood samples from the s.c. group were taken from the saphenous vein at pre-dose, 4, 24, 48, 72, 96 and 168 h p.a. from each animal, and from the i.v. group at pre-dose, 1, 24, 48, 72, 120, 192, 240 and 336 h p.a.

Blood samples were anticoagulated using sodium citrate (1 parts sodium citrate 3.13%+9 parts blood), processed to plasma and stored at −70° C.

rD'D3-FP exposure was determined by measurement of the albumin part of the protein using a human albumin ELISA. Further, FVIII chromogenic activities were measured.

CD Rats

The test articles were administered i.v. by a single injection into the lateral tail vein at a total volume of 3 mL/kg or s.c. by a single injection one side in the flank at a total volume of 3 mL/kg.

Blood samples were taken retroorbitally under short term anaesthesia using an alternating sampling scheme at 3, 8, 24, 48, 72 and 96 h p.a., and i.v. additionally at 5 min p.a.

Blood samples were anticoagulated using sodium citrate (2 parts sodium citrate 3.13%+8 parts blood), processed to plasma and stored at −70° C.

rD'D3-FP exposure was determined by measurement of the albumin part of the protein using a human albumin ELISA.

Pigs

The test articles were administered s.c. in the flanks or i.v. into the ear vein by a single injection, at a total volume ranging from 0.211 to 0.751 mL/kg.

Blood samples were taken from the ear or saphenous vein. Timepoints in the 10 mg/kg rD'D3-FP s.c. groups were pre-dose, 3, 12, 24, 32, 48, 72, 96, 120, 144 and 168 h p.a., and in the i.v. group pre-dose 5 min, 3, 12, 24, 32, 48, 72, 96, 120, 144 and 168 h p.a. Timepoints in the 3 mg/kg rD'D3-FP s.c. groups were pre-dose, 1, 3, 12, 24, 48, 72, 96, 120, 144, 168, 192, 216, 240 and 264 h p.a.

The PK profile was taken from individual animals. Blood samples were anticoagulated using sodium citrate (1 parts sodium citrate 3.13%+9 parts blood), processed to plasma and stored at −70° C. for the determination of FVIII antigen and albumin.

rD'D3-FP exposure was determined by measurement of the albumin part of the protein using a human albumin ELISA. Further, FVIII chromogenic activities were measured.

General rD'D3-FP was applied at a dose level of 3, 3.5 or 10 mg/kg based on human albumin values. In mice, in some groups, rVIII-SingleChain was co-administered at a dose of 100 or 200 IU/kg. The PK profile was taken from four cohorts of mice or 2 cohorts of rats per group, respectively, or from individual pigs.

Calculation of the area under the curve (AUC) from 0 to infinity was done with MATLAB R2017a (Natick, Mass., USA).

Results rD'D3-FP was quantified using an ELISA against human albumin, and measurements were performed up to 4 d p.a. in mice and 14 days p.a. in rats and pigs. All measured data were well above the detection limit over the whole observation period (FIG. 7A).

Figures 1, 7A:
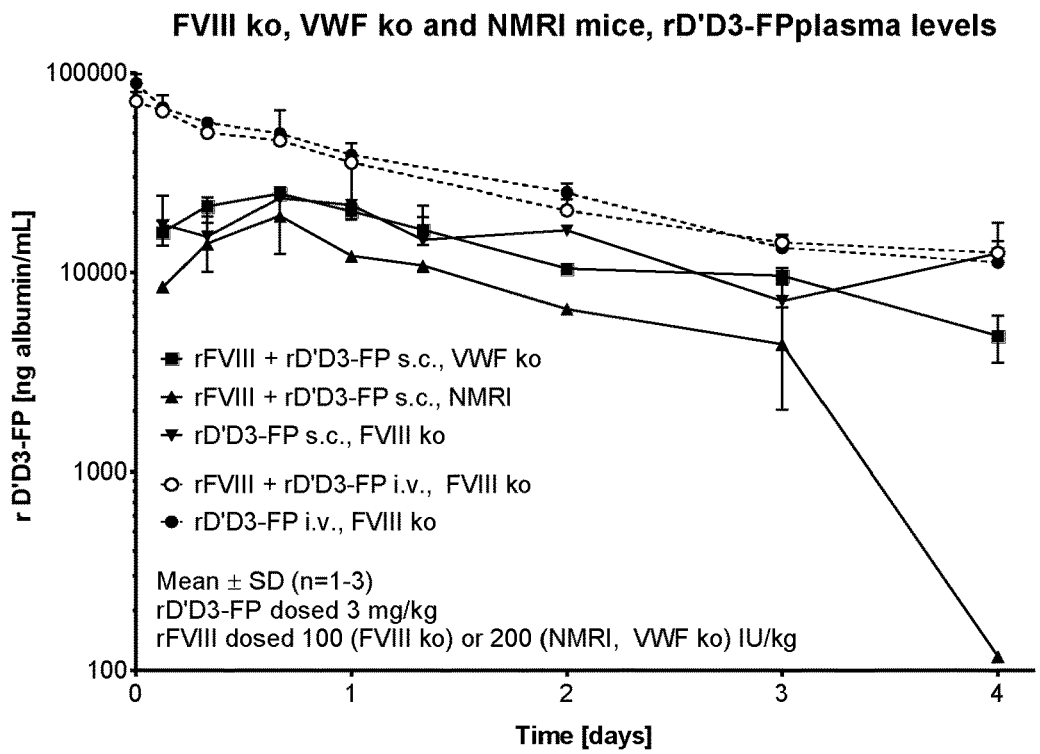
FIG. 7A-1 shows rD'D3-FP exposure quantified in FVIII knockout (ko), VWF ko, and NMRI mice via its albumin component after i.v. or s.c. administration of rD'D3-FP, as described in Example 1.7 , and data is given as mean±SD for n=1-3 mice per timepoint.

FIG. 7A-1 shows PK profiles of rD'D3-FP in different mouse strains, with no visual impact of rFVIII co-administration. Curves in all three strains were about comparable, nevertheless in NMRI mice, exposure declined quicker than in FVIII ko or VWF ko animals.

$AUC_{0-inf}$ and the resulting bioavailabilities of rD'D3-FP are summarized in Table 3. It was shown in FVIII ko mice that i.v. administration of rD'D3-FP with or without rVIII-SingleChain did no impact on the $AUC_{0-inf}$ of rD'D3-FP (with FVIII set to 100%->without FVIII calculates to 89%). Thus, there was no relevant effect of rVIII-SingleChain on the rD'D3-FP PK profile in this experiment. Comparison of $AUC_{0-inf}$ in the different strains suggests no major difference between the three strains, with a ranking from FVIII ko (1590 h*μg/mL) over VWF ko animals (1197 h*μg/mL) to agina slightly lower $AUC_{0-inf}$ in NMRI animals (940 h*μg/mL).

Figures 2, 7A:
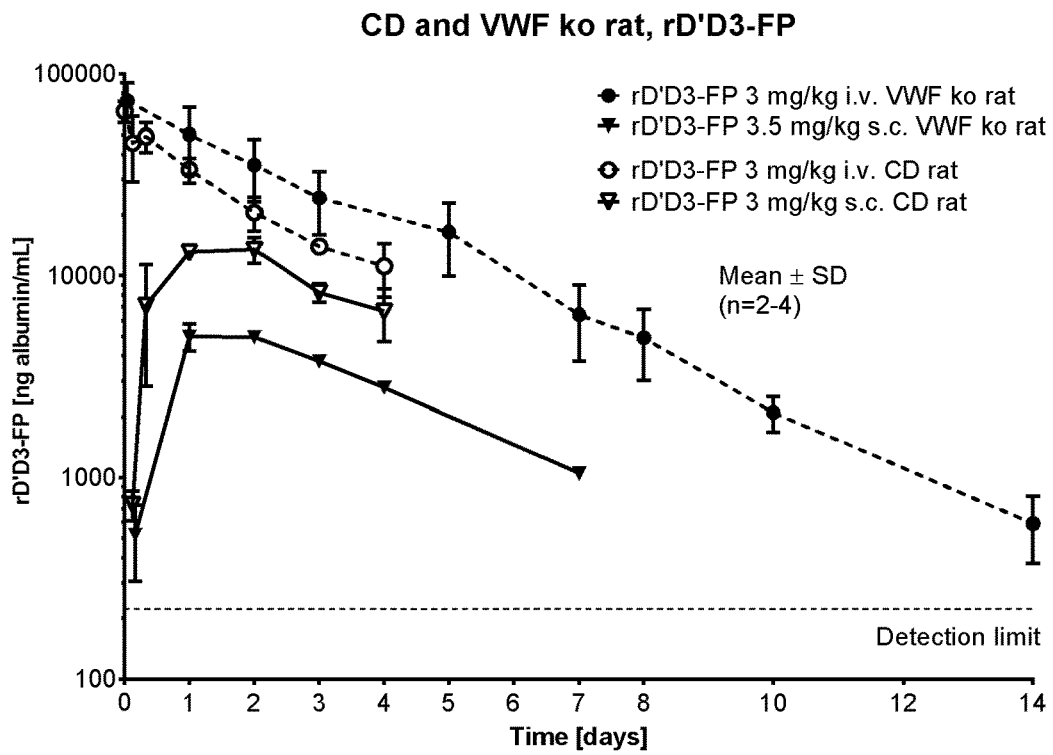
Figures 3, 7A:
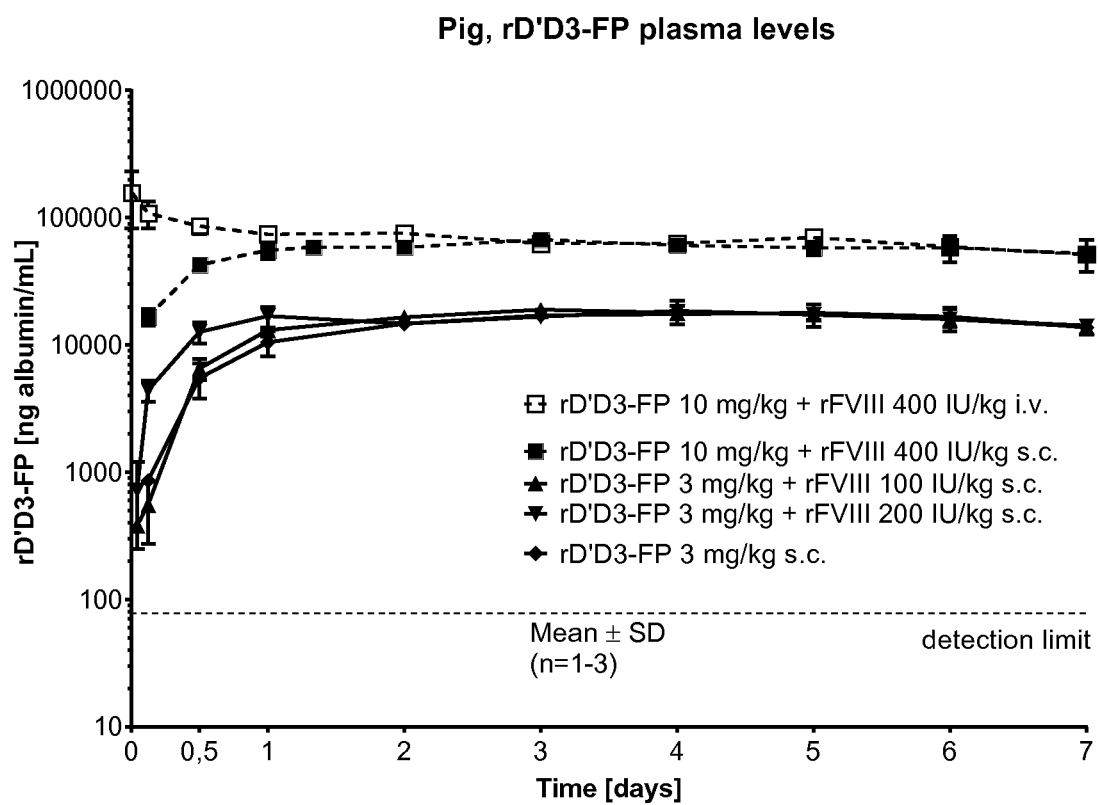

PK profiles in rats are shown in FIG. 7A-2, suggesting comparable clearance of rD'D3-FP after s.c. and i.v administration in CD and VWF ko rats. Nevertheless, s.c. availability was lowest in VWF ko rats as compared to CD rats. FIG. 7A-3 shows PK profiles in pigs, suggesting comparable exposure at same doses after at the latest 2 days, and no impact from rVIII-SingleChain on the PK profile of rD'D3-FP.

Table 4 summarizes the bioavailabilities of rD'D3-FP over species. In rats, evaluation of $AUC_{0\text{-}inf}$ (CD rats) and $AUC_{0\text{-}inf}$ (VWF ko rats) for calculation of bioavailability showed values of 40% and 11%, respectively, i.e. a better bioavailability was seen in FVIII-competent rats as compared to VWF ko animals. This is in contrast to the observations in mice $AUC_{0\text{-}inf}$ inf evaluation, suggesting about comparable data from VWF ko and NMRI animals. If at all, VWF ko mice would have better $AUC_{0\text{-}inf}$ as compared to NMRI mice. In pigs, $AUC_{0\text{-}inf}$ of rD'D3-FP ranged between 59 to 187%. Taken together, compared over species, the pig showed the highest rD'D3-FP bioavailability.

TABLE 3

$AUC_{0\text{-}inf}$ of rD'D3-FP quantified as albumin in different mice strains

| | $AUC_{0\text{-}inf}$ [h * μg/mL] | Bioavailability [%] |
|---|---|---|
| NMRI | | |
| 200 IU/kg rFVIII + 3 mg/kg rD'D3-FP s.c. | 940 | n.d. |
| FVIII ko | | |
| 3 mg/kg rD'D3-FP s.c. | 1590 | 48 |
| 100 IU/kg rFVIII + 3 mg/kg rD'D3-FP i.v. | 3702 | |
| 3 mg/kg rD'D3-FP i.v. | 3286 | |
| VWF ko | | |
| 200 IU/kg rFVIII + 3 mg/kg rD'D3-FP s.c. | 1197 | n.d. | n.d. not determined

TABLE 4

Bioavailabilities of rD'D3-FP quantified as albumin in different species

| | Mice | Rat | Pig |
|---|---|---|---|
| FVIII competent | n.d. | 40% | 59-187% |
| FVIII ko | 48% | n.d. | n.d. |
| VWF ko | n.d. | 11% | n.d. | n.d. not determined

Figures 1, 7B:
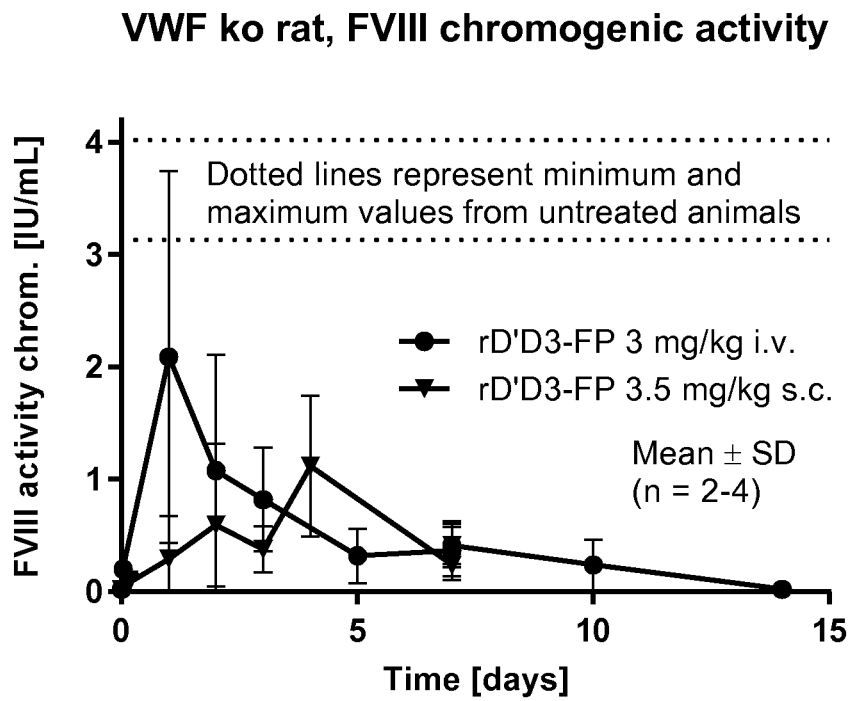
Figures 2, 7B:
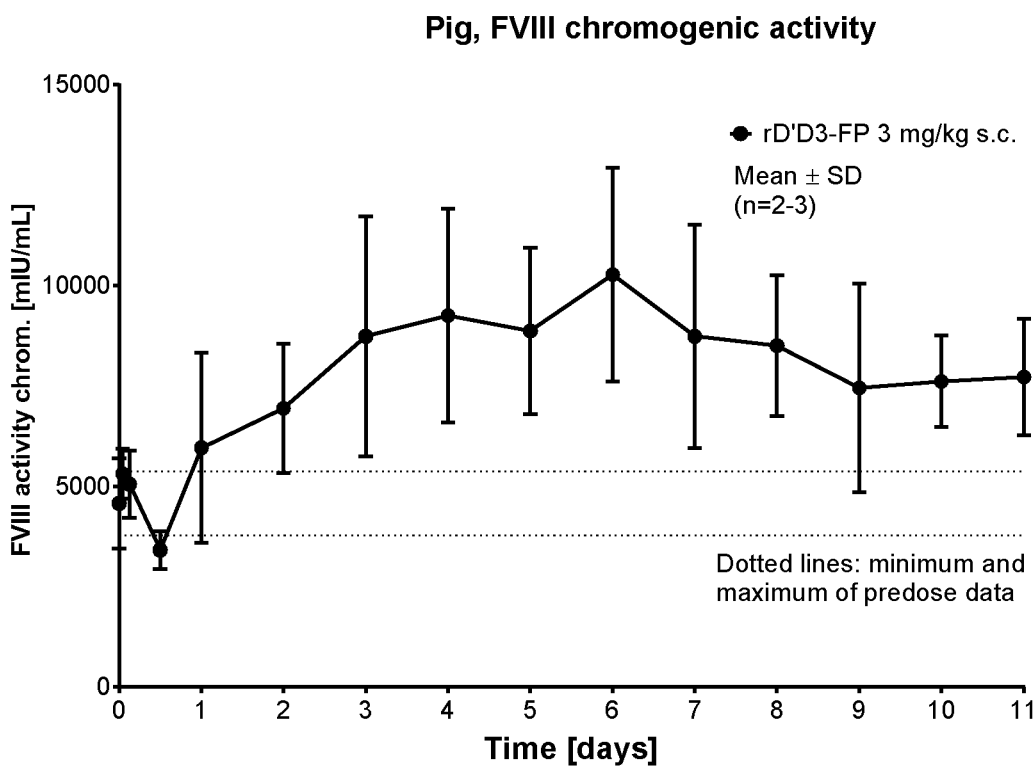

Endogenous FVIII chromogenic activity increased not only after intravenous (see before, examples 1.1-1.5) but also after subcutaneous rD'D-FP administration (FIG. 7B). FIG. 7B-1 shows that in rats, values increased with a maximum at day 1 (3 mg/kg i.v.) or day 4 (10 mg/kg s.c.). This calculates for a reduction in effect on FVIII $AUC_{0\text{-}inf}$ after s.c. as compared to i.v. rD'D3-FP administration (independent of the rD'D3-FP dose) to 17% (chromogenic) and 14% (clotting) activity. This slight but nevertheless relevant increase in endogenous FVIII activity was observed for i.v. as well as s.c. treatment (mainly ranging from ~0.5-1 IU/mL or 50-100%), and thus ranging slightly below the levels reached in CD rats (compare FIG. 4B).

In pigs (FIG. 7B-2), an increase in FVIII chromogenic activity was observed at about 1 day after s.c. administration of rD'D3-FP. This effect lasted over the whole period of 11 days. This increase was maximally 2-fold above predose values (maximal increase by ~5 IU/mL or 500% to ~10 IU/mL=1000%—in line with higher baseline values in these animals as compared to men, i.e. in line with the small effects after i.v. compound administration to FVIII competent animals.

Thus, these data suggest that treatment with rD'D3-FP can be done not only using i.v. but also using s.c. compound administration.

Example 1.8: Impact of Multiple Intravenous Doses of rD'D3-FP on Endogenous FVIII Levels in VWF Ko Rats Animals Male and female VWF ko rats in a weight range of 281-504 g were breed at Charles River Laboratories (Sulzfeld, Germany). The group size was n=11, divided in 4 cohorts. Thus, n=2-3 animals per time-point were used.

In house, the animals were kept at standard housing conditions, i.e. at 20-24° C. under a 12 h/12 h light-darkness cycle. Animals were fed ad libitum with standard mouse and rat diet (Ssniff-Versuchsdiäten, Soest, Germany). Tap water was supplied ad libitum. Animal husbandry and study procedures complied with the German Animal Welfare law and European Union regulations.

Experimental Details

The test articles were administered i.v. by multiple injections into the lateral tail vein at a total volume of 3 mL/kg on day 0 (cohort 1), day 0+7 (cohort 2), 0+7+14+21 (cohort 3) or day 0+7+14 (cohort 4). Two blood samples per animal were taken retroorbitally under short term anaesthesia at the cohort-specific timepoints (cohort 1: predose+7 days p.a., cohort 2: 3+10 days p.a., cohort 3: 17+24 days p.a., cohort 4: 14+21 days p.a.).

rD'D3-FP was applied at a dose level of 3 mg/kg based on human albumin values. The PK profile was taken from four cohorts of VWF ko rats. Blood samples were anticoagulated using sodium citrate (2 parts sodium citrate 3.13%+8 parts blood), processed to plasma and stored at −70° C. for the determination of albumin.

rD'D3-FP exposure was determined by measurement of the albumin part of the construct using a human albumin ELISA. Further, FVIII chromogenic and clotting activity and aPTT using Pathromtin® SL was measured.

Figure 8A:
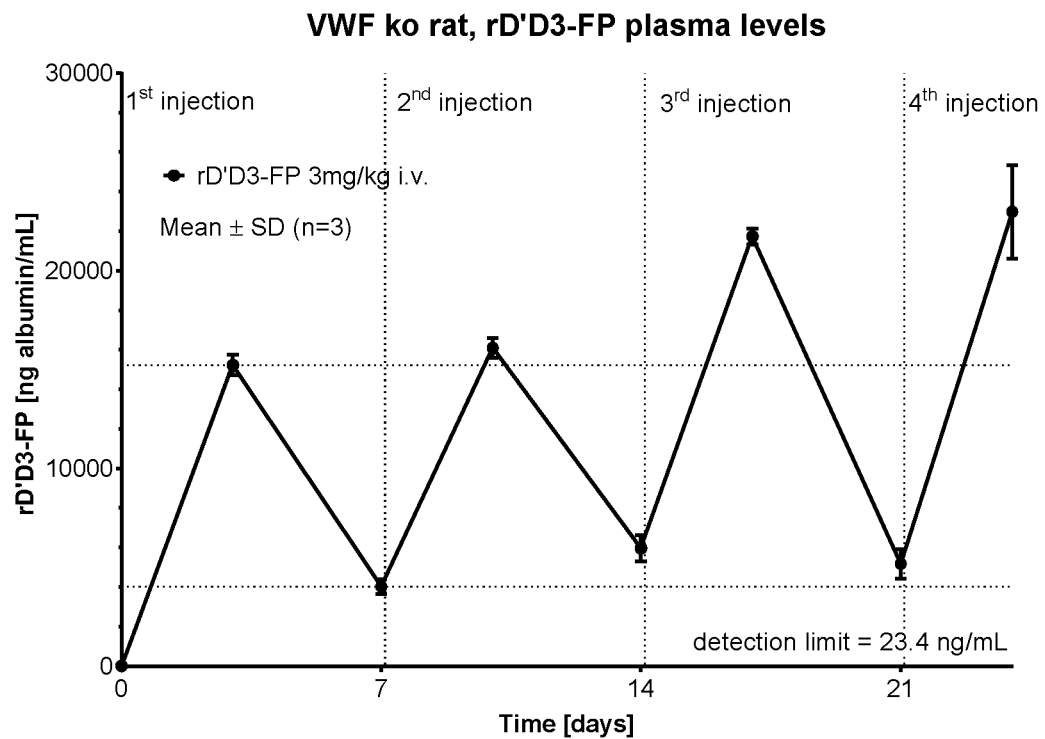
FIG. 8A shows rD'D3-FP exposure quantified in VWF ko rats via its albumin component after i.v. or s.c. administration of rD'D3-FP, as described in Example 1.8, and data is given as mean±SD for n=3 rats per timepoint. The dashed line represents the detection limit for rD'D3-FP.

Results rD'D3-FP was quantified using an ELISA against human albumin, and measurements were performed up to day 24 d. All measured data were well above the detection limit over the whole observation period (FIG. 8A). With the 4 administrations, a slight accumulation was observed in peak (to 151%) as well as trough (to 128%) levels.

Figure 8B:
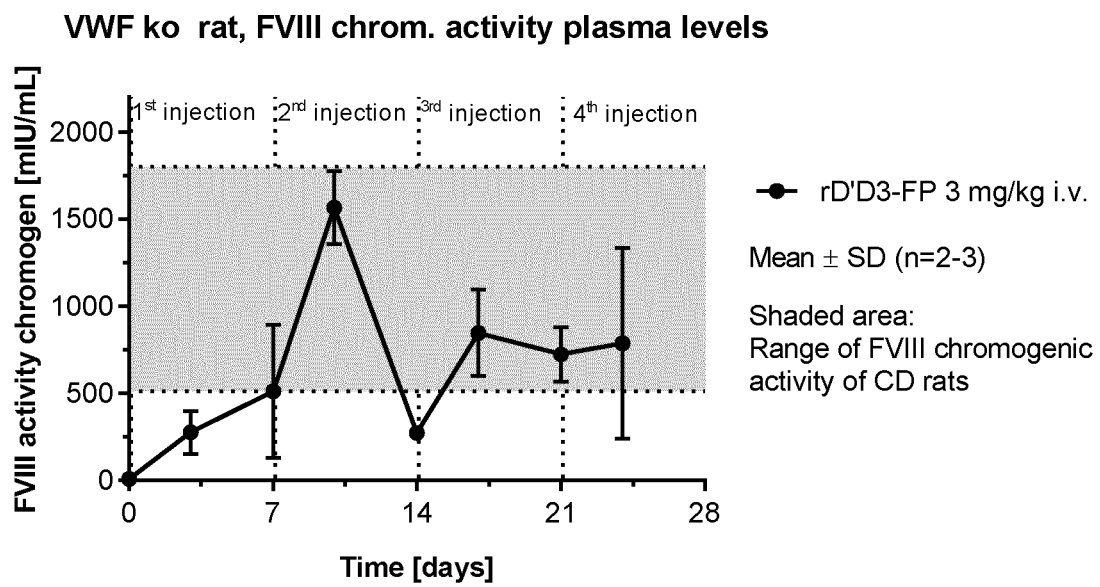
FIG. 8B shows FVIII activity quantified as chromogenic FVIII activity in VWF ko rats after i.v. or s.c. administration of rD'D3-FP, as described in Example 1.8, and data is given as mean±SD for n=2-3 rats per timepoint. The grey shade with dotted lines represent the minimum and maximum of data from untreated healthy CD rats.
Figure 8C:
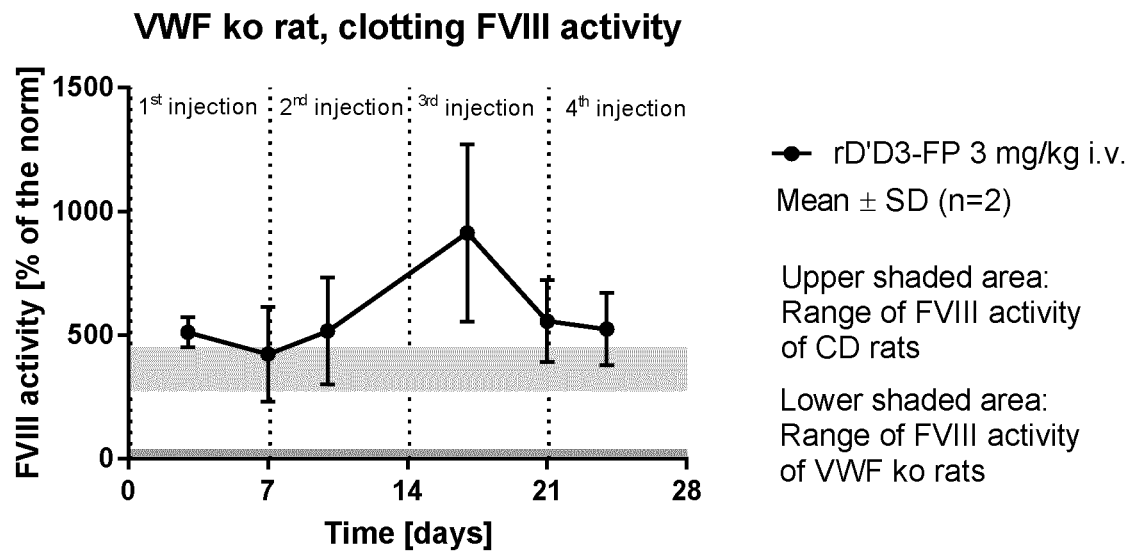
FIG. 8C shows FVIII activity quantified as clotting FVIII activity in VWF ko rats after i.v. or s.c. administration of rD'D3-FP, as described in Example 1.8, and data is given as mean±SD for n=2 rats per timepoint. The grey shade represents the minimum to maximum range of data from untreated healthy CD rats.

FVIII chromogenic (FIG. 8B) activity levels were increased from values below to the detection limit after the $2^{nd}$ administration into the range observed in CD rats (maximal increase to ~1.8 IU/mL=180%). FVIII clotting activity (FIG. 8C) was even slightly above the data measured in CD rats (maximal increase to ~800%—in line with higher baseline values in these animals as compared to men). Nevertheless, no accumulation was seen for the two FVIII activity assays over a period of 4 weeks.

Figure 8D:
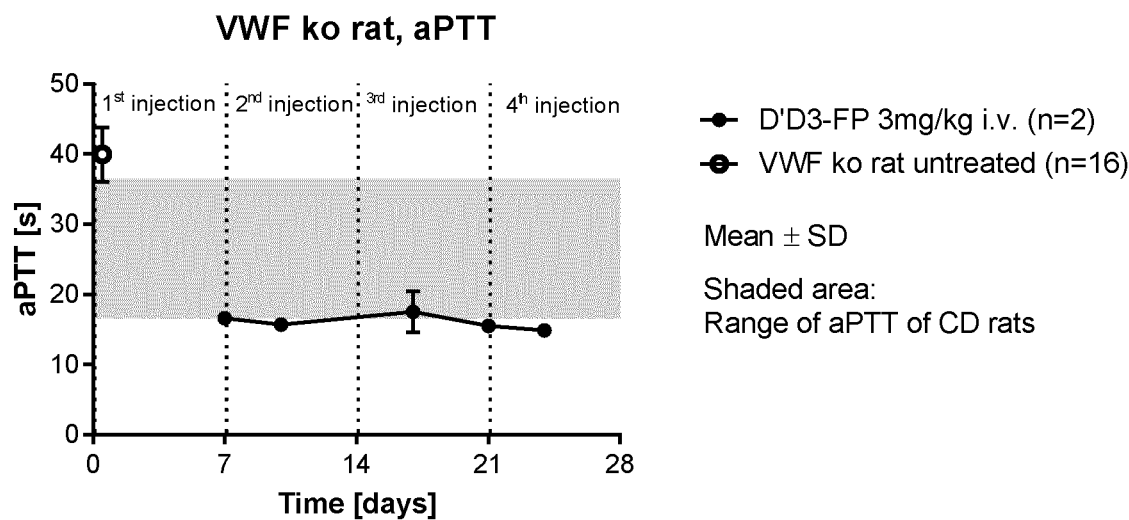
FIG. 8D shows activated partial thrombin time (aPTT) using Pathromtin® SL in VWF ko rats after i.v. or s.c. administration of rD'D3-FP, as described in Example 1.8, and data is given as mean±SD for n=2 rats per timepoint. The grey shade represents the minimum and maximum of predose data of the VWF ko rats. The shaded area represents the minimum and maximum of predose data from healthy CD rats.

In line with this, aPTT decreased from above normal values from CD rats to values at the lower range of the normal range of CD rats (FIG. 8D).

Taken together, these data suggest that multiple treatments with rD'D3-FP can be done with slight accumulation of rD'D3-FP, but without accumulation of FVIII levels and with normalization of aPTT.

Example 1.9: Investigation of rD'D3-FP Given Subcutaneously and rVIII-SingleChain Given Intravenously in a Hemophilia a Model, i.e. in FVIII Ko Rat Animals Male and female FVIII ko rats in a weight range of 220-487 g were breed at Charles River Laboratories (Sulzfeld, Germany). The group size was n=6, divided in 2 cohorts. Thus, n=3 animals per time-point were used.

In house, the animals were kept at standard housing conditions, i.e. at 20-24° C. under a 12 h/12 h light-darkness cycle. Animals were fed ad libitum with standard mouse and rat diet (Ssniff-Versuchsdiäten, Soest, Germany). Tap water was supplied ad libitum. Animal husbandry and study procedures complied with the German Animal Welfare law and European Union regulations.

Experimental Details

The test articles were administered s.c. in the neck (rD'D3-FP) or i.v. (rVIII-SingleChain) into the lateral tail vein of FVIII ko rats by a single injection, at a total volume of 3 mL/kg. rD'D3-FP was applied s.c. in a dose of 3 mg/kg based on human albumin values 10 minutes prior to rVIII-SingleChain. Animals were treated intravenously with rVIII-SingleChain at a dose of 200 IU/kg chromogenic FVIII activity. rVIII-SingleChain was reconstituted with water for injection, and rD'D3-FP was thawed in a water bath. In every case, a dose volume of 3 mL/kg was administered, with dilution buffer for FVIII (rVIII-SingleChain) or isotonic saline (rD'D3-FP) being used for dissolution of the compounds as necessary.

Blood samples were taken by cannulation of the tail vein. Timepoints in the groups were 0.083, 1, 4, 8, 16, 24, 32, 48 and 72 h p.a. The PK profile was taken from two cohorts of rats per group, and n=3 per timepoint. Blood samples were anticoagulated using sodium citrate (2 parts sodium citrate 3.13%+8 parts blood), processed to plasma and stored at −70° C. for the determination of FVIII activity and FVIII antigen.

rD'D3-FP exposure was determined by measurement of the albumin part of the construct using a human albumin ELISA. Further, FVIII chromogenic activity and human FVIII antigen was measured.

Estimation of the maximal concentration ($C_{max}$), the area under the concentration over time curve from t=0 to t=∞ ($AUC_{0-inf}$), mean residence time (MRT), clearance (CL) and terminal half-life ($t_{1/2}$) was done by two-compartmental modelling in the i.v. calculations, and by two-compartmental-resorption modelling in the s.c. calculations. For parameter estimation, a weighted least-squares cost function was applied. Bioavailability was calculated as the percentage of the $AUC_{0-inf}$ after s.c. administration as compared to i.v. administration. Time to 1, 5 and 10% trough levels was calculated by setting the model equation equal to 0.01, 0.05 or 0.1 IU/mL and solving for time.

Results

Figure 9A:
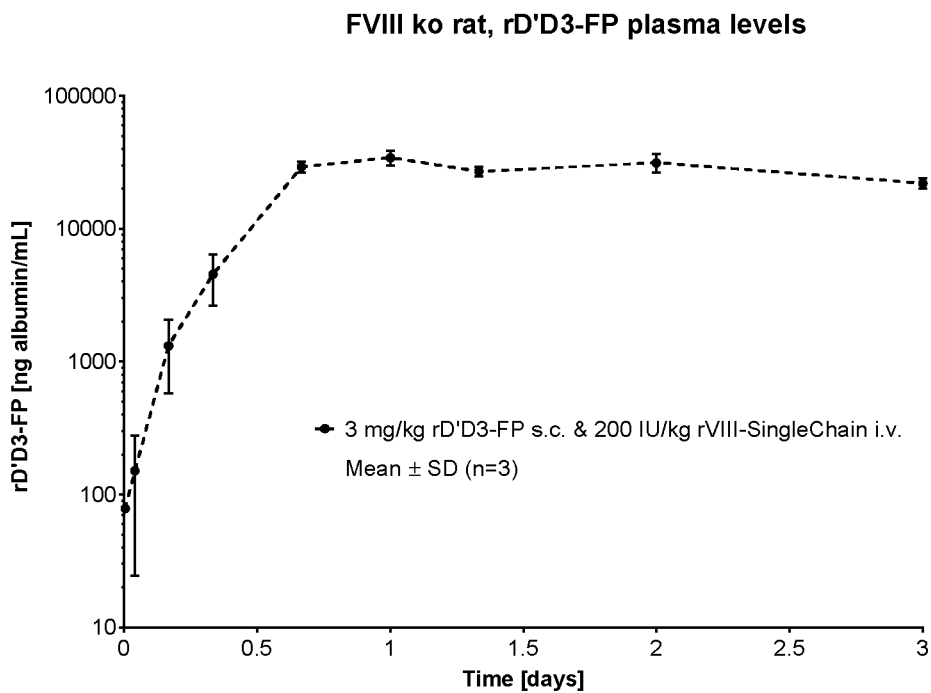
FIG. 9A shows rD'D3-FP exposure quantified in FVIII knockout (ko) rats via its albumin component in CD rats after s.c. administration of rD'D3-FP combined with i.v. administration of rVIII as described in Example 1.9, and data is given as mean±SD for n=3 FVIII ko mice per timepoint. The detection limit represent the minimum and maximum of predose data from healthy CD rats.

Evaluation of D'D3 Data rD'D3-FP was absorbed after s.c. administration. rD'D3-FP could be quantified over the whole period of observation of 72 h; i.e. it remained above the detection limit of 27 ng/mL (FIG. 9A).

$C_{max}$, $AUC_{0-inf}$, clearance, MRT and $t_{1/2}$ are given in Table 5 and confirm relevant exposure of rD'D3-FP over time after subcutaneous administration.

TABLE 5

Pharmacokinetic parameters of rD'D3-FP after s.c. administration of rD'D3-FP followed by i.v. administration of rVIII-SingleChain in FVIII ko rats

| Treatment | $C_{max}$, extrap. [µg/mL] | Clearance [mL/kg/h] | MRT [h] | Half-life, terminal [h] | $AUC_{0-inf}$ [µg * h/mL] |
|---|---|---|---|---|---|
| 3 mg/kg rD'D3-FP s.c. & 200 IU/kg rVIII-SingleChain i.v. | 32 | 1.0 | 77 | 36 | 2959 |

Evaluation of FVIII Data

Figure 9B:
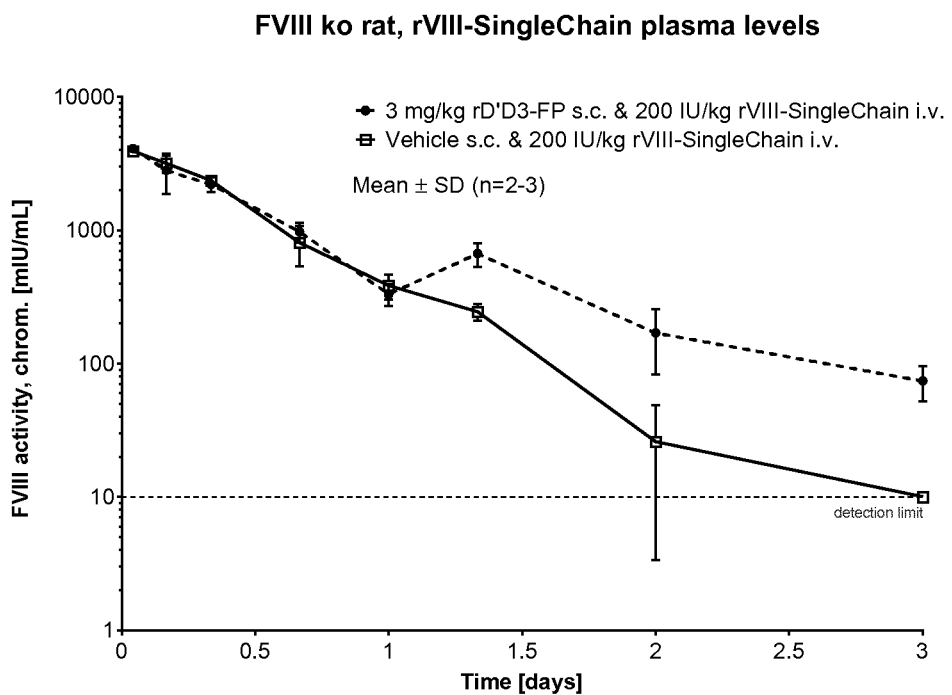
FIG. 9B shows FVIII activity quantified as chromogenic FVIII activity in FVIII ko rats after s.c. administration of rD'D3-FP combined with i.v. administration of rVIII as described in Example 1.9, and data is given as mean±SD for n=2-3 FVIII ko mice per timepoint. The detection limit represents the minimum and maximum of predose data from healthy CD rats.
Figure 9C:
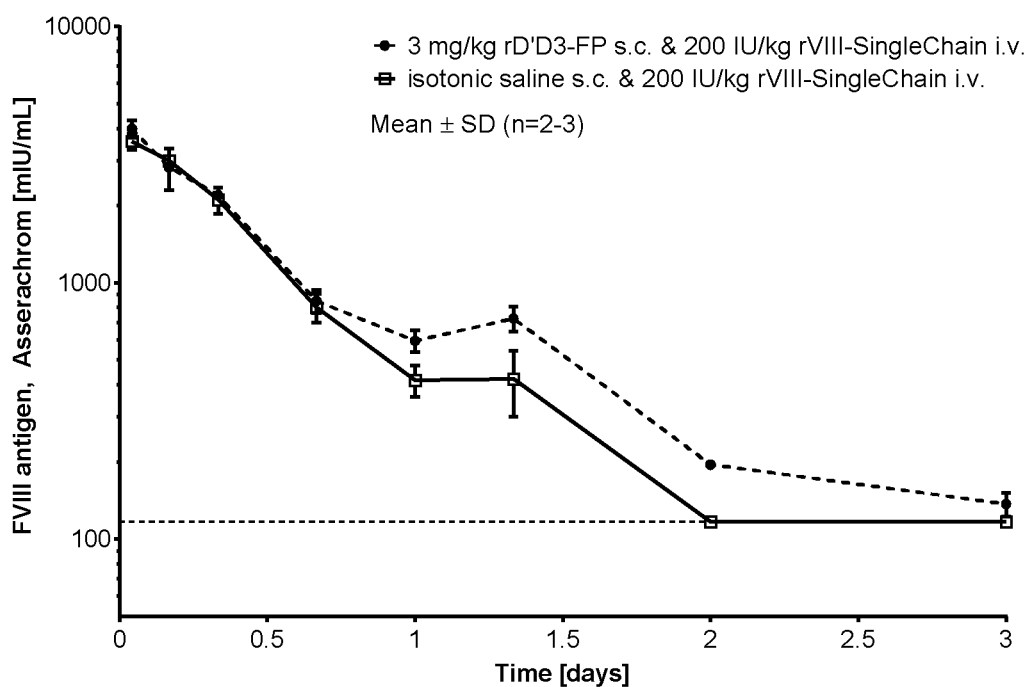
FIG. 9C shows FVIII activity quantified as chromogenic FVIII activity in FVIII ko rats after s.c. administration of rD'D3-FP combined with i.v. administration of rVIII as described in Example 1.9, and data is given as mean±SD for n=2-3 FVIII ko mice per timepoint. The detection limit (dotted line) represents the minimum and maximum of predose data from healthy CD rats.

The FVIII PK profile of rVIII-SingleChain after subcutaneous preadministration of rD'D3-FP was prolonged as compared to rVIII-SingleChain given alone for FVIII chromogenic activity (FIG. 9B) as well as FVIII antigen (FIG. 9C).

FVIII chromogenic activity (FIG. 9B) was well above the detection limit until the last timepoint of 72 h p.a. when rD'D3-FP was preadministered, while it reached the baseline at 72 h when FVIII was given alone. Visually, exposure was improved with subcutaneous preadministration of rD'D3-FP starting at 32 h p.a.

Similar observations were done for FVIII:Ag (FIG. 9C), but exposure was already improved with subcutaneous preadministration of rD'D3-FP starting at 24 h p.a., and baseline was reached already at 48 h p.a. with FVIII given alone, probably related to lower variability of the measured concentrations.

Predosing of rD'D3-FP improved clearance, MRT and $t_{1/2}$ for both FVIII chromogenic activity and FVIII.Ag.

$AUC_{0-inf}$ improved by 41% for FVIII chromogenic activity (Table 6) and by 49% for FVIII:Ag (Table 8). $C_{max}$ improved by 30% for FVIII chromogenic activity and 23% for FVIII:Ag (Table 6 and 8, respectively).

Time to trough was calculated for both administration schemes with and without rD'D3-FP for chromogenic activity (Table 7) and for FVIII:Ag (Table 9). As for $AUC_{0-inf}$, predosing of rD'D3-FP showed also favourable trough levels for chromogenic activity as well as FVIII antigen. Prolongation was 6% and 18% for 1% trough, 9% and 19% for 5% trough and 8% and 18% for 10% trough for chromogenic FVIII activity and FVIII:Ag, respectively.

TABLE 6

Pharmacokinetic parameters of FVIII chromogenic activity after administration of rD'D3-FP s.c. followed by i.v. administration of rVIII-SingleChain in FVIII ko rats

| Treatment | $C_{max}$, extrap. [mIU/mL] | Clearance [mL/kg/h] | MRT [h] | Half-life, terminal [h] | $AUC_{0-inf}$ [mIU * h/mL] |
|---|---|---|---|---|---|
| 3 mg/kg rD'D3-FP s.c. & 200 IU/kg rVIII-SingleChain i.v. | 4036 | 4.2 | 12 | 8 | 47435 |
| 200 IU/kg rVIII-SingleChain i.v. | 3107 | 6.0 | 11 | 7 | 33428 |

TABLE 7

Time to trough levels of rVIII-SingleChain (FVIII chromogenic activity) after s.c. administration in FVIII ko rats

| Treatment | Time to 1% trough [h] | Time to 5% trough [h] | Time to 10% trough [h] |
|---|---|---|---|
| 3 mg/kg rD'D3-FP s.c. & 200 IU/kg rVIII-SingleChain i.v. | 53 | 35 | 27 |
| 200 IU/kg rVIII-SingleChain i.v. | 50 | 32 | 25 |

TABLE 8

Pharmacokinetic parameters of FVIII antigen after administration of rD'D3-FP s.c. followed by i.v. administration of rVIII-SingleChain in FVIII ko rats

| Treatment | $C_{max}$, extrap. [mIU/mL] | Clearance [mL/kg/h] | MRT [h] | Half-life, terminal [h] | $AUC_{0-inf}$ [mIU * h/mL] |
|---|---|---|---|---|---|
| 3 mg/kg rD'D3-FP s.c. & 200 IU/kg rVIII-SingleChain i.v. | 3662 | 3.8 | 14 | 10 | 53957 |
| 200 IU/kg rVIII-SingleChain i.v. | 2983 | 5.8 | 12 | 8 | 36211 |

TABLE 9

Time to trough levels of rVIII-SingleChain (FVIII antigen) after s.c. administration in FVIII ko rats

| Treatment | Time to 1% trough [h] | Time to 5% trough [h] | Time to 10% trough [h] |
|---|---|---|---|
| 3 mg/kg rD'D3-FP s.c. & 200 IU/kg rVIII-SingleChain i.v. | 66 | 43 | 33 |
| 200 IU/kg rVIII-SingleChain i.v. | 56 | 36 | 28 |

Conclusion from In Vivo Animal Experiments

These studies demonstrate that i.v. or s.c. administration of rD'D3-FP slightly increases endogenous levels of FVIII in healthy rats, rabbits, pigs and monkeys, even with the already physiological FVIII levels in these animals. Predose values were hardly exceeded, thereby only slight or no shortening of aPTT was observed.

In animals that show a haemophilia A bleeding type (VWF ko rats or VWF ko mice, that have relevantly reduced FVIII activity levels), this increase of endogenous FVIII activity is stronger than in the healthy animals, with increases of absolute FVIII levels to levels about equal or above those of healthy mice and rats. In these animals, physiological levels were either restored (levels within the upper end of the physiological variability, for example up to 200-300% of the norm chromogenic FVIII activity after administration of 1 and 3 mg/kg rD'D3-FP in VWF ko rats—in line with higher baseline values in these animals as compared to men) or exceeded the physiological range (for example ≥400% of the norm chromogenic FVIII activity after administration of 10 mg/kg rD'D3-FP in VWF ko rats). In the VWF ko mouse as an example with lower baseline values regarding chromogenic FVIII activity as compared to men, ~40% of the norm were reached at a dose of 10 mg/kg rD'D3-FP, i.e. an increase <2-fold above levels observed in healthy NMRI mice. This suggests that in individuals with initially reduced FVIII levels, i.e. a haemophilia A phenotype, a FVIII elevating effect may potentially be stronger than in healthy subjects.

Similar effects were achieved by co-administration of rD'D3-FP EYA or EY variant, or by rD'D3-CTP.

Multiple doses of rD'D3-FP in VWF ko rats led to a slight accumulation of rD'D3-FP over time, while FVIII activity reached (chromogenic activity) or slightly exceeded (clotting activity) physiological levels, and aPTT was restored to normal values.

Without wishing to be bound by theory, this may be explained by a physiological down-regulation of FVIII synthesis in healthy animals with physiological FVIII levels as compared to the VWF ko rats and mice. It may thus be speculated that the effect on FVIII in human haemophilia A patients should be comparable to that observed in VWF ko rats and mice, and thus should achieve long lasting physiological levels. These effects have been shown after i.v. and s.c. administration. Further bioavailabilites of rD'D3-FP ranged between 11-187%, dependent on species and genotype, with highest values achieved in pigs, known to be a well predictive model for s.c. bioavailability. Thereby, these data are suggesting that s.c. treatment is feasible as well.

Example 2: Determination of FVIII Affinity to VWF Fragment Dimer and Monomer

A VWF fragment (1-1242) albumin fusion (D'D3-FP) was expressed in a bioreactor; after purification as described above and isolation of monomer and dimer, the affinity of FVIII to these preparations was assessed through surface plasmon resonance via a Biacore instrument (T200, GE Healthcare).

An anti-albumin antibody (MA1-20124, Thermo Scientific) was covalently coupled via its N-terminus to an activated CM 3 chip by NHS (N-Hydroxysuccinimide) and EDC (Ethanolamine hydrochloride), both contained in the amine coupling kit (BR1000-50) from GE Healthcare. For immobilization 3 μg/mL of the antibody were diluted in sodium acetate buffer (10 mM, pH 5.0) and the antibody solution was flown over the chip for 7 min. at a flow rate of 10 μL/min. After the immobilization procedure non-coupled dextran filaments were saturated by flowing ethanolamine solution (1 M, pH 8.3) over the chip for 5 min (at a flow rate of 10 μL/min). The aim of saturating the flow cell was to minimize unspecific binding of the analytes to the chip. A reference flow cell was set up by saturating an empty flow cell with ethanolamine by using the same procedure as above.

Dimeric and monomeric D'D3-FP proteins, respectively, were immobilized to the covalently coupled anti-albumin antibody by a flow of the D'D3-FP proteins (5 μg/mL) over the chip for 3 min (flow rate of 10 μL/min).

To create binding curves for FVIII, each D'D3-FP protein preparation was diluted in running buffer (HBS-P+: 0.1 M HEPES, 1.5 M NaCl and 0.5% v/v Surfactant P20, pH 7.4; product code BR100671, GE Healthcare) to concentrations of 0.25 nM, 0.5 nM, 1 nM, 3 nM and 4 nM. By performing a single cycle kinetic, samples with ascending concentrations of each dilution were flown over the chip for 2 min (flow rate 30 μL/min.), followed by a dissociation time of 10 min. with running buffer HBS-P+. All measurements were performed twice. The temperature for the measuring procedure was adjusted to +25° C.

Binding parameters were calculated using BiaEvaluation Software. The curve fitting methods were based on Langmuir equations. The input data for calculations were the molar mass of the analyte FVIII (rVIII-SingleChain) of 170 kDa, other parameters like max. RU and slopes were automatically extracted out of the fitted association and dissociation curves. The outputs of BiaEvaluation Software are the association rate constants and the dissociation rate constants, from which the affinity constants were calculated. The results are shown in Table 10.

TABLE 10

FVIII affinity data for D'D3-FP dimer and monomer

| D'D3-FP preparation | ka [1/Ms] | kd [1/s] | KD [M] |
|---|---|---|---|
| D'D3-FP Dimer | $4.5 \times 10^7$ | $1.5 \times 10^{-3}$ | $3.4 \times 10^{-11}$ |
| D'D3-FP Monomer | $9.9 \times 10^5$ | $3.0 \times 10^{-2}$ | $3.0 \times 10^{-8}$ |

The dimeric D'D3-FP shows a significantly ($K_D$=34 μM) increased affinity to FVIII compared to the D'D3-FP monomer ($K_D$=30 nM) which results both from a faster association and a slower dissociation of rVIII-SingleChain.

The invention claimed is:

1. A method of treating a blood coagulation disorder, comprising administering an effective amount of a polypeptide comprising a truncated von Willebrand Factor (VWF) and a half-life extending moiety to a human subject having a blood coagulation disorder and having endogenous Factor VIII (FVIII), wherein the blood coagulation disorder is von-Willebrand disease, wherein the truncated VWF comprises an amino acid sequence having a sequence identity of at least 90% to 764 to 1242 of SEQ ID NO:4, wherein the activity level of endogenous FVIII in said human subject before treatment with said polypeptide is reduced relative to the activity level of FVIII in normal human plasma (NHP) provided that the activity level of endogenous FVIII in said human subject is from 0.5% to 40% of the activity level of endogenous FVIII in normal human plasma (NHP), wherein the polypeptide is capable of binding to endogenous FVIII, and wherein the endogenous FVIII level is increased following administration of said polypeptide, wherein said polypeptide is administered for prophylactic treatment of said human subject, wherein said treatment does not comprise co-administration of exogenous FVIII, and wherein the polypeptide is administered to the human subject in a molar ratio of the polypeptide to endogenous VWF in the human subject of at least 50.

2. The method of claim 1, wherein, following administration of the polypeptide, the activity level of endogenous FVIII is increased to at least 1% of the activity level of endogenous FVIII in NHP.

3. The method of claim 1, wherein the truncated von Willebrand Factor (VWF) is a human truncated von Willebrand Factor (VWF).

4. The method of claim 1, wherein the activity level of endogenous FVIII in said human subject before treatment with said polypeptide is from 0.5% to 30% of the activity level of endogenous FVIII in NHP.

5. The method of claim 1, wherein the activity level of endogenous FVIII in said human subject before treatment with said polypeptide is at least 1% of the activity level of endogenous FVIII in NHP.

6. The method of claim 1, wherein the polypeptide is administered intravenously or extravascularly.

7. The method of claim 1, wherein the polypeptide is a dimer.

8. The method of claim 7, wherein the affinity of said dimer to FVIII is greater than the affinity of a monomeric polypeptide to said FVIII, wherein said monomeric polypeptide has the same amino acid sequence as a monomeric subunit of the dimer, and wherein the polypeptide binds to FVIII with a dissociation constant $K_D$ ranging from 0.1 pm to less than 1 nM.

9. The method of claim 1, wherein the truncated VWF consists of (a) amino acids 764 to 1242 of SEQ ID NO:4, or (b) an amino acid sequence having a sequence identity of at least 90% to amino acids 764 to 1242 of SEQ ID NO:4.

10. The method of claim 1, wherein the half-life extending moiety is a heterologous amino acid sequence that is fused to the truncated VWF.

11. The method of claim 10, wherein said heterologous amino acid sequence is chosen from albumin or fragments thereof, transferrin or fragments thereof, the C-terminal peptide of human chorionic gonadotropin, an XTEN sequence, homo-amino acid repeats (HAP), proline-alanine-serine repeats (PAS), afamin, alpha-fetoprotein, Vitamin D binding protein, polypeptides capable of binding under physiological conditions to albumin or to immunoglobulin constant regions, and polypeptides capable of binding to the neonatal Fc receptor (FcRn).

12. The method of claim 1, wherein the half-life extending moiety is conjugated to the truncated VWF of the polypeptide.

13. The method of claim 12, wherein said half-life extending moiety is chosen from hydroxyethyl starch (HES), polyethylene glycol (PEG), polysialic acids (PSAs), elastin-like polypeptides, heparosan polymers, hyaluronic acid and albumin binding ligands, and combinations thereof.

14. The method of claim 1, wherein the pharmacokinetic parameters of the endogenous FVIII are improved by the administration of the polypeptide, and wherein the mean residence time (MRT) of the endogenous FVIII is increased, the half-life of the endogenous FVIII is prolonged, and/or the clearance of the endogenous FVIII is reduced.

15. The method of claim 1, wherein the plasma half-life of the polypeptide is higher than the plasma half-life of endogenous VWF and/or the plasma half-life of VWF of normal human plasma (NHP).

16. The method of claim 15, wherein the plasma half-life of the polypeptide is at least 25% higher than the plasma half-life of endogenous VWF and/or the plasma half-life of VWF of normal human plasma (NHP).

17. The method of claim 1, wherein following administration of the polypeptide, the human subject's endogenous FVIII activity level is increased up to the physiological FVIII level (100%=1 IU/mL) or not substantially increased above the physiological FVIII level in normal human plasma.

18. The method of claim 11, wherein polypeptides capable of binding to the neonatal Fc receptor (FcRn) comprise immunoglobulin constant regions and portions thereof.

19. The method of claim 18, wherein the immunoglobulin constant regions and portions thereof comprise the Fc portion of immunoglobulin, and combinations thereof.

20. The method of claim 4, wherein the activity level of endogenous FVIII in said human subject before treatment with said polypeptide is less than 20% of the activity level of endogenous FVIII in NHP.

21. The method of claim 5, wherein the activity level of endogenous FVIII in said human subject before treatment with said polypeptide is at least 2% of the activity level of endogenous FVIII in NHP.

22. The method of claim 8, wherein the polypeptide binds to FVIII with a dissociation constant $K_D$ ranging from 0.1 pm to less than 500 pM.

23. The method of claim 8, wherein the polypeptide binds to FVIII with a dissociation constant $K_D$ ranging from 0.1 pm to less than 200 pM.

24. The method of claim 8, wherein the polypeptide binds to FVIII with a dissociation constant $K_D$ ranging from 0.1 pm to less than 100 pM.

* * * * *

SEQUENCE LISTING

```
<160> NUMBER OF SEQ ID NOS: 7

<210> SEQ ID NO 1
<211> LENGTH: 5616
<212> TYPE: DNA
<213> ORGANISM: Artificial Sequence
<220> FEATURE:
<223> OTHER INFORMATION: DNA encoding construct VWF fragment - G/S
      Linker - albumin
<220> FEATURE:
<221> NAME/KEY: misc_feature
<222> LOCATION: (1)..(6)
<223> OTHER INFORMATION: EcoRI restriction enzyme cleavage site
<220> FEATURE:
<221> NAME/KEY: misc_feature
<222> LOCATION: (32)..(3757)
<223> OTHER INFORMATION: coding sequence for VWF amino acids 1 to 1242
<220> FEATURE:
<221> NAME/KEY: misc_feature
<222> LOCATION: (3758)..(3850)
<223> OTHER INFORMATION: coding sequence for glycine/serine linker
<220> FEATURE:
<221> NAME/KEY: misc_feature
<222> LOCATION: (3851)..(5608)
<223> OTHER INFORMATION: coding sequence for human albumin
<220> FEATURE:
<221> NAME/KEY: misc_feature
<222> LOCATION: (5609)..(5616)
<223> OTHER INFORMATION: NotI restriction enzyme cleavage site

<400> SEQUENCE: 1
gaattcccgc agccctcatt tgcaggggaa gatgattcct gccagatttg ccggggtgct      60
gcttgctctg gccctcattt tgccagggac cctttgtgca gaaggaactc gcggcaggtc     120
atccacggcc cgatgcagcc ttttcggaag tgacttcgtc aacacctttg atgggagcat     180
gtacagcttt gcgggatact gcagttacct cctggcaggg ggctgccaga aacgctcctt     240
ctcgattatt ggggacttcc agaatggcaa gagagtgagc ctctccgtgt atcttgggga     300
attttttgac atccatttgt ttgtcaatgg taccgtgaca caggggacc aaagagtctc     360
```

-continued

| | |
|---|---|
| catgccctat gcctccaaag ggctgtatct agaaactgag gctgggtact acaagctgtc | 420 |
| cggtgaggcc tatggctttg tggccaggat cgatggcagc ggcaactttc aagtcctgct | 480 |
| gtcagacaga tacttcaaca agacctgcgg gctgtgtggc aactttaaca tctttgctga | 540 |
| agatgacttt atgacccaag aagggacctt gacctcggac ccttatgact ttgccaactc | 600 |
| atgggctctg agcagtggag aacagtggtg tgaacgggca tctcctccca gcagctcatg | 660 |
| caacatctcc tctggggaaa tgcagaaggg cctgtgggag cagtgccagc ttctgaagag | 720 |
| cacctcggtg tttgcccgct gccaccctct ggtggacccc gagccttttg tggccctgtg | 780 |
| tgagaagact ttgtgtgagt gtgctggggg gctggagtgc gcctgccctg ccctcctgga | 840 |
| gtacgcccgg acctgtgccc aggagggaat ggtgctgtac ggctggaccg accacagcgc | 900 |
| gtgcagccca gtgtgccctg ctggtatgga gtataggcag tgtgtgtccc cttgcgccag | 960 |
| gacctgccag agcctgcaca tcaatgaaat gtgtcaggag cgatgcgtgg atggctgcag | 1020 |
| ctgccctgag ggacagctcc tggatgaagg cctctgcgtg gagagcaccg agtgtccctg | 1080 |
| cgtgcattcc ggaaagcgct accctccccgg caccccctc tctcgagact gcaacacctg | 1140 |
| catttgccga aacagccagt ggatctgcag caatgaagaa tgtccagggg agtgccttgt | 1200 |
| cacaggtcaa tcacacttca agagctttga caacagatac ttcaccttca gtgggatctg | 1260 |
| ccagtacctg ctggcccggg attgccagga ccactccttc tccattgtca ttgagactgt | 1320 |
| ccagtgtgct gatgaccgcg acgctgtgtg cacccgctcc gtcaccgtcc ggctgcctgg | 1380 |
| cctgcacaac agccttgtga aactgaagca tggggcagga gttgccatgg atggccagga | 1440 |
| cgtccagctc ccctcctga aaggtgacct ccgcatccag catacagtga cggcctccgt | 1500 |
| gcgcctcagc tacggggagg acctgcagat ggactgggat ggccgcggga ggctgctggt | 1560 |
| gaagctgtcc cccgtctatg ccgggaagac ctgcggcctg tgtgggaatt acaatggcaa | 1620 |
| ccagggcgac gacttccttta cccccctctgg gctggcggag cccgggtgg aggacttcgg | 1680 |
| gaacgcctgg aagctgcacg gggactgcca ggacctgcag aagcagcaca gcgatccctg | 1740 |
| cgccctcaac ccgcgcatga ccaggttctc cgaggaggcg tgcgcggtcc tgacgtcccc | 1800 |
| cacattcgag gcctgccatc gtgccgtcag cccgctgccc tacctgcgga actgccgcta | 1860 |
| cgacgtgtgc tcctgctcgg acggccgcga gtgcctgtgc ggcgccctgg ccagctatgc | 1920 |
| cgcggcctgc gcggggagag gcgtgcgcgt cgcgtggcgc gagccaggcc gctgtgagct | 1980 |
| gaactgcccg aaaggccagg tgtacctgca gtgcgggacc ccctgcaacc tgacctgccg | 2040 |
| ctctctctct tacccggatg aggaatgcaa tgaggcctgc ctggagggct gcttctgccc | 2100 |
| cccagggctc tacatggatg agagggggga ctgcgtgccc aaggcccagt gccctgttac | 2160 |
| ctatgacggt gagatcttcc agccagaaga catcttctca gaccatcaca ccatgtgcta | 2220 |
| ctgtgaggat ggcttcatgc actgtaccat gagtggagtc cccggaagct gctgcctga | 2280 |
| cgctgtcctc agcagtcccc tgtctcatcg cagcaaaagg agcctatcct gtcggccccc | 2340 |
| catggtcaag ctggtgtgtc cgctgacaa cctgcgggct gaagggctcg agtgtaccaa | 2400 |
| aacgtgccag aactatgacc tggagtgcat gagcatgggc tgtgtctctg gctgcctctg | 2460 |
| ccccccgggc atggtccggc atgagaacag atgtgtggcc ctggaaaggt gtccctgctt | 2520 |
| ccatcagggc aaggagtatg cccctggaga acagtgaag attggctgca acacttgtgt | 2580 |
| ctgtcgggac cggaagtgga actgcacaga ccatgtgtgt gatgccacgt gctccacgat | 2640 |
| cggcatggcc cactacctca ccttcgacgg gctcaaatac ctgttccccg gggagtgcca | 2700 |

```
gtacgttctg gtgcaggatt actgcggcag taaccctggg acctttcgga tcctagtggg   2760
gaataaggga tgcagccacc cctcagtgaa atgcaagaaa cgggtcacca tcctggtgga   2820
gggaggagag attgagctgt ttgacgggga ggtgaatgtg aagaggccca tgaaggatga   2880
gactcacttt gaggtggtgg agtctggccg gtacatcatt ctgctgctgg gcaaagccct   2940
ctccgtggtc tgggaccgcc acctgagcat ctccgtggtc ctgaagcaga cataccagga   3000
gaaagtgtgt ggcctgtgtg ggaattttga tggcatccag aacaatgacc tcaccagcag   3060
caacctccaa gtggaggaag accctgtgga ctttgggaac tcctggaaag tgagctcgca   3120
gtgtgctgac accagaaaag tgcctctgga ctcatcccct gccacctgcc ataacaacat   3180
catgaagcag acgatggtgg attcctcctg tagaatcctt accagtgacg tcttccagga   3240
ctgcaacaag ctggtggacc ccgagccata tctggatgtc tgcatttacg acacctgctc   3300
ctgtgagtcc attggggact cgcctgctt ctgcgacacc attgctgcct atgcccacgt   3360
gtgtgcccag catggcaagg tggtgacctg gaggacggcc acattgtgcc cccagagctg   3420
cgaggagagg aatctccggg agaacgggta tgagtgtgag tggcgctata acagctgtgc   3480
acctgcctgt caagtcacgt gtcagcaccc tgagccactg gcctgccctg tgcagtgtgt   3540
ggagggctgc catgcccact gccctccagg gaaaatcctg gatgagcttt gcagacctg    3600 cgttgaccct gaagactgtc cagtgtgtga ggtggctggc cggcgttttg cctcaggaaa   3660
gaaagtcacc ttgaatccca gtgaccctga gcactgccag atttgccact gtgatgttgt   3720
caacctcacc tgtgaagcct gccaggagcc gggaggctcg agcgggggat ctggcgggtc   3780
tggaggctct ggagggtcgg gaggctctgg aggctctggg ggatctggcg ggtctggagg   3840
gtcgggatcc gatgcacaca agagtgaggt tgctcatcgg tttaaagatt gggagaaga    3900 aaatttcaaa gccttggtgt tgattgcctt tgctcagtat cttcagcagt gtccatttga   3960
agatcatgta aaattagtga atgaagtaac tgaatttgca aaaacatgtg ttgctgatga   4020
gtcagctgaa aattgtgaca atcacttca tacccttttt ggagacaaat tatgcacagt    4080
tgcaactctt cgtgaaacct atggtgaaat ggctgactgc tgtgcaaaac aagaacctga   4140
gagaaatgaa tgcttcttgc aacacaaaga tgacaaccca aacctccccc gattggtgag   4200
accagaggtt gatgtgatgt gcactgcttt tcatgacaat aagagacat ttttgaaaaa     4260 atacttatat gaaattgcca aagacatcc ttactttat gccccggaac tccttttctt      4320
tgctaaaagg tataagctg cttttacaga atgttgccaa gctgctgata agctgcctg      4380 cctgttgcca aagctcgatg aacttcggga tgaagggaag gcttcgtctg ccaaacagag    4440
actcaagtgt gccagtctcc aaaaatttgg agaaagagct ttcaaagcat gggcagtagc   4500
tcgcctgagc cagagatttc ccaaagctga gtttgcagaa gtttccaagt tagtgacaga   4560
tcttaccaaa gtccacacgg aatgctgcca tggagatctg cttgaatgtg ctgatgacag   4620
ggcggacctt gccaagtata tctgtgaaaa tcaagattcg atctccagta aactgaagga   4680
atgctgtgaa aaacctctgt ggaaaaaatc ccactgcatt gccgaagtgg aaaatgatga   4740
gatgcctgct gacttgcctt cattagctgc tgattttgtt gaaagtaagg atgtttgcaa   4800
aaactatgct gaggcaaagg atgtcttcct gggcatgttt ttgtatgaat atgcaagaag   4860
gcatcctgat tactctgtcg tgctgctgct gagacttgcc aagacatatg aaaccactct   4920
agagaagtgc tgtgccgctg cagatcctca tgaatgctat gccaaagtgt tcgatgaatt   4980
taaacctctt gtgaagagc ctcagaattt aatcaaacaa aattgtgagc ttttttgagca    5040 gcttggagag tacaaattcc agaatgcgct attagttcgt tacaccaaga aagtacccca   5100
```

```
agtgtcaact ccaactcttg tagaggtctc aagaaaccta ggaaaagtgg gcagcaaatg    5160
ttgtaaacat cctgaagcaa aaagaatgcc ctgtgcagaa gactatctat ccgtggtcct    5220
gaaccagtta tgtgtgttgc atgagaaaac gccagtaagt gacagagtca ccaaatgctg    5280
cacagaatcc ttggtgaaca ggcgaccatg cttttcagct ctggaagtcg atgaaacata    5340
cgttcccaaa gagtttaatg ctgaaacatt caccttccat gcagatatat gcacactttc    5400
tgagaaggag agacaaatca agaaacaaac tgcacttgtt gagctcgtga acacaagcc    5460 caaggcaaca aaagagcaac tgaaagctgt tatggatgat ttcgcagctt ttgtagagaa    5520
gtgctgcaag gctgacgata aggagacctg ctttgccgag gagggtaaaa aacttgttgc    5580
tgcaagtcaa gctgccttag cttataggc ggccgc                              5616
```

<210> SEQ ID NO 2
<211> LENGTH: 1095
<212> TYPE: PRT
<213> ORGANISM: Artificial Sequence
<220> FEATURE:
<223> OTHER INFORMATION: polypeptide encoded by SEQ ID NO:1
<220> FEATURE:
<221> NAME/KEY: MISC_FEATURE
<222> LOCATION: (1)..(479)
<223> OTHER INFORMATION: VWF D?D3 region (VWF amino acids 764 - 1242)
<220> FEATURE:
<221> NAME/KEY: MISC_FEATURE
<222> LOCATION: (480)..(510)
<223> OTHER INFORMATION: glycine/serine linker
<220> FEATURE:
<221> NAME/KEY: MISC_FEATURE
<222> LOCATION: (511)..(1095)
<223> OTHER INFORMATION: human albumin

<400> SEQUENCE: 2

```
Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205
```

```
Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
            245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
            340                 345                 350

Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
            420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Ser
465                 470                 475                 480

Ser Gly Gly Ser Gly Gly Ser Gly Gly Ser Gly Gly Ser Gly Gly Ser
                485                 490                 495

Gly Gly Ser Gly Gly Ser Gly Gly Ser Gly Gly Ser Gly Ser Asp Ala
            500                 505                 510

His Lys Ser Glu Val Ala His Arg Phe Lys Asp Leu Gly Glu Glu Asn
        515                 520                 525

Phe Lys Ala Leu Val Leu Ile Ala Phe Ala Gln Tyr Leu Gln Gln Cys
    530                 535                 540

Pro Phe Glu Asp His Val Lys Leu Val Asn Glu Val Thr Glu Phe Ala
545                 550                 555                 560

Lys Thr Cys Val Ala Asp Glu Ser Ala Glu Asn Cys Asp Lys Ser Leu
                565                 570                 575

His Thr Leu Phe Gly Asp Lys Leu Cys Thr Val Ala Thr Leu Arg Glu
            580                 585                 590

Thr Tyr Gly Glu Met Ala Asp Cys Cys Ala Lys Gln Glu Pro Glu Arg
        595                 600                 605

Asn Glu Cys Phe Leu Gln His Lys Asp Asp Asn Pro Asn Leu Pro Arg
    610                 615                 620
```

-continued

Leu Val Arg Pro Glu Val Asp Val Met Cys Thr Ala Phe His Asp Asn
625                 630                 635                 640

Glu Glu Thr Phe Leu Lys Lys Tyr Leu Tyr Glu Ile Ala Arg Arg His
        645                 650                 655

Pro Tyr Phe Tyr Ala Pro Glu Leu Leu Phe Phe Ala Lys Arg Tyr Lys
            660                 665                 670

Ala Ala Phe Thr Glu Cys Cys Gln Ala Ala Asp Lys Ala Ala Cys Leu
                675                 680                 685

Leu Pro Lys Leu Asp Glu Leu Arg Asp Glu Gly Lys Ala Ser Ser Ala
690                 695                 700

Lys Gln Arg Leu Lys Cys Ala Ser Leu Gln Lys Phe Gly Glu Arg Ala
705                 710                 715                 720

Phe Lys Ala Trp Ala Val Ala Arg Leu Ser Gln Arg Phe Pro Lys Ala
            725                 730                 735

Glu Phe Ala Glu Val Ser Lys Leu Val Thr Asp Leu Thr Lys Val His
                740                 745                 750

Thr Glu Cys Cys His Gly Asp Leu Leu Glu Cys Ala Asp Asp Arg Ala
                755                 760                 765

Asp Leu Ala Lys Tyr Ile Cys Glu Asn Gln Asp Ser Ile Ser Ser Lys
770                 775                 780

Leu Lys Glu Cys Cys Glu Lys Pro Leu Leu Glu Lys Ser His Cys Ile
785                 790                 795                 800

Ala Glu Val Glu Asn Asp Glu Met Pro Ala Asp Leu Pro Ser Leu Ala
            805                 810                 815

Ala Asp Phe Val Glu Ser Lys Asp Val Cys Lys Asn Tyr Ala Glu Ala
                820                 825                 830

Lys Asp Val Phe Leu Gly Met Phe Leu Tyr Glu Tyr Ala Arg Arg His
                835                 840                 845

Pro Asp Tyr Ser Val Val Leu Leu Leu Arg Leu Ala Lys Thr Tyr Glu
850                 855                 860

Thr Thr Leu Glu Lys Cys Cys Ala Ala Ala Asp Pro His Glu Cys Tyr
865                 870                 875                 880

Ala Lys Val Phe Asp Glu Phe Lys Pro Leu Val Glu Glu Pro Gln Asn
            885                 890                 895

Leu Ile Lys Gln Asn Cys Glu Leu Phe Glu Gln Leu Gly Glu Tyr Lys
                900                 905                 910

Phe Gln Asn Ala Leu Leu Val Arg Tyr Thr Lys Lys Val Pro Gln Val
                915                 920                 925

Ser Thr Pro Thr Leu Val Glu Val Ser Arg Asn Leu Gly Lys Val Gly
930                 935                 940

Ser Lys Cys Cys Lys His Pro Glu Ala Lys Arg Met Pro Cys Ala Glu
945                 950                 955                 960

Asp Tyr Leu Ser Val Val Leu Asn Gln Leu Cys Val Leu His Glu Lys
            965                 970                 975

Thr Pro Val Ser Asp Arg Val Thr Lys Cys Cys Thr Glu Ser Leu Val
                980                 985                 990

Asn Arg Arg Pro Cys Phe Ser Ala Leu Glu Val Asp Glu Thr Tyr Val
                995                 1000                1005

Pro Lys Glu Phe Asn Ala Glu Thr Phe Thr Phe His Ala Asp Ile
    1010                1015                1020

Cys Thr Leu Ser Glu Lys Glu Arg Gln Ile Lys Lys Gln Thr Ala
    1025                1030                1035

Leu Val Glu Leu Val Lys His Lys Pro Lys Ala Thr Lys Glu Gln

```
              1040                1045                1050
Leu Lys Ala Val Met Asp Asp Phe Ala Ala Phe Val Glu Lys Cys
         1055                1060                1065

Cys Lys Ala Asp Asp Lys Glu Thr Cys Phe Ala Glu Glu Gly Lys
         1070                1075                1080

Lys Leu Val Ala Ala Ser Gln Ala Ala Leu Gly Leu
         1085                1090              1095

<210> SEQ ID NO 3
<211> LENGTH: 8442
<212> TYPE: DNA
<213> ORGANISM: Homo sapiens
<220> FEATURE:
<221> NAME/KEY: CDS
<222> LOCATION: (1)..(8442)

<400> SEQUENCE: 3
```

| | | | | | | | | | | | | | | | | |
|---|---|---|---|---|---|---|---|---|---|---|---|---|---|---|---|---|
| atg | att | cct | gcc | aga | ttt | gcc | ggg | gtg | ctg | ctt | gct | ctg | gcc | ctc | att | 48 |
| Met | Ile | Pro | Ala | Arg | Phe | Ala | Gly | Val | Leu | Leu | Ala | Leu | Ala | Leu | Ile | |
| 1 | | | | 5 | | | | | 10 | | | | | 15 | | |

```
ttg cca ggg acc ctt tgt gca gaa gga act cgc ggc agg tca tcc acg     96
Leu Pro Gly Thr Leu Cys Ala Glu Gly Thr Arg Gly Arg Ser Ser Thr
             20                  25                  30 gcc cga tgc agc ctt ttc gga agt gac ttc gtc aac acc ttt gat ggg    144
Ala Arg Cys Ser Leu Phe Gly Ser Asp Phe Val Asn Thr Phe Asp Gly
         35                  40                  45 agc atg tac agc ttt gcg gga tac tgc agt tac ctc ctg gca ggg ggc    192
Ser Met Tyr Ser Phe Ala Gly Tyr Cys Ser Tyr Leu Leu Ala Gly Gly
     50                  55                  60 tgc cag aaa cgc tcc ttc tcg att att ggg gac ttc cag aat ggc aag    240
Cys Gln Lys Arg Ser Phe Ser Ile Ile Gly Asp Phe Gln Asn Gly Lys
 65                  70                  75                  80 aga gtg agc ctc tcc gtg tat ctt ggg gaa ttt ttt gac atc cat ttg    288
Arg Val Ser Leu Ser Val Tyr Leu Gly Glu Phe Phe Asp Ile His Leu
                 85                  90                  95 ttt gtc aat ggt acc gtg aca cag ggg gac caa aga gtc tcc atg ccc    336
Phe Val Asn Gly Thr Val Thr Gln Gly Asp Gln Arg Val Ser Met Pro
            100                 105                 110 tat gcc tcc aaa ggg ctg tat cta gaa act gag gct ggg tac tac aag    384
Tyr Ala Ser Lys Gly Leu Tyr Leu Glu Thr Glu Ala Gly Tyr Tyr Lys
        115                 120                 125 ctg tcc ggt gag gcc tat ggc ttt gtg gcc agg atc gat ggc agc ggc    432
Leu Ser Gly Glu Ala Tyr Gly Phe Val Ala Arg Ile Asp Gly Ser Gly
    130                 135                 140 aac ttt caa gtc ctg ctg tca gac aga tac ttc aac aag acc tgc ggg    480
Asn Phe Gln Val Leu Leu Ser Asp Arg Tyr Phe Asn Lys Thr Cys Gly
145                 150                 155                 160 ctg tgt ggc aac ttt aac atc ttt gct gaa gat gac ttt atg acc caa    528
Leu Cys Gly Asn Phe Asn Ile Phe Ala Glu Asp Asp Phe Met Thr Gln
                165                 170                 175 gaa ggg acc ttg acc tcg gac cct tat gac ttt gcc aac tca tgg gct    576
Glu Gly Thr Leu Thr Ser Asp Pro Tyr Asp Phe Ala Asn Ser Trp Ala
            180                 185                 190 ctg agc agt gga gaa cag tgg tgt gaa cgg gca tct cct ccc agc agc    624
Leu Ser Ser Gly Glu Gln Trp Cys Glu Arg Ala Ser Pro Pro Ser Ser
        195                 200                 205 tca tgc aac atc tcc tct ggg gaa atg cag aag ggc ctg tgg gag cag    672
Ser Cys Asn Ile Ser Ser Gly Glu Met Gln Lys Gly Leu Trp Glu Gln
    210                 215                 220 tgc cag ctt ctg aag agc acc tcg gtg ttt gcc cgc tgc cac cct ctg    720
```

-continued

| | | | | | | | | | | | | | | |
|---|---|---|---|---|---|---|---|---|---|---|---|---|---|---|
| Cys | Gln | Leu | Leu | Lys | Ser | Thr | Ser | Val | Phe | Ala | Arg | Cys | His | Pro | Leu |
| 225 | | | | | 230 | | | | | 235 | | | | | 240 |

```
gtg gac ccc gag cct ttt gtg gcc ctg tgt gag aag act ttg tgt gag     768
Val Asp Pro Glu Pro Phe Val Ala Leu Cys Glu Lys Thr Leu Cys Glu
            245                 250                 255 tgt gct ggg ggg ctg gag tgc gcc tgc cct gcc ctc ctg gag tac gcc     816
Cys Ala Gly Gly Leu Glu Cys Ala Cys Pro Ala Leu Leu Glu Tyr Ala
        260                 265                 270 cgg acc tgt gcc cag gag gga atg gtg ctg tac ggc tgg acc gac cac     864
Arg Thr Cys Ala Gln Glu Gly Met Val Leu Tyr Gly Trp Thr Asp His
            275                 280                 285 agc gcg tgc agc cca gtg tgc cct gct ggt atg gag tat agg cag tgt     912
Ser Ala Cys Ser Pro Val Cys Pro Ala Gly Met Glu Tyr Arg Gln Cys
        290                 295                 300 gtg tcc cct tgc gcc agg acc tgc cag agc ctg cac atc aat gaa atg     960
Val Ser Pro Cys Ala Arg Thr Cys Gln Ser Leu His Ile Asn Glu Met
305                 310                 315                 320 tgt cag gag cga tgc gtg gat ggc tgc agc tgc cct gag gga cag ctc    1008
Cys Gln Glu Arg Cys Val Asp Gly Cys Ser Cys Pro Glu Gly Gln Leu
                325                 330                 335 ctg gat gaa ggc ctc tgc gtg gag agc acc gag tgt ccc tgc gtg cat    1056
Leu Asp Glu Gly Leu Cys Val Glu Ser Thr Glu Cys Pro Cys Val His
            340                 345                 350 tcc gga aag cgc tac cct ccc ggc acc tcc ctc tct cga gac tgc aac    1104
Ser Gly Lys Arg Tyr Pro Pro Gly Thr Ser Leu Ser Arg Asp Cys Asn
        355                 360                 365 acc tgc att tgc cga aac agc cag tgg atc tgc agc aat gaa gaa tgt    1152
Thr Cys Ile Cys Arg Asn Ser Gln Trp Ile Cys Ser Asn Glu Glu Cys
370                 375                 380 cca ggg gag tgc ctt gtc aca ggt caa tca cac ttc aag agc ttt gac    1200
Pro Gly Glu Cys Leu Val Thr Gly Gln Ser His Phe Lys Ser Phe Asp
385                 390                 395                 400 aac aga tac ttc acc ttc agt ggg atc tgc cag tac ctg ctg gcc cgg    1248
Asn Arg Tyr Phe Thr Phe Ser Gly Ile Cys Gln Tyr Leu Leu Ala Arg
                405                 410                 415 gat tgc cag gac cac tcc ttc tcc att gtc att gag act gtc cag tgt    1296
Asp Cys Gln Asp His Ser Phe Ser Ile Val Ile Glu Thr Val Gln Cys
            420                 425                 430 gct gat gac cgc gac gct gtg tgc acc cgc tcc gtc acc gtc cgg ctg    1344
Ala Asp Asp Arg Asp Ala Val Cys Thr Arg Ser Val Thr Val Arg Leu
        435                 440                 445 cct ggc ctg cac aac agc ctt gtg aaa ctg aag cat ggg gca gga gtt    1392
Pro Gly Leu His Asn Ser Leu Val Lys Leu Lys His Gly Ala Gly Val
450                 455                 460 gcc atg gat ggc cag gac gtc cag ctc ccc ctc ctg aaa ggt gac ctc    1440
Ala Met Asp Gly Gln Asp Val Gln Leu Pro Leu Leu Lys Gly Asp Leu
465                 470                 475                 480 cgc atc cag cat aca gtg acg gcc tcc gtg cgc ctc agc tac ggg gag    1488
Arg Ile Gln His Thr Val Thr Ala Ser Val Arg Leu Ser Tyr Gly Glu
                485                 490                 495 gac ctg cag atg gac tgg gat ggc cgc ggg agg ctg ctg gtg aag ctg    1536
Asp Leu Gln Met Asp Trp Asp Gly Arg Gly Arg Leu Leu Val Lys Leu
            500                 505                 510 tcc ccc gtc tat gcc ggg aag acc tgc ggc ctg tgt ggg aat tac aat    1584
Ser Pro Val Tyr Ala Gly Lys Thr Cys Gly Leu Cys Gly Asn Tyr Asn
        515                 520                 525 ggc aac cag ggc gac gac ttc ctt acc ccc tct ggg ctg gcg gag ccc    1632
Gly Asn Gln Gly Asp Asp Phe Leu Thr Pro Ser Gly Leu Ala Glu Pro
530                 535                 540
```

-continued

| | |
|---|---|
| cgg gtg gag gac ttc ggg aac gcc tgg aag ctg cac ggg gac tgc cag<br>Arg Val Glu Asp Phe Gly Asn Ala Trp Lys Leu His Gly Asp Cys Gln<br>545        550        555        560 | 1680 |
| gac ctg cag aag cag cac agc gat ccc tgc gcc ctc aac ccg cgc atg<br>Asp Leu Gln Lys Gln His Ser Asp Pro Cys Ala Leu Asn Pro Arg Met<br>        565        570        575 | 1728 |
| acc agg ttc tcc gag gag gcg tgc gcg gtc ctg acg tcc ccc aca ttc<br>Thr Arg Phe Ser Glu Glu Ala Cys Ala Val Leu Thr Ser Pro Thr Phe<br>580        585        590 | 1776 |
| gag gcc tgc cat cgt gcc gtc agc ccg ctg ccc tac ctg cgg aac tgc<br>Glu Ala Cys His Arg Ala Val Ser Pro Leu Pro Tyr Leu Arg Asn Cys<br>     595        600        605 | 1824 |
| cgc tac gac gtg tgc tcc tgc tcg gac ggc cgc gag tgc ctg tgc ggc<br>Arg Tyr Asp Val Cys Ser Cys Ser Asp Gly Arg Glu Cys Leu Cys Gly<br>610        615        620 | 1872 |
| gcc ctg gcc agc tat gcc gcg gcc tgc gcg ggg aga ggc gtg cgc gtc<br>Ala Leu Ala Ser Tyr Ala Ala Ala Cys Ala Gly Arg Gly Val Arg Val<br>625        630        635        640 | 1920 |
| gcg tgg cgc gag cca ggc cgc tgt gag ctg aac tgc ccg aaa ggc cag<br>Ala Trp Arg Glu Pro Gly Arg Cys Glu Leu Asn Cys Pro Lys Gly Gln<br>        645        650        655 | 1968 |
| gtg tac ctg cag tgc ggg acc ccc tgc aac ctg acc tgc cgc tct ctc<br>Val Tyr Leu Gln Cys Gly Thr Pro Cys Asn Leu Thr Cys Arg Ser Leu<br>     660        665        670 | 2016 |
| tct tac ccg gat gag gaa tgc aat gag gcc tgc ctg gag ggc tgc ttc<br>Ser Tyr Pro Asp Glu Glu Cys Asn Glu Ala Cys Leu Glu Gly Cys Phe<br>675        680        685 | 2064 |
| tgc ccc cca ggg ctc tac atg gat gag agg ggg gac tgc gtg ccc aag<br>Cys Pro Pro Gly Leu Tyr Met Asp Glu Arg Gly Asp Cys Val Pro Lys<br>        690        695        700 | 2112 |
| gcc cag tgc ccc tgt tac tat gac ggt gag atc ttc cag cca gaa gac<br>Ala Gln Cys Pro Cys Tyr Tyr Asp Gly Glu Ile Phe Gln Pro Glu Asp<br>705        710        715        720 | 2160 |
| atc ttc tca gac cat cac acc atg tgc tac tgt gag gat ggc ttc atg<br>Ile Phe Ser Asp His His Thr Met Cys Tyr Cys Glu Asp Gly Phe Met<br>        725        730        735 | 2208 |
| cac tgt acc atg agt gga gtc ccc gga agc ttg ctg cct gac gct gtc<br>His Cys Thr Met Ser Gly Val Pro Gly Ser Leu Leu Pro Asp Ala Val<br>     740        745        750 | 2256 |
| ctc agc agt ccc ctg tct cat cgc agc aaa agg agc cta tcc tgt cgg<br>Leu Ser Ser Pro Leu Ser His Arg Ser Lys Arg Ser Leu Ser Cys Arg<br>755        760        765 | 2304 |
| ccc ccc atg gtc aag ctg gtg tgt ccc gct gac aac ctg cgg gct gaa<br>Pro Pro Met Val Lys Leu Val Cys Pro Ala Asp Asn Leu Arg Ala Glu<br>     770        775        780 | 2352 |
| ggg ctc gag tgt acc aaa acg tgc cag aac tat gac ctg gag tgc atg<br>Gly Leu Glu Cys Thr Lys Thr Cys Gln Asn Tyr Asp Leu Glu Cys Met<br>785        790        795        800 | 2400 |
| agc atg ggc tgt gtc tct ggc tgc ctc tgc ccc ccg ggc atg gtc cgg<br>Ser Met Gly Cys Val Ser Gly Cys Leu Cys Pro Pro Gly Met Val Arg<br>        805        810        815 | 2448 |
| cat gag aac aga tgt gtg gcc ctg gaa agg tgt ccc tgc ttc cat cag<br>His Glu Asn Arg Cys Val Ala Leu Glu Arg Cys Pro Cys Phe His Gln<br>     820        825        830 | 2496 |
| ggc aag gag tat gcc cct gga gaa aca gtg aag att ggc tgc aac act<br>Gly Lys Glu Tyr Ala Pro Gly Glu Thr Val Lys Ile Gly Cys Asn Thr<br>835        840        845 | 2544 |
| tgt gtc tgt cgg gac cgg aag tgg aac tgc aca gac cat gtg tgt gat<br>Cys Val Cys Arg Asp Arg Lys Trp Asn Cys Thr Asp His Val Cys Asp<br>        850        855        860 | 2592 |

|  |  |
|---|---|
| gcc acg tgc tcc acg atc ggc atg gcc cac tac ctc acc ttc gac ggg<br>Ala Thr Cys Ser Thr Ile Gly Met Ala His Tyr Leu Thr Phe Asp Gly<br>865                      870                  875                880 | 2640 |
| ctc aaa tac ctg ttc ccc ggg gag tgc cag tac gtt ctg gtg cag gat<br>Leu Lys Tyr Leu Phe Pro Gly Glu Cys Gln Tyr Val Leu Val Gln Asp<br>                      885                  890                895 | 2688 |
| tac tgc ggc agt aac cct ggg acc ttt cgg atc cta gtg ggg aat aag<br>Tyr Cys Gly Ser Asn Pro Gly Thr Phe Arg Ile Leu Val Gly Asn Lys<br>900                      905                  910 | 2736 |
| gga tgc agc cac ccc tca gtg aaa tgc aag aaa cgg gtc acc atc ctg<br>Gly Cys Ser His Pro Ser Val Lys Cys Lys Lys Arg Val Thr Ile Leu<br>            915                  920                925 | 2784 |
| gtg gag gga gga gag att gag ctg ttt gac ggg gag gtg aat gtg aag<br>Val Glu Gly Gly Glu Ile Glu Leu Phe Asp Gly Glu Val Asn Val Lys<br>930                      935                  940 | 2832 |
| agg ccc atg aag gat gag act cac ttt gag gtg gtg gag tct ggc cgg<br>Arg Pro Met Lys Asp Glu Thr His Phe Glu Val Val Glu Ser Gly Arg<br>945                      950                  955                960 | 2880 |
| tac atc att ctg ctg ctg ggc aaa gcc ctc tcc gtg gtc tgg gac cgc<br>Tyr Ile Ile Leu Leu Leu Gly Lys Ala Leu Ser Val Val Trp Asp Arg<br>                      965                  970                975 | 2928 |
| cac ctg agc atc tcc gtg gtc ctg aag cag aca tac cag gag aaa gtg<br>His Leu Ser Ile Ser Val Val Leu Lys Gln Thr Tyr Gln Glu Lys Val<br>            980                  985                990 | 2976 |
| tgt ggc ctg tgt ggg aat ttt gat ggc atc cag aac aat gac ctc acc<br>Cys Gly Leu Cys Gly Asn Phe Asp Gly Ile Gln Asn Asn Asp Leu Thr<br>995                      1000                1005 | 3024 |
| agc agc aac ctc caa gtg gag gaa gac cct gtg gac ttt ggg aac<br>Ser Ser Asn Leu Gln Val Glu Glu Asp Pro Val Asp Phe Gly Asn<br>1010                  1015                1020 | 3069 |
| tcc tgg aaa gtg agc tcg cag tgt gct gac acc aga aaa gtg cct<br>Ser Trp Lys Val Ser Ser Gln Cys Ala Asp Thr Arg Lys Val Pro<br>1025                  1030                1035 | 3114 |
| ctg gac tca tcc cct gcc acc tgc cat aac aac atc atg aag cag<br>Leu Asp Ser Ser Pro Ala Thr Cys His Asn Asn Ile Met Lys Gln<br>1040                  1045                1050 | 3159 |
| acg atg gtg gat tcc tcc tgt aga atc ctt acc agt gac gtc ttc<br>Thr Met Val Asp Ser Ser Cys Arg Ile Leu Thr Ser Asp Val Phe<br>1055                  1060                1065 | 3204 |
| cag gac tgc aac aag ctg gtg gac ccc gag cca tat ctg gat gtc<br>Gln Asp Cys Asn Lys Leu Val Asp Pro Glu Pro Tyr Leu Asp Val<br>1070                  1075                1080 | 3249 |
| tgc att tac gac acc tgc tcc tgt gag tcc att ggg gac tgc gcc<br>Cys Ile Tyr Asp Thr Cys Ser Cys Glu Ser Ile Gly Asp Cys Ala<br>1085                  1090                1095 | 3294 |
| tgc ttc tgc gac acc att gct gcc tat gcc cac gtg tgt gcc cag<br>Cys Phe Cys Asp Thr Ile Ala Ala Tyr Ala His Val Cys Ala Gln<br>1100                  1105                1110 | 3339 |
| cat ggc aag gtg gtg acc tgg agg acg gcc aca ttg tgc ccc cag<br>His Gly Lys Val Val Thr Trp Arg Thr Ala Thr Leu Cys Pro Gln<br>1115                  1120                1125 | 3384 |
| agc tgc gag gag agg aat ctc cgg gag aac ggg tat gag tgt gag<br>Ser Cys Glu Glu Arg Asn Leu Arg Glu Asn Gly Tyr Glu Cys Glu<br>1130                  1135                1140 | 3429 |
| tgg cgc tat aac agc tgt gca cct gcc tgt caa gtc acg tgt cag<br>Trp Arg Tyr Asn Ser Cys Ala Pro Ala Cys Gln Val Thr Cys Gln<br>1145                  1150                1155 | 3474 |
| cac cct gag cca ctg gcc tgc cct gtg cag tgt gtg gag ggc tgc<br>His Pro Glu Pro Leu Ala Cys Pro Val Gln Cys Val Glu Gly Cys | 3519 |

```
                1160                1165                1170
cat gcc cac tgc cct cca ggg aaa atc ctg gat gag ctt ttg cag        3564
His Ala His Cys Pro Pro Gly Lys Ile Leu Asp Glu Leu Leu Gln
    1175                1180                1185 acc tgc gtt gac cct gaa gac tgt cca gtg tgt gag gtg gct ggc        3609
Thr Cys Val Asp Pro Glu Asp Cys Pro Val Cys Glu Val Ala Gly
    1190                1195                1200 cgg cgt ttt gcc tca gga aag aaa gtc acc ttg aat ccc agt gac        3654
Arg Arg Phe Ala Ser Gly Lys Lys Val Thr Leu Asn Pro Ser Asp
    1205                1210                1215 cct gag cac tgc cag att tgc cac tgt gat gtt gtc aac ctc acc        3699
Pro Glu His Cys Gln Ile Cys His Cys Asp Val Val Asn Leu Thr
    1220                1225                1230 tgt gaa gcc tgc cag gag ccg gga ggc ctg gtg gtg cct ccc aca        3744
Cys Glu Ala Cys Gln Glu Pro Gly Gly Leu Val Val Pro Pro Thr
    1235                1240                1245 gat gcc ccg gtg agc ccc acc act ctg tat gtg gag gac atc tcg        3789
Asp Ala Pro Val Ser Pro Thr Thr Leu Tyr Val Glu Asp Ile Ser
    1250                1255                1260 gaa ccg ccg ttg cac gat ttc tac tgc agc agg cta ctg gac ctg        3834
Glu Pro Pro Leu His Asp Phe Tyr Cys Ser Arg Leu Leu Asp Leu
    1265                1270                1275 gtc ttc ctg ctg gat ggc tcc tcc agg ctg tcc gag gct gag ttt        3879
Val Phe Leu Leu Asp Gly Ser Ser Arg Leu Ser Glu Ala Glu Phe
    1280                1285                1290 gaa gtg ctg aag gcc ttt gtg gtg gac atg atg gag cgg ctg cgc        3924
Glu Val Leu Lys Ala Phe Val Val Asp Met Met Glu Arg Leu Arg
    1295                1300                1305 atc tcc cag aag tgg gtc cgc gtg gcc gtg gtg gag tac cac gac        3969
Ile Ser Gln Lys Trp Val Arg Val Ala Val Val Glu Tyr His Asp
    1310                1315                1320 ggc tcc cac gcc tac atc ggg ctc aag gac cgg aag cga ccg tca        4014
Gly Ser His Ala Tyr Ile Gly Leu Lys Asp Arg Lys Arg Pro Ser
    1325                1330                1335 gag ctg cgg cgc att gcc agc cag gtg aag tat gcg ggc agc cag        4059
Glu Leu Arg Arg Ile Ala Ser Gln Val Lys Tyr Ala Gly Ser Gln
    1340                1345                1350 gtg gcc tcc acc agc gag gtc ttg aaa tac aca ctg ttc caa atc        4104
Val Ala Ser Thr Ser Glu Val Leu Lys Tyr Thr Leu Phe Gln Ile
    1355                1360                1365 ttc agc aag atc gac cgc cct gaa gcc tcc cgc atc gcc ctg ctc        4149
Phe Ser Lys Ile Asp Arg Pro Glu Ala Ser Arg Ile Ala Leu Leu
    1370                1375                1380 ctg atg gcc agc cag gag ccc caa cgg atg tcc cgg aac ttt gtc        4194
Leu Met Ala Ser Gln Glu Pro Gln Arg Met Ser Arg Asn Phe Val
    1385                1390                1395 cgc tac gtc cag ggc ctg aag aag aag aag gtc att gtg atc ccg        4239
Arg Tyr Val Gln Gly Leu Lys Lys Lys Lys Val Ile Val Ile Pro
    1400                1405                1410 gtg ggc att ggg ccc cat gcc aac ctc aag cag atc cgc ctc atc        4284
Val Gly Ile Gly Pro His Ala Asn Leu Lys Gln Ile Arg Leu Ile
    1415                1420                1425 gag aag cag gcc cct gag aac aag gcc ttc gtg ctg agc agt gtg        4329
Glu Lys Gln Ala Pro Glu Asn Lys Ala Phe Val Leu Ser Ser Val
    1430                1435                1440 gat gag ctg gag cag caa agg gac gag atc gtt agc tac ctc tgt        4374
Asp Glu Leu Glu Gln Gln Arg Asp Glu Ile Val Ser Tyr Leu Cys
    1445                1450                1455 gac ctt gcc cct gaa gcc cct cct cct act ctg ccc ccc cac atg        4419
```

-continued

```
                Asp Leu Ala Pro Glu Ala Pro Pro Pro Thr Leu Pro Pro His Met
                    1460            1465                1470
gca caa gtc act gtg ggc ccg ggg ctc ttg ggg gtt tcg acc ctg      4464
Ala Gln Val Thr Val Gly Pro Gly Leu Leu Gly Val Ser Thr Leu
    1475            1480                1485 ggg ccc aag agg aac tcc atg gtt ctg gat gtg gcg ttc gtc ctg      4509
Gly Pro Lys Arg Asn Ser Met Val Leu Asp Val Ala Phe Val Leu
    1490            1495                1500 gaa gga tcg gac aaa att ggt gaa gcc gac ttc aac agg agc aag      4554
Glu Gly Ser Asp Lys Ile Gly Glu Ala Asp Phe Asn Arg Ser Lys
    1505            1510                1515 gag ttc atg gag gag gtg att cag cgg atg gat gtg ggc cag gac      4599
Glu Phe Met Glu Glu Val Ile Gln Arg Met Asp Val Gly Gln Asp
    1520            1525                1530 agc atc cac gtc acg gtg ctg cag tac tcc tac atg gtg acc gtg      4644
Ser Ile His Val Thr Val Leu Gln Tyr Ser Tyr Met Val Thr Val
    1535            1540                1545 gag tac ccc ttc agc gag gca cag tcc aaa ggg gac atc ctg cag      4689
Glu Tyr Pro Phe Ser Glu Ala Gln Ser Lys Gly Asp Ile Leu Gln
    1550            1555                1560 cgg gtg cga gag atc cgc tac cag ggc ggc aac agg acc aac act      4734
Arg Val Arg Glu Ile Arg Tyr Gln Gly Gly Asn Arg Thr Asn Thr
    1565            1570                1575 ggg ctg gcc ctg cgg tac ctc tct gac cac agc ttc ttg gtc agc      4779
Gly Leu Ala Leu Arg Tyr Leu Ser Asp His Ser Phe Leu Val Ser
    1580            1585                1590 cag ggt gac cgg gag cag gcg ccc aac ctg gtc tac atg gtc acc      4824
Gln Gly Asp Arg Glu Gln Ala Pro Asn Leu Val Tyr Met Val Thr
    1595            1600                1605 gga aat cct gcc tct gat gag atc aag agg ctg cct gga gac atc      4869
Gly Asn Pro Ala Ser Asp Glu Ile Lys Arg Leu Pro Gly Asp Ile
    1610            1615                1620 cag gtg gtg ccc att gga gtg ggc cct aat gcc aac gtg cag gag      4914
Gln Val Val Pro Ile Gly Val Gly Pro Asn Ala Asn Val Gln Glu
    1625            1630                1635 ctg gag agg att ggc tgg ccc aat gcc cct atc ctc atc cag gac      4959
Leu Glu Arg Ile Gly Trp Pro Asn Ala Pro Ile Leu Ile Gln Asp
    1640            1645                1650 ttt gag acg ctc ccc cga gag gct cct gac ctg gtg ctg cag agg      5004
Phe Glu Thr Leu Pro Arg Glu Ala Pro Asp Leu Val Leu Gln Arg
    1655            1660                1665 tgc tgc tcc gga gag ggg ctg cag atc ccc acc ctc tcc cct gca      5049
Cys Cys Ser Gly Glu Gly Leu Gln Ile Pro Thr Leu Ser Pro Ala
    1670            1675                1680 cct gac tgc agc cag ccc ctg gac gtg atc ctt ctc ctg gat ggc      5094
Pro Asp Cys Ser Gln Pro Leu Asp Val Ile Leu Leu Leu Asp Gly
    1685            1690                1695 tcc tcc agt ttc cca gct tct tat ttt gat gaa atg aag agt ttc      5139
Ser Ser Ser Phe Pro Ala Ser Tyr Phe Asp Glu Met Lys Ser Phe
    1700            1705                1710 gcc aag gct ttc att tca aaa gcc aat ata ggg cct cgt ctc act      5184
Ala Lys Ala Phe Ile Ser Lys Ala Asn Ile Gly Pro Arg Leu Thr
    1715            1720                1725 cag gtg tca gtg ctg cag tat gga agc atc acc acc att gac gtg      5229
Gln Val Ser Val Leu Gln Tyr Gly Ser Ile Thr Thr Ile Asp Val
    1730            1735                1740 cca tgg aac gtg gtc ccg gag aaa gcc cat ttg ctg agc ctt gtg      5274
Pro Trp Asn Val Val Pro Glu Lys Ala His Leu Leu Ser Leu Val
    1745            1750                1755
```

| | |
|---|---|
| gac gtc atg cag cgg gag gga ggc ccc agc caa atc ggg gat gcc<br>Asp Val Met Gln Arg Glu Gly Gly Pro Ser Gln Ile Gly Asp Ala<br>1760                1765                1770 | 5319 |
| ttg ggc ttt gct gtg cga tac ttg act tca gaa atg cat ggg gcg<br>Leu Gly Phe Ala Val Arg Tyr Leu Thr Ser Glu Met His Gly Ala<br>1775                1780                1785 | 5364 |
| cgc ccg gga gcc tca aag gcg gtg gtc atc ctg gtc acg gac gtc<br>Arg Pro Gly Ala Ser Lys Ala Val Val Ile Leu Val Thr Asp Val<br>1790                1795                1800 | 5409 |
| tct gtg gat tca gtg gat gca gca gct gat gcc gcc agg tcc aac<br>Ser Val Asp Ser Val Asp Ala Ala Ala Asp Ala Ala Arg Ser Asn<br>1805                1810                1815 | 5454 |
| aga gtg aca gtg ttc cct att gga att gga gat cgc tac gat gca<br>Arg Val Thr Val Phe Pro Ile Gly Ile Gly Asp Arg Tyr Asp Ala<br>1820                1825                1830 | 5499 |
| gcc cag cta cgg atc ttg gca ggc cca gca ggc gac tcc aac gtg<br>Ala Gln Leu Arg Ile Leu Ala Gly Pro Ala Gly Asp Ser Asn Val<br>1835                1840                1845 | 5544 |
| gtg aag ctc cag cga atc gaa gac ctc cct acc atg gtc acc ttg<br>Val Lys Leu Gln Arg Ile Glu Asp Leu Pro Thr Met Val Thr Leu<br>1850                1855                1860 | 5589 |
| ggc aat tcc ttc ctc cac aaa ctg tgc tct gga ttt gtt agg att<br>Gly Asn Ser Phe Leu His Lys Leu Cys Ser Gly Phe Val Arg Ile<br>1865                1870                1875 | 5634 |
| tgc atg gat gag gat ggg aat gag aag agg ccc ggg gac gtc tgg<br>Cys Met Asp Glu Asp Gly Asn Glu Lys Arg Pro Gly Asp Val Trp<br>1880                1885                1890 | 5679 |
| acc ttg cca gac cag tgc cac acc gtg act tgc cag cca gat ggc<br>Thr Leu Pro Asp Gln Cys His Thr Val Thr Cys Gln Pro Asp Gly<br>1895                1900                1905 | 5724 |
| cag acc ttg ctg aag agt cat cgg gtc aac tgt gac cgg ggg ctg<br>Gln Thr Leu Leu Lys Ser His Arg Val Asn Cys Asp Arg Gly Leu<br>1910                1915                1920 | 5769 |
| agg cct tcg tgc cct aac agc cag tcc cct gtt aaa gtg gaa gag<br>Arg Pro Ser Cys Pro Asn Ser Gln Ser Pro Val Lys Val Glu Glu<br>1925                1930                1935 | 5814 |
| acc tgt ggc tgc cgc tgg acc tgc ccc tgc gtg tgc aca ggc agc<br>Thr Cys Gly Cys Arg Trp Thr Cys Pro Cys Val Cys Thr Gly Ser<br>1940                1945                1950 | 5859 |
| tcc act cgg cac atc gtg acc ttt gat ggg cag aat ttc aag ctg<br>Ser Thr Arg His Ile Val Thr Phe Asp Gly Gln Asn Phe Lys Leu<br>1955                1960                1965 | 5904 |
| act ggc agc tgt tct tat gtc cta ttt caa aac aag gag cag gac<br>Thr Gly Ser Cys Ser Tyr Val Leu Phe Gln Asn Lys Glu Gln Asp<br>1970                1975                1980 | 5949 |
| ctg gag gtg att ctc cat aat ggt gcc tgc agc cct gga gca agg<br>Leu Glu Val Ile Leu His Asn Gly Ala Cys Ser Pro Gly Ala Arg<br>1985                1990                1995 | 5994 |
| cag ggc tgc atg aaa tcc atc gag gtg aag cac agt gcc ctc tcc<br>Gln Gly Cys Met Lys Ser Ile Glu Val Lys His Ser Ala Leu Ser<br>2000                2005                2010 | 6039 |
| gtc gag ctg cac agt gac atg gag gtg acg gtg aat ggg aga ctg<br>Val Glu Leu His Ser Asp Met Glu Val Thr Val Asn Gly Arg Leu<br>2015                2020                2025 | 6084 |
| gtc tct gtt cct tac gtg ggt ggg aac atg gaa gtc aac gtt tat<br>Val Ser Val Pro Tyr Val Gly Gly Asn Met Glu Val Asn Val Tyr<br>2030                2035                2040 | 6129 |
| ggt gcc atc atg cat gag gtc aga ttc aat cac ctt ggt cac atc<br>Gly Ala Ile Met His Glu Val Arg Phe Asn His Leu Gly His Ile<br>2045                2050                2055 | 6174 |

```
ttc aca ttc act cca caa aac aat gag ttc caa ctg cag ctc agc        6219
Phe Thr Phe Thr Pro Gln Asn Asn Glu Phe Gln Leu Gln Leu Ser
    2060                2065                2070 ccc aag act ttt gct tca aag acg tat ggt ctg tgt ggg atc tgt        6264
Pro Lys Thr Phe Ala Ser Lys Thr Tyr Gly Leu Cys Gly Ile Cys
    2075                2080                2085 gat gag aac gga gcc aat gac ttc atg ctg agg gat ggc aca gtc        6309
Asp Glu Asn Gly Ala Asn Asp Phe Met Leu Arg Asp Gly Thr Val
    2090                2095                2100 acc aca gac tgg aaa aca ctt gtt cag gaa tgg act gtg cag cgg        6354
Thr Thr Asp Trp Lys Thr Leu Val Gln Glu Trp Thr Val Gln Arg
    2105                2110                2115 cca ggg cag acg tgc cag ccc atc ctg gag gag cag tgt ctt gtc        6399
Pro Gly Gln Thr Cys Gln Pro Ile Leu Glu Glu Gln Cys Leu Val
    2120                2125                2130 ccc gac agc tcc cac tgc cag gtc ctc ctc tta cca ctg ttt gct        6444
Pro Asp Ser Ser His Cys Gln Val Leu Leu Leu Pro Leu Phe Ala
    2135                2140                2145 gaa tgc cac aag gtc ctg gct cca gcc aca ttc tat gcc atc tgc        6489
Glu Cys His Lys Val Leu Ala Pro Ala Thr Phe Tyr Ala Ile Cys
    2150                2155                2160 cag cag gac agt tgc cac cag gag caa gtg tgt gag gtg atc gcc        6534
Gln Gln Asp Ser Cys His Gln Glu Gln Val Cys Glu Val Ile Ala
    2165                2170                2175 tct tat gcc cac ctc tgt cgg acc aac ggg gtc tgc gtt gac tgg        6579
Ser Tyr Ala His Leu Cys Arg Thr Asn Gly Val Cys Val Asp Trp
    2180                2185                2190 agg aca cct gat ttc tgt gct atg tca tgc cca cca tct ctg gtt        6624
Arg Thr Pro Asp Phe Cys Ala Met Ser Cys Pro Pro Ser Leu Val
    2195                2200                2205 tat aac cac tgt gag cat ggc tgt ccc cgg cac tgt gat ggc aac        6669
Tyr Asn His Cys Glu His Gly Cys Pro Arg His Cys Asp Gly Asn
    2210                2215                2220 gtg agc tcc tgt ggg gac cat ccc tcc gaa ggc tgt ttc tgc cct        6714
Val Ser Ser Cys Gly Asp His Pro Ser Glu Gly Cys Phe Cys Pro
    2225                2230                2235 cca gat aaa gtc atg ttg gaa ggc agc tgt gtc cct gaa gag gcc        6759
Pro Asp Lys Val Met Leu Glu Gly Ser Cys Val Pro Glu Glu Ala
    2240                2245                2250 tgc act cag tgc att ggt gag gat gga gtc cag cac cag ttc ctg        6804
Cys Thr Gln Cys Ile Gly Glu Asp Gly Val Gln His Gln Phe Leu
    2255                2260                2265 gaa gcc tgg gtc ccg gac cac cag ccc tgt cag atc tgc aca tgc        6849
Glu Ala Trp Val Pro Asp His Gln Pro Cys Gln Ile Cys Thr Cys
    2270                2275                2280 ctc agc ggg cgg aag gtc aac tgc aca acg cag ccc tgc ccc acg        6894
Leu Ser Gly Arg Lys Val Asn Cys Thr Thr Gln Pro Cys Pro Thr
    2285                2290                2295 gcc aaa gct ccc acg tgt ggc ctg tgt gaa gta gcc cgc ctc cgc        6939
Ala Lys Ala Pro Thr Cys Gly Leu Cys Glu Val Ala Arg Leu Arg
    2300                2305                2310 cag aat gca gac cag tgc tgc ccc gag tat gag tgt gtg tgt gac        6984
Gln Asn Ala Asp Gln Cys Cys Pro Glu Tyr Glu Cys Val Cys Asp
    2315                2320                2325 cca gtg agc tgt gac ctg ccc cca gtg cct cac tgt gaa cgt ggc        7029
Pro Val Ser Cys Asp Leu Pro Pro Val Pro His Cys Glu Arg Gly
    2330                2335                2340 ctc cag ccc aca ctg acc aac cct ggc gag tgc aga ccc aac ttc        7074
Leu Gln Pro Thr Leu Thr Asn Pro Gly Glu Cys Arg Pro Asn Phe
```

-continued

|  |  |  |  |
|---|---|---|---|
| acc tgc gcc tgc agg aag gag gag tgc aaa aga gtg tcc cca ccc<br>Thr Cys Ala Cys Arg Lys Glu Glu Cys Lys Arg Val Ser Pro Pro<br>2360     2365     2370 | 7119 |
| tcc tgc ccc ccg cac cgt ttg ccc acc ctt cgg aag acc cag tgc<br>Ser Cys Pro Pro His Arg Leu Pro Thr Leu Arg Lys Thr Gln Cys<br>2375     2380     2385 | 7164 |
| tgt gat gag tat gag tgt gcc tgc aac tgt gtc aac tcc aca gtg<br>Cys Asp Glu Tyr Glu Cys Ala Cys Asn Cys Val Asn Ser Thr Val<br>2390     2395     2400 | 7209 |
| agc tgt ccc ctt ggg tac ttg gcc tca acc gcc acc aat gac tgt<br>Ser Cys Pro Leu Gly Tyr Leu Ala Ser Thr Ala Thr Asn Asp Cys<br>2405     2410     2415 | 7254 |
| ggc tgt acc aca acc acc tgc ctt ccc gac aag gtg tgt gtc cac<br>Gly Cys Thr Thr Thr Thr Cys Leu Pro Asp Lys Val Cys Val His<br>2420     2425     2430 | 7299 |
| cga agc acc atc tac cct gtg ggc cag ttc tgg gag gag ggc tgc<br>Arg Ser Thr Ile Tyr Pro Val Gly Gln Phe Trp Glu Glu Gly Cys<br>2435     2440     2445 | 7344 |
| gat gtg tgc acc tgc acc gac atg gag gat gcc gtg atg ggc ctc<br>Asp Val Cys Thr Cys Thr Asp Met Glu Asp Ala Val Met Gly Leu<br>2450     2455     2460 | 7389 |
| cgc gtg gcc cag tgc tcc cag aag ccc tgt gag gac agc tgt cgg<br>Arg Val Ala Gln Cys Ser Gln Lys Pro Cys Glu Asp Ser Cys Arg<br>2465     2470     2475 | 7434 |
| tcg ggc ttc act tac gtt ctg cat gaa ggc gag tgc tgt gga agg<br>Ser Gly Phe Thr Tyr Val Leu His Glu Gly Glu Cys Cys Gly Arg<br>2480     2485     2490 | 7479 |
| tgc ctg cca tct gcc tgt gag gtg gtg act ggc tca ccg cgg ggg<br>Cys Leu Pro Ser Ala Cys Glu Val Val Thr Gly Ser Pro Arg Gly<br>2495     2500     2505 | 7524 |
| gac tcc cag tct tcc tgg aag agt gtc ggc tcc cag tgg gcc tcc<br>Asp Ser Gln Ser Ser Trp Lys Ser Val Gly Ser Gln Trp Ala Ser<br>2510     2515     2520 | 7569 |
| ccg gag aac ccc tgc ctc atc aat gag tgt gtc cga gtg aag gag<br>Pro Glu Asn Pro Cys Leu Ile Asn Glu Cys Val Arg Val Lys Glu<br>2525     2530     2535 | 7614 |
| gag gtc ttt ata caa caa agg aac gtc tcc tgc ccc cag ctg gag<br>Glu Val Phe Ile Gln Gln Arg Asn Val Ser Cys Pro Gln Leu Glu<br>2540     2545     2550 | 7659 |
| gtc cct gtc tgc ccc tcg ggc ttt cag ctg agc tgt aag acc tca<br>Val Pro Val Cys Pro Ser Gly Phe Gln Leu Ser Cys Lys Thr Ser<br>2555     2560     2565 | 7704 |
| gcg tgc tgc cca agc tgt cgc tgt gag cgc atg gag gcc tgc atg<br>Ala Cys Cys Pro Ser Cys Arg Cys Glu Arg Met Glu Ala Cys Met<br>2570     2575     2580 | 7749 |
| ctc aat ggc act gtc att ggg ccc ggg aag act gtg atg atc gat<br>Leu Asn Gly Thr Val Ile Gly Pro Gly Lys Thr Val Met Ile Asp<br>2585     2590     2595 | 7794 |
| gtg tgc acg acc tgc cgc tgc atg gtg cag gtg ggg gtc atc tct<br>Val Cys Thr Thr Cys Arg Cys Met Val Gln Val Gly Val Ile Ser<br>2600     2605     2610 | 7839 |
| gga ttc aag ctg gag tgc agg aag acc acc tgc aac ccc tgc ccc<br>Gly Phe Lys Leu Glu Cys Arg Lys Thr Thr Cys Asn Pro Cys Pro<br>2615     2620     2625 | 7884 |
| ctg ggt tac aag gaa gaa aat aac aca ggt gaa tgt tgt ggg aga<br>Leu Gly Tyr Lys Glu Glu Asn Asn Thr Gly Glu Cys Cys Gly Arg<br>2630     2635     2640 | 7929 |
| tgt ttg cct acg gct tgc acc att cag cta aga gga gga cag atc | 7974 |

| | | | | | | | | | | | |
|---|---|---|---|---|---|---|---|---|---|---|---|
| Cys | Leu | Pro | Thr | Ala | Cys | Thr | Ile | Gln | Leu | Arg | Gly | Gly | Gln | Ile |
| | 2645 | | | | 2650 | | | | 2655 | | |

```
atg aca ctg aag cgt gat gag acg ctc cag gat ggc tgt gat act      8019
Met Thr Leu Lys Arg Asp Glu Thr Leu Gln Asp Gly Cys Asp Thr
    2660                2665                2670 cac ttc tgc aag gtc aat gag aga gga gag tac ttc tgg gag aag      8064
His Phe Cys Lys Val Asn Glu Arg Gly Glu Tyr Phe Trp Glu Lys
    2675                2680                2685 agg gtc aca ggc tgc cca ccc ttt gat gaa cac aag tgt ctg gct      8109
Arg Val Thr Gly Cys Pro Pro Phe Asp Glu His Lys Cys Leu Ala
    2690                2695                2700 gag gga ggt aaa att atg aaa att cca ggc acc tgc tgt gac aca      8154
Glu Gly Gly Lys Ile Met Lys Ile Pro Gly Thr Cys Cys Asp Thr
    2705                2710                2715 tgt gag gag cct gag tgc aac gac atc act gcc agg ctg cag tat      8199
Cys Glu Glu Pro Glu Cys Asn Asp Ile Thr Ala Arg Leu Gln Tyr
    2720                2725                2730 gtc aag gtg gga agc tgt aag tct gaa gta gag gtg gat atc cac      8244
Val Lys Val Gly Ser Cys Lys Ser Glu Val Glu Val Asp Ile His
    2735                2740                2745 tac tgc cag ggc aaa tgt gcc agc aaa gcc atg tac tcc att gac      8289
Tyr Cys Gln Gly Lys Cys Ala Ser Lys Ala Met Tyr Ser Ile Asp
    2750                2755                2760 atc aac gat gtg cag gac cag tgc tcc tgc tgt tct ccg aca cgg      8334
Ile Asn Asp Val Gln Asp Gln Cys Ser Cys Cys Ser Pro Thr Arg
    2765                2770                2775 acg gag ccc atg cag gtg gcc ctg cac tgc acc aat ggc tct gtt      8379
Thr Glu Pro Met Gln Val Ala Leu His Cys Thr Asn Gly Ser Val
    2780                2785                2790 gtg tac cat gag gtt ctc aat gcc atg gag tgc aaa tgc tcc ccc      8424
Val Tyr His Glu Val Leu Asn Ala Met Glu Cys Lys Cys Ser Pro
    2795                2800                2805 agg aag tgc agc aag tga                                          8442
Arg Lys Cys Ser Lys
    2810

<210> SEQ ID NO 4
<211> LENGTH: 2813
<212> TYPE: PRT
<213> ORGANISM: Homo sapiens

<400> SEQUENCE: 4

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
        50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
        115                 120                 125
```

-continued

Leu Ser Gly Glu Ala Tyr Gly Phe Val Ala Arg Ile Asp Gly Ser Gly
130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Ser Ser
        195                 200                 205

Ser Cys Asn Ile Ser Ser Gly Glu Met Gln Lys Gly Leu Trp Glu Gln
210                 215                 220

Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
                245                 250                 255

Cys Ala Gly Gly Leu Glu Cys Ala Cys Pro Ala Leu Leu Glu Tyr Ala
                260                 265                 270

Arg Thr Cys Ala Gln Glu Gly Met Val Leu Tyr Gly Trp Thr Asp His
        275                 280                 285

Ser Ala Cys Ser Pro Val Cys Pro Ala Gly Met Glu Tyr Arg Gln Cys
    290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
                325                 330                 335

Leu Asp Glu Gly Leu Cys Val Glu Ser Thr Glu Cys Pro Cys Val His
                340                 345                 350

Ser Gly Lys Arg Tyr Pro Pro Gly Thr Ser Leu Ser Arg Asp Cys Asn
        355                 360                 365

Thr Cys Ile Cys Arg Asn Ser Gln Trp Ile Cys Ser Asn Glu Glu Cys
    370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
                405                 410                 415

Asp Cys Gln Asp His Ser Phe Ser Ile Val Ile Glu Thr Val Gln Cys
                420                 425                 430

Ala Asp Asp Arg Asp Ala Val Cys Thr Arg Ser Val Thr Val Arg Leu
        435                 440                 445

Pro Gly Leu His Asn Ser Leu Val Lys Leu Lys His Gly Ala Gly Val
    450                 455                 460

Ala Met Asp Gly Gln Asp Val Gln Leu Pro Leu Leu Lys Gly Asp Leu
465                 470                 475                 480

Arg Ile Gln His Thr Val Thr Ala Ser Val Arg Leu Ser Tyr Gly Glu
                485                 490                 495

Asp Leu Gln Met Asp Trp Asp Gly Arg Gly Arg Leu Leu Val Lys Leu
                500                 505                 510

Ser Pro Val Tyr Ala Gly Lys Thr Cys Gly Leu Cys Gly Asn Tyr Asn
        515                 520                 525

Gly Asn Gln Gly Asp Asp Phe Leu Thr Pro Ser Gly Leu Ala Glu Pro
    530                 535                 540

Arg Val Glu Asp Phe Gly Asn Ala Trp Lys Leu His Gly Asp Cys Gln

```
            545                 550                 555                 560
Asp Leu Gln Lys Gln His Ser Asp Pro Cys Ala Leu Asn Pro Arg Met
                565                 570                 575

Thr Arg Phe Ser Glu Glu Ala Cys Ala Val Leu Thr Ser Pro Thr Phe
                580                 585                 590

Glu Ala Cys His Arg Ala Val Ser Pro Leu Pro Tyr Leu Arg Asn Cys
                595                 600                 605

Arg Tyr Asp Val Cys Ser Cys Ser Asp Gly Arg Glu Cys Leu Cys Gly
                610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
                645                 650                 655

Val Tyr Leu Gln Cys Gly Thr Pro Cys Asn Leu Thr Cys Arg Ser Leu
                660                 665                 670

Ser Tyr Pro Asp Glu Glu Cys Asn Glu Ala Cys Leu Glu Gly Cys Phe
                675                 680                 685

Cys Pro Pro Gly Leu Tyr Met Asp Glu Arg Gly Asp Cys Val Pro Lys
                690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
                740                 745                 750

Leu Ser Ser Pro Leu Ser His Arg Ser Lys Arg Ser Leu Ser Cys Arg
                755                 760                 765

Pro Pro Met Val Lys Leu Val Cys Pro Ala Asp Asn Leu Arg Ala Glu
                770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
                820                 825                 830

Gly Lys Glu Tyr Ala Pro Gly Glu Thr Val Lys Ile Gly Cys Asn Thr
                835                 840                 845

Cys Val Cys Arg Asp Arg Lys Trp Asn Cys Thr Asp His Val Cys Asp
                850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
                900                 905                 910

Gly Cys Ser His Pro Ser Val Lys Cys Lys Lys Arg Val Thr Ile Leu
                915                 920                 925

Val Glu Gly Gly Glu Ile Glu Leu Phe Asp Gly Glu Val Asn Val Lys
                930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975
```

```
His Leu Ser Ile Ser Val Val Leu Lys Gln Thr Tyr Gln Glu Lys Val
            980                 985                 990

Cys Gly Leu Cys Gly Asn Phe Asp Gly Ile Gln Asn Asn Asp Leu Thr
        995                 1000                1005

Ser Ser Asn Leu Gln Val Glu Glu Asp Pro Val Asp Phe Gly Asn
    1010                1015                1020

Ser Trp Lys Val Ser Ser Gln Cys Ala Asp Thr Arg Lys Val Pro
    1025                1030                1035

Leu Asp Ser Ser Pro Ala Thr Cys His Asn Asn Ile Met Lys Gln
    1040                1045                1050

Thr Met Val Asp Ser Ser Cys Arg Ile Leu Thr Ser Asp Val Phe
    1055                1060                1065

Gln Asp Cys Asn Lys Leu Val Asp Pro Glu Pro Tyr Leu Asp Val
    1070                1075                1080

Cys Ile Tyr Asp Thr Cys Ser Cys Glu Ser Ile Gly Asp Cys Ala
    1085                1090                1095

Cys Phe Cys Asp Thr Ile Ala Ala Tyr Ala His Val Cys Ala Gln
    1100                1105                1110

His Gly Lys Val Val Thr Trp Arg Thr Ala Thr Leu Cys Pro Gln
    1115                1120                1125

Ser Cys Glu Glu Arg Asn Leu Arg Glu Asn Gly Tyr Glu Cys Glu
    1130                1135                1140

Trp Arg Tyr Asn Ser Cys Ala Pro Ala Cys Gln Val Thr Cys Gln
    1145                1150                1155

His Pro Glu Pro Leu Ala Cys Pro Val Gln Cys Val Glu Gly Cys
    1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro Gly Gly Leu Val Val Pro Pro Thr
    1235                1240                1245

Asp Ala Pro Val Ser Pro Thr Thr Leu Tyr Val Glu Asp Ile Ser
    1250                1255                1260

Glu Pro Pro Leu His Asp Phe Tyr Cys Ser Arg Leu Leu Asp Leu
    1265                1270                1275

Val Phe Leu Leu Asp Gly Ser Ser Arg Leu Ser Glu Ala Glu Phe
    1280                1285                1290

Glu Val Leu Lys Ala Phe Val Val Asp Met Met Glu Arg Leu Arg
    1295                1300                1305

Ile Ser Gln Lys Trp Val Arg Val Ala Val Val Glu Tyr His Asp
    1310                1315                1320

Gly Ser His Ala Tyr Ile Gly Leu Lys Asp Arg Lys Arg Pro Ser
    1325                1330                1335

Glu Leu Arg Arg Ile Ala Ser Gln Val Lys Tyr Ala Gly Ser Gln
    1340                1345                1350

Val Ala Ser Thr Ser Glu Val Leu Lys Tyr Thr Leu Phe Gln Ile
    1355                1360                1365
```

```
Phe Ser Lys Ile Asp Arg Pro Glu Ala Ser Arg Ile Ala Leu Leu
1370                1375                1380

Leu Met Ala Ser Gln Glu Pro Gln Arg Met Ser Arg Asn Phe Val
1385                1390                1395

Arg Tyr Val Gln Gly Leu Lys Lys Lys Val Ile Val Ile Pro
1400                1405                1410

Val Gly Ile Gly Pro His Ala Asn Leu Lys Gln Ile Arg Leu Ile
1415                1420                1425

Glu Lys Gln Ala Pro Glu Asn Lys Ala Phe Val Leu Ser Ser Val
1430                1435                1440

Asp Glu Leu Glu Gln Gln Arg Asp Glu Ile Val Ser Tyr Leu Cys
1445                1450                1455

Asp Leu Ala Pro Glu Ala Pro Pro Pro Thr Leu Pro Pro His Met
1460                1465                1470

Ala Gln Val Thr Val Gly Pro Gly Leu Leu Gly Val Ser Thr Leu
1475                1480                1485

Gly Pro Lys Arg Asn Ser Met Val Leu Asp Val Ala Phe Val Leu
1490                1495                1500

Glu Gly Ser Asp Lys Ile Gly Glu Ala Asp Phe Asn Arg Ser Lys
1505                1510                1515

Glu Phe Met Glu Glu Val Ile Gln Arg Met Asp Val Gly Gln Asp
1520                1525                1530

Ser Ile His Val Thr Val Leu Gln Tyr Ser Tyr Met Val Thr Val
1535                1540                1545

Glu Tyr Pro Phe Ser Glu Ala Gln Ser Lys Gly Asp Ile Leu Gln
1550                1555                1560

Arg Val Arg Glu Ile Arg Tyr Gln Gly Gly Asn Arg Thr Asn Thr
1565                1570                1575

Gly Leu Ala Leu Arg Tyr Leu Ser Asp His Ser Phe Leu Val Ser
1580                1585                1590

Gln Gly Asp Arg Glu Gln Ala Pro Asn Leu Val Tyr Met Val Thr
1595                1600                1605

Gly Asn Pro Ala Ser Asp Glu Ile Lys Arg Leu Pro Gly Asp Ile
1610                1615                1620

Gln Val Val Pro Ile Gly Val Gly Pro Asn Ala Asn Val Gln Glu
1625                1630                1635

Leu Glu Arg Ile Gly Trp Pro Asn Ala Pro Ile Leu Ile Gln Asp
1640                1645                1650

Phe Glu Thr Leu Pro Arg Glu Ala Pro Asp Leu Val Leu Gln Arg
1655                1660                1665

Cys Cys Ser Gly Glu Gly Leu Gln Ile Pro Thr Leu Ser Pro Ala
1670                1675                1680

Pro Asp Cys Ser Gln Pro Leu Asp Val Ile Leu Leu Leu Asp Gly
1685                1690                1695

Ser Ser Ser Phe Pro Ala Ser Tyr Phe Asp Glu Met Lys Ser Phe
1700                1705                1710

Ala Lys Ala Phe Ile Ser Lys Ala Asn Ile Gly Pro Arg Leu Thr
1715                1720                1725

Gln Val Ser Val Leu Gln Tyr Gly Ser Ile Thr Thr Ile Asp Val
1730                1735                1740

Pro Trp Asn Val Val Pro Glu Lys Ala His Leu Leu Ser Leu Val
1745                1750                1755

Asp Val Met Gln Arg Glu Gly Gly Pro Ser Gln Ile Gly Asp Ala
```

```
            1760                1765                1770
Leu Gly Phe Ala Val Arg Tyr Leu Thr Ser Glu Met His Gly Ala
            1775                1780                1785

Arg Pro Gly Ala Ser Lys Ala Val Val Ile Leu Val Thr Asp Val
            1790                1795                1800

Ser Val Asp Ser Val Asp Ala Ala Asp Ala Ala Arg Ser Asn
            1805                1810                1815

Arg Val Thr Val Phe Pro Ile Gly Ile Gly Asp Arg Tyr Asp Ala
            1820                1825                1830

Ala Gln Leu Arg Ile Leu Ala Gly Pro Ala Gly Asp Ser Asn Val
            1835                1840                1845

Val Lys Leu Gln Arg Ile Glu Asp Leu Pro Thr Met Val Thr Leu
            1850                1855                1860

Gly Asn Ser Phe Leu His Lys Leu Cys Ser Gly Phe Val Arg Ile
            1865                1870                1875

Cys Met Asp Glu Asp Gly Asn Glu Lys Arg Pro Gly Asp Val Trp
            1880                1885                1890

Thr Leu Pro Asp Gln Cys His Thr Val Thr Cys Gln Pro Asp Gly
            1895                1900                1905

Gln Thr Leu Leu Lys Ser His Arg Val Asn Cys Asp Arg Gly Leu
            1910                1915                1920

Arg Pro Ser Cys Pro Asn Ser Gln Ser Pro Val Lys Val Glu Glu
            1925                1930                1935

Thr Cys Gly Cys Arg Trp Thr Cys Pro Cys Val Cys Thr Gly Ser
            1940                1945                1950

Ser Thr Arg His Ile Val Thr Phe Asp Gly Gln Asn Phe Lys Leu
            1955                1960                1965

Thr Gly Ser Cys Ser Tyr Val Leu Phe Gln Asn Lys Glu Gln Asp
            1970                1975                1980

Leu Glu Val Ile Leu His Asn Gly Ala Cys Ser Pro Gly Ala Arg
            1985                1990                1995

Gln Gly Cys Met Lys Ser Ile Glu Val Lys His Ser Ala Leu Ser
            2000                2005                2010

Val Glu Leu His Ser Asp Met Glu Val Thr Val Asn Gly Arg Leu
            2015                2020                2025

Val Ser Val Pro Tyr Val Gly Gly Asn Met Glu Val Asn Val Tyr
            2030                2035                2040

Gly Ala Ile Met His Glu Val Arg Phe Asn His Leu Gly His Ile
            2045                2050                2055

Phe Thr Phe Thr Pro Gln Asn Asn Glu Phe Gln Leu Gln Leu Ser
            2060                2065                2070

Pro Lys Thr Phe Ala Ser Lys Thr Tyr Gly Leu Cys Gly Ile Cys
            2075                2080                2085

Asp Glu Asn Gly Ala Asn Asp Phe Met Leu Arg Asp Gly Thr Val
            2090                2095                2100

Thr Thr Asp Trp Lys Thr Leu Val Gln Glu Trp Thr Val Gln Arg
            2105                2110                2115

Pro Gly Gln Thr Cys Gln Pro Ile Leu Glu Glu Gln Cys Leu Val
            2120                2125                2130

Pro Asp Ser Ser His Cys Gln Val Leu Leu Leu Pro Leu Phe Ala
            2135                2140                2145

Glu Cys His Lys Val Leu Ala Pro Ala Thr Phe Tyr Ala Ile Cys
            2150                2155                2160
```

-continued

```
Gln Gln Asp Ser Cys His Gln Glu Gln Val Cys Glu Val Ile Ala
    2165                2170                2175

Ser Tyr Ala His Leu Cys Arg Thr Asn Gly Val Cys Val Asp Trp
    2180                2185                2190

Arg Thr Pro Asp Phe Cys Ala Met Ser Cys Pro Pro Ser Leu Val
    2195                2200                2205

Tyr Asn His Cys Glu His Gly Cys Pro Arg His Cys Asp Gly Asn
    2210                2215                2220

Val Ser Ser Cys Gly Asp His Pro Ser Glu Gly Cys Phe Cys Pro
    2225                2230                2235

Pro Asp Lys Val Met Leu Glu Gly Ser Cys Val Pro Glu Glu Ala
    2240                2245                2250

Cys Thr Gln Cys Ile Gly Glu Asp Gly Val Gln His Gln Phe Leu
    2255                2260                2265

Glu Ala Trp Val Pro Asp His Gln Pro Cys Gln Ile Cys Thr Cys
    2270                2275                2280

Leu Ser Gly Arg Lys Val Asn Cys Thr Thr Gln Pro Cys Pro Thr
    2285                2290                2295

Ala Lys Ala Pro Thr Cys Gly Leu Cys Glu Val Ala Arg Leu Arg
    2300                2305                2310

Gln Asn Ala Asp Gln Cys Cys Pro Glu Tyr Glu Cys Val Cys Asp
    2315                2320                2325

Pro Val Ser Cys Asp Leu Pro Pro Val Pro His Cys Glu Arg Gly
    2330                2335                2340

Leu Gln Pro Thr Leu Thr Asn Pro Gly Glu Cys Arg Pro Asn Phe
    2345                2350                2355

Thr Cys Ala Cys Arg Lys Glu Glu Cys Lys Arg Val Ser Pro Pro
    2360                2365                2370

Ser Cys Pro Pro His Arg Leu Pro Thr Leu Arg Lys Thr Gln Cys
    2375                2380                2385

Cys Asp Glu Tyr Glu Cys Ala Cys Asn Cys Val Asn Ser Thr Val
    2390                2395                2400

Ser Cys Pro Leu Gly Tyr Leu Ala Ser Thr Ala Thr Asn Asp Cys
    2405                2410                2415

Gly Cys Thr Thr Thr Thr Cys Leu Pro Asp Lys Val Cys Val His
    2420                2425                2430

Arg Ser Thr Ile Tyr Pro Val Gly Gln Phe Trp Glu Glu Gly Cys
    2435                2440                2445

Asp Val Cys Thr Cys Thr Asp Met Glu Asp Ala Val Met Gly Leu
    2450                2455                2460

Arg Val Ala Gln Cys Ser Gln Lys Pro Cys Glu Asp Ser Cys Arg
    2465                2470                2475

Ser Gly Phe Thr Tyr Val Leu His Glu Gly Glu Cys Cys Gly Arg
    2480                2485                2490

Cys Leu Pro Ser Ala Cys Glu Val Val Thr Gly Ser Pro Arg Gly
    2495                2500                2505

Asp Ser Gln Ser Ser Trp Lys Ser Val Gly Ser Gln Trp Ala Ser
    2510                2515                2520

Pro Glu Asn Pro Cys Leu Ile Asn Glu Cys Val Arg Val Lys Glu
    2525                2530                2535

Glu Val Phe Ile Gln Gln Arg Asn Val Ser Cys Pro Gln Leu Glu
    2540                2545                2550
```

```
Val Pro Val Cys Pro Ser Gly Phe Gln Leu Ser Cys Lys Thr Ser
    2555            2560                2565

Ala Cys Cys Pro Ser Cys Arg Cys Glu Arg Met Glu Ala Cys Met
2570                2575                2580

Leu Asn Gly Thr Val Ile Gly Pro Gly Lys Thr Val Met Ile Asp
    2585            2590                2595

Val Cys Thr Thr Cys Arg Cys Met Val Gln Val Gly Val Ile Ser
2600                2605                2610

Gly Phe Lys Leu Glu Cys Arg Lys Thr Thr Cys Asn Pro Cys Pro
    2615            2620                2625

Leu Gly Tyr Lys Glu Glu Asn Asn Thr Gly Glu Cys Cys Gly Arg
    2630            2635                2640

Cys Leu Pro Thr Ala Cys Thr Ile Gln Leu Arg Gly Gly Gln Ile
    2645            2650                2655

Met Thr Leu Lys Arg Asp Glu Thr Leu Gln Asp Gly Cys Asp Thr
    2660            2665                2670

His Phe Cys Lys Val Asn Glu Arg Gly Glu Tyr Phe Trp Glu Lys
    2675            2680                2685

Arg Val Thr Gly Cys Pro Pro Phe Asp Glu His Lys Cys Leu Ala
    2690            2695                2700

Glu Gly Gly Lys Ile Met Lys Ile Pro Gly Thr Cys Cys Asp Thr
    2705            2710                2715

Cys Glu Glu Pro Glu Cys Asn Asp Ile Thr Ala Arg Leu Gln Tyr
    2720            2725                2730

Val Lys Val Gly Ser Cys Lys Ser Glu Val Glu Val Asp Ile His
    2735            2740                2745

Tyr Cys Gln Gly Lys Cys Ala Ser Lys Ala Met Tyr Ser Ile Asp
    2750            2755                2760

Ile Asn Asp Val Gln Asp Gln Cys Ser Cys Cys Ser Pro Thr Arg
    2765            2770                2775

Thr Glu Pro Met Gln Val Ala Leu His Cys Thr Asn Gly Ser Val
    2780            2785                2790

Val Tyr His Glu Val Leu Asn Ala Met Glu Cys Lys Cys Ser Pro
    2795            2800                2805

Arg Lys Cys Ser Lys
    2810

<210> SEQ ID NO 5
<211> LENGTH: 1444
<212> TYPE: PRT
<213> ORGANISM: Artificial Sequence
<220> FEATURE:
<223> OTHER INFORMATION: amino acid sequence of a single chain factor
      viii molecule

<400> SEQUENCE: 5

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
                20                  25                  30

Arg Val Pro Lys Ser Phe Pro Phe Asn Thr Ser Val Val Tyr Lys Lys
            35                  40                  45

Thr Leu Phe Val Glu Phe Thr Asp His Leu Phe Asn Ile Ala Lys Pro
        50                  55                  60

Arg Pro Pro Trp Met Gly Leu Leu Gly Pro Thr Ile Gln Ala Glu Val
65                  70                  75                  80
```

```
Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
            115                 120                 125

Phe Pro Gly Gly Ser His Thr Tyr Val Trp Gln Val Leu Lys Glu Asn
130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205

His Ser Glu Thr Lys Asn Ser Leu Met Gln Asp Arg Asp Ala Ala Ser
        210                 215                 220

Ala Arg Ala Trp Pro Lys Met His Thr Val Asn Gly Tyr Val Asn Arg
225                 230                 235                 240

Ser Leu Pro Gly Leu Ile Gly Cys His Arg Lys Ser Val Tyr Trp His
                245                 250                 255

Val Ile Gly Met Gly Thr Thr Pro Glu Val His Ser Ile Phe Leu Glu
            260                 265                 270

Gly His Thr Phe Leu Val Arg Asn His Arg Gln Ala Ser Leu Glu Ile
        275                 280                 285

Ser Pro Ile Thr Phe Leu Thr Ala Gln Thr Leu Leu Met Asp Leu Gly
        290                 295                 300

Gln Phe Leu Leu Phe Cys His Ile Ser Ser His Gln His Asp Gly Met
305                 310                 315                 320

Glu Ala Tyr Val Lys Val Asp Ser Cys Pro Glu Pro Gln Leu Arg
                325                 330                 335

Met Lys Asn Asn Glu Glu Ala Glu Asp Tyr Asp Asp Leu Thr Asp
                340                 345                 350

Ser Glu Met Asp Val Val Arg Phe Asp Asp Asn Ser Pro Ser Phe
            355                 360                 365

Ile Gln Ile Arg Ser Val Ala Lys Lys His Pro Lys Thr Trp Val His
        370                 375                 380

Tyr Ile Ala Ala Glu Glu Asp Trp Asp Tyr Ala Pro Leu Val Leu
385                 390                 395                 400

Ala Pro Asp Asp Arg Ser Tyr Lys Ser Gln Tyr Leu Asn Asn Gly Pro
                405                 410                 415

Gln Arg Ile Gly Arg Lys Tyr Lys Lys Val Arg Phe Met Ala Tyr Thr
            420                 425                 430

Asp Glu Thr Phe Lys Thr Arg Glu Ala Ile Gln His Glu Ser Gly Ile
            435                 440                 445

Leu Gly Pro Leu Leu Tyr Gly Glu Val Gly Asp Thr Leu Leu Ile Ile
        450                 455                 460

Phe Lys Asn Gln Ala Ser Arg Pro Tyr Asn Ile Tyr Pro His Gly Ile
465                 470                 475                 480

Thr Asp Val Arg Pro Leu Tyr Ser Arg Arg Leu Pro Lys Gly Val Lys
                485                 490                 495
```

-continued

His Leu Lys Asp Phe Pro Ile Leu Pro Gly Glu Ile Phe Lys Tyr Lys
              500                 505                 510

Trp Thr Val Thr Val Glu Asp Gly Pro Thr Lys Ser Asp Pro Arg Cys
          515                 520                 525

Leu Thr Arg Tyr Tyr Ser Ser Phe Val Asn Met Glu Arg Asp Leu Ala
    530                 535                 540

Ser Gly Leu Ile Gly Pro Leu Leu Ile Cys Tyr Lys Glu Ser Val Asp
545                 550                 555                 560

Gln Arg Gly Asn Gln Ile Met Ser Asp Lys Arg Asn Val Ile Leu Phe
              565                 570                 575

Ser Val Phe Asp Glu Asn Arg Ser Trp Tyr Leu Thr Glu Asn Ile Gln
          580                 585                 590

Arg Phe Leu Pro Asn Pro Ala Gly Val Gln Leu Glu Asp Pro Glu Phe
    595                 600                 605

Gln Ala Ser Asn Ile Met His Ser Ile Asn Gly Tyr Val Phe Asp Ser
610                 615                 620

Leu Gln Leu Ser Val Cys Leu His Glu Val Ala Tyr Trp Tyr Ile Leu
625                 630                 635                 640

Ser Ile Gly Ala Gln Thr Asp Phe Leu Ser Val Phe Phe Ser Gly Tyr
              645                 650                 655

Thr Phe Lys His Lys Met Val Tyr Glu Asp Thr Leu Thr Leu Phe Pro
          660                 665                 670

Phe Ser Gly Glu Thr Val Phe Met Ser Met Glu Asn Pro Gly Leu Trp
    675                 680                 685

Ile Leu Gly Cys His Asn Ser Asp Phe Arg Asn Arg Gly Met Thr Ala
690                 695                 700

Leu Leu Lys Val Ser Ser Cys Asp Lys Asn Thr Gly Asp Tyr Tyr Glu
705                 710                 715                 720

Asp Ser Tyr Glu Asp Ile Ser Ala Tyr Leu Leu Ser Lys Asn Asn Ala
              725                 730                 735

Ile Glu Pro Arg Ser Phe Ser Gln Asn Ser Arg His Pro Ser Thr Arg
          740                 745                 750

Gln Lys Gln Phe Asn Ala Thr Thr Ile Pro Glu Asn Thr Thr Leu Gln
    755                 760                 765

Ser Asp Gln Glu Glu Ile Asp Tyr Asp Asp Thr Ile Ser Val Glu Met
770                 775                 780

Lys Lys Glu Asp Phe Asp Ile Tyr Asp Glu Asp Glu Asn Gln Ser Pro
785                 790                 795                 800

Arg Ser Phe Gln Lys Lys Thr Arg His Tyr Phe Ile Ala Ala Val Glu
              805                 810                 815

Arg Leu Trp Asp Tyr Gly Met Ser Ser Ser Pro His Val Leu Arg Asn
          820                 825                 830

Arg Ala Gln Ser Gly Ser Val Pro Gln Phe Lys Lys Val Val Phe Gln
    835                 840                 845

Glu Phe Thr Asp Gly Ser Phe Thr Gln Pro Leu Tyr Arg Gly Glu Leu
850                 855                 860

Asn Glu His Leu Gly Leu Leu Gly Pro Tyr Ile Arg Ala Glu Val Glu
865                 870                 875                 880

Asp Asn Ile Met Val Thr Phe Arg Asn Gln Ala Ser Arg Pro Tyr Ser
              885                 890                 895

Phe Tyr Ser Ser Leu Ile Ser Tyr Glu Glu Asp Gln Arg Gln Gly Ala
          900                 905                 910

Glu Pro Arg Lys Asn Phe Val Lys Pro Asn Glu Thr Lys Thr Tyr Phe

-continued

```
            915                 920                 925
Trp Lys Val Gln His His Met Ala Pro Thr Lys Asp Glu Phe Asp Cys
        930                 935                 940
Lys Ala Trp Ala Tyr Phe Ser Asp Val Asp Leu Glu Lys Asp Val His
945                 950                 955                 960
Ser Gly Leu Ile Gly Pro Leu Leu Val Cys His Thr Asn Thr Leu Asn
                965                 970                 975
Pro Ala His Gly Arg Gln Val Thr Val Gln Glu Phe Ala Leu Phe Phe
            980                 985                 990
Thr Ile Phe Asp Glu Thr Lys Ser Trp Tyr Phe Thr Glu Asn Met Glu
        995                 1000                1005
Arg Asn Cys Arg Ala Pro Cys Asn Ile Gln Met Glu Asp Pro Thr
    1010                1015                1020
Phe Lys Glu Asn Tyr Arg Phe His Ala Ile Asn Gly Tyr Ile Met
    1025                1030                1035
Asp Thr Leu Pro Gly Leu Val Met Ala Gln Asp Gln Arg Ile Arg
    1040                1045                1050
Trp Tyr Leu Leu Ser Met Gly Ser Asn Glu Asn Ile His Ser Ile
    1055                1060                1065
His Phe Ser Gly His Val Phe Thr Val Arg Lys Lys Glu Glu Tyr
    1070                1075                1080
Lys Met Ala Leu Tyr Asn Leu Tyr Pro Gly Val Phe Glu Thr Val
    1085                1090                1095
Glu Met Leu Pro Ser Lys Ala Gly Ile Trp Arg Val Glu Cys Leu
    1100                1105                1110
Ile Gly Glu His Leu His Ala Gly Met Ser Thr Leu Phe Leu Val
    1115                1120                1125
Tyr Ser Asn Lys Cys Gln Thr Pro Leu Gly Met Ala Ser Gly His
    1130                1135                1140
Ile Arg Asp Phe Gln Ile Thr Ala Ser Gly Gln Tyr Gly Gln Trp
    1145                1150                1155
Ala Pro Lys Leu Ala Arg Leu His Tyr Ser Gly Ser Ile Asn Ala
    1160                1165                1170
Trp Ser Thr Lys Glu Pro Phe Ser Trp Ile Lys Val Asp Leu Leu
    1175                1180                1185
Ala Pro Met Ile Ile His Gly Ile Lys Thr Gln Gly Ala Arg Gln
    1190                1195                1200
Lys Phe Ser Ser Leu Tyr Ile Ser Gln Phe Ile Ile Met Tyr Ser
    1205                1210                1215
Leu Asp Gly Lys Lys Trp Gln Thr Tyr Arg Gly Asn Ser Thr Gly
    1220                1225                1230
Thr Leu Met Val Phe Phe Gly Asn Val Asp Ser Ser Gly Ile Lys
    1235                1240                1245
His Asn Ile Phe Asn Pro Pro Ile Ile Ala Arg Tyr Ile Arg Leu
    1250                1255                1260
His Pro Thr His Tyr Ser Ile Arg Ser Thr Leu Arg Met Glu Leu
    1265                1270                1275
Met Gly Cys Asp Leu Asn Ser Cys Ser Met Pro Leu Gly Met Glu
    1280                1285                1290
Ser Lys Ala Ile Ser Asp Ala Gln Ile Thr Ala Ser Ser Tyr Phe
    1295                1300                1305
Thr Asn Met Phe Ala Thr Trp Ser Pro Ser Lys Ala Arg Leu His
    1310                1315                1320
```

-continued

Leu Gln Gly Arg Ser Asn Ala Trp Arg Pro Gln Val Asn Asn Pro
    1325                1330                1335

Lys Glu Trp Leu Gln Val Asp Phe Gln Lys Thr Met Lys Val Thr
    1340                1345                1350

Gly Val Thr Thr Gln Gly Val Lys Ser Leu Leu Thr Ser Met Tyr
    1355                1360                1365

Val Lys Glu Phe Leu Ile Ser Ser Ser Gln Asp Gly His Gln Trp
    1370                1375                1380

Thr Leu Phe Phe Gln Asn Gly Lys Val Lys Val Phe Gln Gly Asn
    1385                1390                1395

Gln Asp Ser Phe Thr Pro Val Val Asn Ser Leu Asp Pro Pro Leu
    1400                1405                1410

Leu Thr Arg Tyr Leu Arg Ile His Pro Gln Ser Trp Val His Gln
    1415                1420                1425

Ile Ala Leu Arg Met Glu Val Leu Gly Cys Glu Ala Gln Asp Leu
    1430                1435                1440

Tyr

<210> SEQ ID NO 6
<211> LENGTH: 585
<212> TYPE: PRT
<213> ORGANISM: Homo sapiens

<400> SEQUENCE: 6

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 7
<211> LENGTH: 584
<212> TYPE: PRT
<213> ORGANISM: Artificial sequence
<220> FEATURE:
<223> OTHER INFORMATION: His-tagged CTP fusion protein
<220> FEATURE:
<221> NAME/KEY: MISC_FEATURE
<222> LOCATION: (1)..(479)
<223> OTHER INFORMATION: VWF D?D3 region (VWF amino acids 764 - 1242)
<220> FEATURE:

<220> FEATURE:
<221> NAME/KEY: MISC_FEATURE
<222> LOCATION: (480)..(511)
<223> OTHER INFORMATION: glycine / serine linker
<220> FEATURE:
<221> NAME/KEY: MISC_FEATURE
<222> LOCATION: (512)..(576)
<223> OTHER INFORMATION: C-terminal peptide of human chorionic gonadotropin beta subunit
<220> FEATURE:
<221> NAME/KEY: MISC_FEATURE
<222> LOCATION: (577)..(584)
<223> OTHER INFORMATION: Polyhistidine tag

<400> SEQUENCE: 7

```
Ser Leu Ser Cys Arg Pro Pro Met Val Lys Leu Val Cys Pro Ala Asp
1               5                   10                  15

Asn Leu Arg Ala Glu Gly Leu Glu Cys Thr Lys Thr Cys Gln Asn Tyr
            20                  25                  30

Asp Leu Glu Cys Met Ser Met Gly Cys Val Ser Gly Cys Leu Cys Pro
        35                  40                  45

Pro Gly Met Val Arg His Glu Asn Arg Cys Val Ala Leu Glu Arg Cys
    50                  55                  60

Pro Cys Phe His Gln Gly Lys Glu Tyr Ala Pro Gly Glu Thr Val Lys
65                  70                  75                  80

Ile Gly Cys Asn Thr Cys Val Cys Arg Asp Arg Lys Trp Asn Cys Thr
                85                  90                  95

Asp His Val Cys Asp Ala Thr Cys Ser Thr Ile Gly Met Ala His Tyr
            100                 105                 110

Leu Thr Phe Asp Gly Leu Lys Tyr Leu Phe Pro Gly Glu Cys Gln Tyr
        115                 120                 125

Val Leu Val Gln Asp Tyr Cys Gly Ser Asn Pro Gly Thr Phe Arg Ile
    130                 135                 140

Leu Val Gly Asn Lys Gly Cys Ser His Pro Ser Val Lys Cys Lys Lys
145                 150                 155                 160

Arg Val Thr Ile Leu Val Glu Gly Gly Glu Ile Glu Leu Phe Asp Gly
                165                 170                 175

Glu Val Asn Val Lys Arg Pro Met Lys Asp Glu Thr His Phe Glu Val
            180                 185                 190

Val Glu Ser Gly Arg Tyr Ile Ile Leu Leu Leu Gly Lys Ala Leu Ser
        195                 200                 205

Val Val Trp Asp Arg His Leu Ser Ile Ser Val Val Leu Lys Gln Thr
    210                 215                 220

Tyr Gln Glu Lys Val Cys Gly Leu Cys Gly Asn Phe Asp Gly Ile Gln
225                 230                 235                 240

Asn Asn Asp Leu Thr Ser Ser Asn Leu Gln Val Glu Glu Asp Pro Val
                245                 250                 255

Asp Phe Gly Asn Ser Trp Lys Val Ser Ser Gln Cys Ala Asp Thr Arg
            260                 265                 270

Lys Val Pro Leu Asp Ser Ser Pro Ala Thr Cys His Asn Asn Ile Met
        275                 280                 285

Lys Gln Thr Met Val Asp Ser Ser Cys Arg Ile Leu Thr Ser Asp Val
    290                 295                 300

Phe Gln Asp Cys Asn Lys Leu Val Asp Pro Glu Pro Tyr Leu Asp Val
305                 310                 315                 320

Cys Ile Tyr Asp Thr Cys Ser Cys Glu Ser Ile Gly Asp Cys Ala Cys
                325                 330                 335

Phe Cys Asp Thr Ile Ala Ala Tyr Ala His Val Cys Ala Gln His Gly
```

-continued

```
            340                 345                 350
Lys Val Val Thr Trp Arg Thr Ala Thr Leu Cys Pro Gln Ser Cys Glu
        355                 360                 365

Glu Arg Asn Leu Arg Glu Asn Gly Tyr Glu Cys Glu Trp Arg Tyr Asn
    370                 375                 380

Ser Cys Ala Pro Ala Cys Gln Val Thr Cys Gln His Pro Glu Pro Leu
385                 390                 395                 400

Ala Cys Pro Val Gln Cys Val Glu Gly Cys His Ala His Cys Pro Pro
                405                 410                 415

Gly Lys Ile Leu Asp Glu Leu Leu Gln Thr Cys Val Asp Pro Glu Asp
                420                 425                 430

Cys Pro Val Cys Glu Val Ala Gly Arg Arg Phe Ala Ser Gly Lys Lys
        435                 440                 445

Val Thr Leu Asn Pro Ser Asp Pro Glu His Cys Gln Ile Cys His Cys
    450                 455                 460

Asp Val Val Asn Leu Thr Cys Glu Ala Cys Gln Glu Pro Gly Gly Ser
465                 470                 475                 480

Gly Gly Ser Gly Gly Ser Gly Gly Ser Gly Gly Ser Gly Gly Ser Gly
                485                 490                 495

Gly Ser Gly Gly Ser Gly Gly Gly Ser Gly Gly Ser Gly Ser Ser Ala
                500                 505                 510

Ser Ser Ser Ser Lys Ala Pro Pro Pro Ser Leu Pro Ser Pro Ser Arg
        515                 520                 525

Leu Pro Gly Pro Ser Asp Thr Pro Ile Leu Pro Gln Ala Ser Ser Ser
        530                 535                 540

Ser Lys Ala Pro Pro Pro Ser Leu Pro Ser Pro Ser Arg Leu Pro Gly
545                 550                 555                 560

Pro Ser Asp Thr Pro Ile Leu Pro Gln Ala Gly Gly Ser Gly Gly Ser
                565                 570                 575

His His His His His His His
                580
```